United States Patent
Seki

(10) Patent No.: US 9,527,821 B2
(45) Date of Patent: Dec. 27, 2016

(54) DEPROTECTION METHOD FOR TETRAZOLE COMPOUND

(71) Applicant: API CORPORATION, Tokyo (JP)

(72) Inventor: Masahiko Seki, Tokyo (JP)

(73) Assignee: API Corporation, Tokyo (JP)

( * ) Notice: Subject to any disclaimer, the term of this patent is extended or adjusted under 35 U.S.C. 154(b) by 54 days.

(21) Appl. No.: 14/429,257

(22) PCT Filed: Sep. 26, 2013

(86) PCT No.: PCT/JP2013/076152
§ 371 (c)(1),
(2) Date: Mar. 18, 2015

(87) PCT Pub. No.: WO2014/051008
PCT Pub. Date: Apr. 3, 2014

(65) Prior Publication Data
US 2015/0239854 A1   Aug. 27, 2015

(30) Foreign Application Priority Data
Sep. 26, 2012 (JP) .................. 2012-213212

(51) Int. Cl.
C07D 257/04 (2006.01)
C07D 403/10 (2006.01)
C07D 405/14 (2006.01)
B01J 23/58 (2006.01)

(52) U.S. Cl.
CPC .............. *C07D 257/04* (2013.01); *B01J 23/58* (2013.01); *C07D 403/10* (2013.01); *C07D 405/14* (2013.01)

(58) Field of Classification Search
None
See application file for complete search history.

(56) References Cited

U.S. PATENT DOCUMENTS

| | | |
|---|---|---|
| 2005/0131038 A1 | 6/2005 | Verardo et al. |
| 2010/0160643 A1 | 6/2010 | Pathi et al. |
| 2012/0232283 A1 | 9/2012 | Seki |
| 2015/0239853 A1 | 8/2015 | Seki |

FOREIGN PATENT DOCUMENTS

| | | |
|---|---|---|
| EP | 1 227 084 A1 | 7/2002 |
| EP | 2 891 650 A1 | 7/2015 |
| JP | H07-121918 B2 | 12/1995 |
| JP | H10-195063 A | 7/1998 |
| JP | 2002-322054 A | 11/2002 |
| JP | 2005-154442 | 6/2005 |
| JP | 2010-505926 A | 2/2010 |
| WO | WO 01-30757 A1 | 5/2001 |
| WO | WO 2004/085428 A1 | 10/2004 |
| WO | WO 2011/061996 A1 | 5/2011 |

OTHER PUBLICATIONS

Ackermann et al., *Angew Chem. Int. Ed.*, 48(52): 9792-9826 (2009).
Bernhart et al., *J. Med. Chem.*, 36(22): 3371-3380 (1993).
Beutler et al., *Organic Process Research & Development*, 11(5): 892-898 (2007).
Larsen et al., *J. Org. Chem.*, 59(21): 6391-6394 (1994).
Oi et al., *Chemistry Letters*, 37(9): 994-995 (2008).
Oi et al., *Tetrahedron*, 64(26): 6051-6059 (2008).
Japanese Patent Office, International Search Report in International Patent Application No. PCT/JP2013/076152 (Nov. 19, 2013).
Japanese Patent Office, Written Opinion of the International Search Authority in International Patent Application No. PCT/JP2013/076152 (Nov. 19, 2013).
Ford et al., *J. Med. Chem.*, 29(4): 538-549 (1986).
Klaubert et al., *J. Med. Chem.*, 24(6): 748-752 (1981).
Seki et al., *Synthesis*, 46: 3249-3255 (2014).

*Primary Examiner* — Alicia L Otton
(74) *Attorney, Agent, or Firm* — Leydig, Voit & Mayer, Ltd.

(57) ABSTRACT

The present invention relates to a method of deprotecting a tetrazole compound, useful as an intermediate for angiotensin II receptor blockers, and provides a novel production method of angiotensin II receptor blockers.

Provided is a production method of a compound represented by the formula [3] or [4] or a salt thereof, including (i) reducing a compound represented by the formula [1] or [2] or a salt thereof in the presence of a metal catalyst and an alkaline earth metal salt, or (ii) reacting the compound with a particular amount of Brønsted acid:

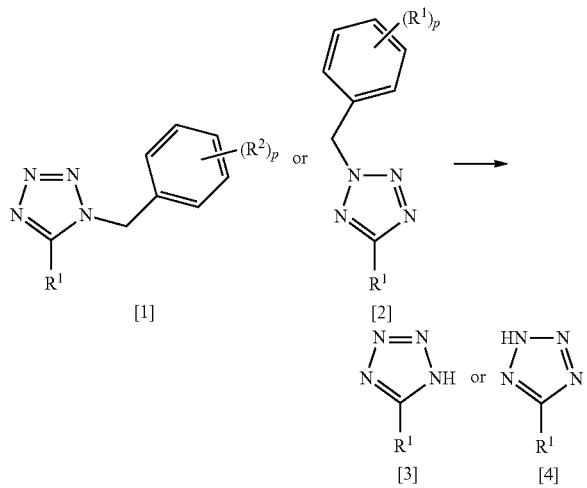

wherein each symbol is as defined in the present specification.

7 Claims, No Drawings

DEPROTECTION METHOD FOR TETRAZOLE COMPOUND

CROSS-REFERENCE TO RELATED APPLICATIONS

This patent application is the U.S. national phase of International Patent Application No. PCT/JP2013/076152, filed Sep. 26, 2013, which claims the benefit of Japanese Patent Application No. 2012-213212, filed on Sep. 26, 2012, which are incorporated by reference in their entireties herein.

TECHNICAL FIELD

The present invention relates to a deprotection method of a tetrazole compound useful as an intermediate for angiotensin II receptor blockers.

BACKGROUND ART

Losartan potassium, valsartan, olmesartan medoxomil, candesartan cilexetil, telmisartan, irbesartan and the like are useful as angiotensin II receptor blockers.

As a production method of these compounds, for example, the production method described in J. Org. Chem., 1994, vol. 59, pages 6391-6394 (non-patent document 1) is known as a synthesis method of losartan, the production method described in Org. Process Res. Dev., 2007, vol. 11, pages 892-898 (non-patent document 2) is known as a synthesis method of valsartan, and the production method described in J. Med. Chem., 1993, vol. 36, pages 3371-3380 (non-patent document 3) is known as a synthesis method of irbesartan.

As a production method of olmesartan, the production methods described in JP-B-7-121918 (patent document 1), JP-A-2010-505926 (patent document 2), WO 2004/085428 (patent document 3) and the like are known.

Also, as a conventional method of biphenylation reaction, for example, the method described in Chem. Lett., 2008, vol. 37, NO. 9, pages 994-995 (non-patent document 4), and the methods described in Tetrahedron, 2008, vol. 64, pages 6051-6059 (non-patent document 5), Angewandte Chemie International Edition, 2009, vol. 48, pages 9792-9827 (non-patent document 6), and WO 2011/061996 (patent document 4) are known.

DOCUMENT LIST

Patent Document patent document 1: JP-B-7-121918
patent document 2: JP-A-2010-505926
patent document 3: WO 2004/085428
patent document 4: WO 2011/061996

Non-Patent Document non-patent document 1: J. Org. Chem., 1994, vol. 59, pages 6391-6394
non-patent document 2: Org. Process Res. Dev., 2007, vol. 11, pages 892-898
non-patent document 3: J. Med. Chem., 1993, vol. 36, pages 3371-3380
non-patent document 4: Chem. Lett., 2008, vol. 37, No. 9, pages 994-995
non-patent document 5: Tetrahedron, 2008, vol. 64, pages 6051-6059
non-patent document 6: Angewandte Chemie International Edition, 2009, vol. 48, pages 9792-9827

SUMMARY OF THE INVENTION

Problems to be Solved by the Invention

Since the aforementioned production methods of the Prior Art require expensive metal compounds and include plural reaction steps, the development of a more economical production method has been desired.

The present invention relates to a method of deprotecting a tetrazole compound, useful as an intermediate for angiotensin II receptor blockers, under conditions that are economical and suitable for industrial production, and aims to provide a novel production method of angiotensin II receptor blockers.

Means of Solving the Problems

The present inventors have conducted intensive studies in an attempt to solve the aforementioned problems and found that a tetrazole compound, useful as an intermediate for angiotensin II receptor blockers, can be deprotected and an angiotensin II receptor blocker can be produced, under conditions that are economical and suitable for industrial production, by using a metal catalyst and an alkaline earth metal salt, or by reacting with a particular amount of Brønsted acid, which resulted in the completion of the present invention.

Accordingly, the present invention relates to;

[1] a method of producing a compound represented by the formula [3]:

wherein $R^1$ is an alkyl group, an aralkyl group or an aryl group, each of which is optionally substituted, or a salt thereof (to be also referred to as compound [3]), or the formula [4]:

wherein the symbol is as defined above, or a salt thereof (to be also referred to as compound [4]), comprising (i) reducing a compound represented by the formula [1]:

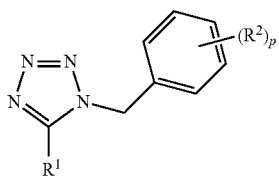

[1]

wherein $R^1$ is as defined above, each $R^2$ is an alkyl group, an alkoxy group or a nitro group, or two alkoxy groups are optionally bonded to form an alkylenedioxy group, and p is an integer of 0 to 5, or a salt thereof (to be also referred to as compound [1]), or a compound represented by the formula [2]:

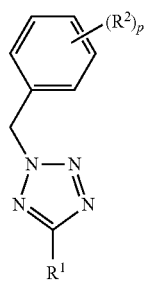

[2]

wherein each symbol is as defined above, or a salt thereof (to be also referred to as compound [2]), in the presence of a metal catalyst and an alkaline earth metal salt, or (ii) reacting compound [1] or compound [2] with 0.1 equivalents-50 equivalents of Brønsted acid relative to compound [1] or compound [2]

(hereinafter to be also referred to as "production method 1");

[2] the method of the above-mentioned [1], wherein the metal catalyst is supported by an alkaline earth metal salt;

[3] a method of producing a compound represented by the formula [23]:

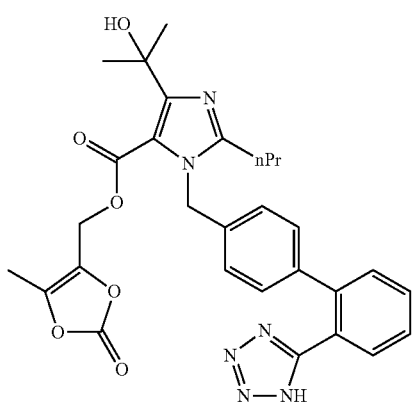

[23]

or a salt thereof (that is, olmesartan medoxomil or a salt thereof, hereinafter to be also referred to as compound [23]), comprising 1) reacting, in the presence of a base, a compound represented by the formula [11]:

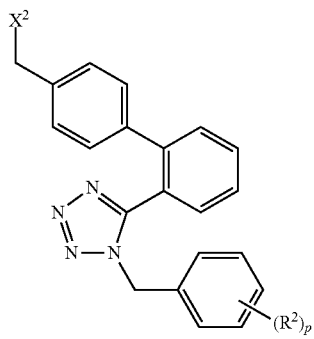

[11]

wherein each $R^2$ is an alkyl group, an alkoxy group or a nitro group, or two alkoxy groups are optionally bonded to form an alkylenedioxy group, p is an integer of 0 to 5, and $X^2$ is a halogen atom, or a salt thereof (to be also referred to as compound [11]), with a compound represented by the formula [15]:

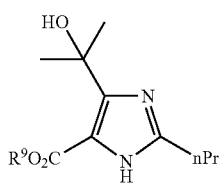

[15]

wherein $R^9$ is a carboxy-protecting group, or a salt thereof (to be also referred to as compound [15]) to give a compound represented by the formula [16]:

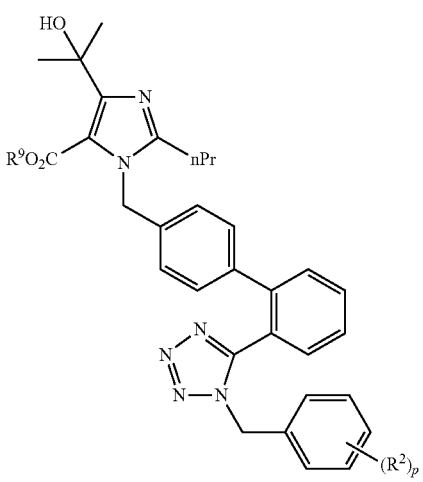

[16]

wherein the symbols are as defined above, or a salt thereof (to be also referred to as compound [16]);

2) (i) reducing compound [16] in the presence of a metal catalyst and an alkaline earth metal salt, or (ii) reacting compound [16] with 0.1 equivalents-50 equivalents of Brønsted acid relative to compound [16], to give a compound represented by the formula [17]:

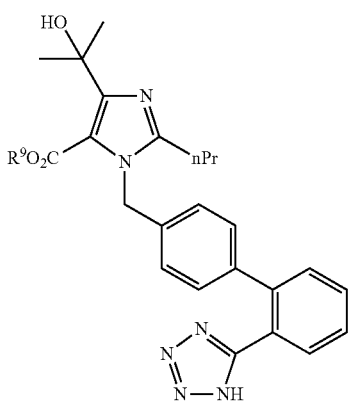

wherein the symbol is as defined above,
or a salt thereof (to be also referred to as compound [17]);
3) reacting compound [17] with a compound represented by the formula [18]: Tr-X wherein Tr is a trityl group and X is a halogen atom (to be also referred to as compound [18]) in the presence of a base to give a compound represented by the formula [19]:

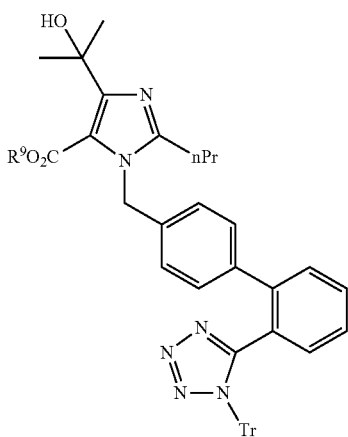

wherein the symbol is as defined above,
or a salt thereof (to be also referred to as compound [19]);
4) removing $R^9$ of compound [19] to give a compound represented by the formula [20]:

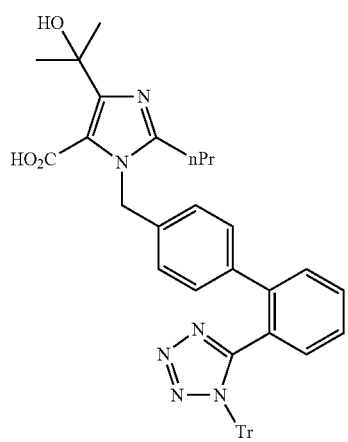

wherein the symbol is as defined above,
or a salt thereof (to be also referred to as compound [20]);

5) reacting compound [20] with a compound represented by the formula [21]:

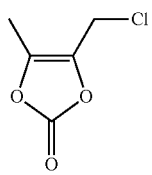

(to be also referred to as compound [21]) to give a compound represented by the formula [22]:

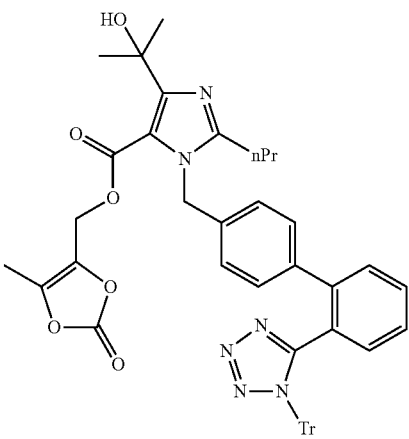

wherein the symbol is as defined above, or a salt thereof (to be also referred to as compound [22]); and 6) removing a trityl group of compound [22] (hereinafter to be also referred to as "production method 3");

[4] a method of producing a compound represented by the formula [28]:

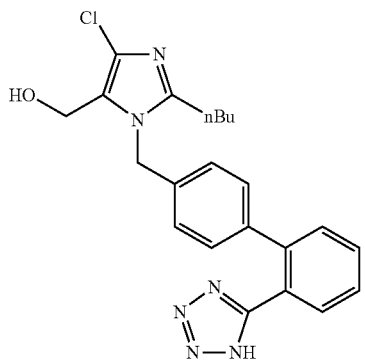

or a salt thereof (that is, losartan or a salt thereof, hereinafter to be also referred to as compound [28]), comprising 1) reacting a compound represented by the formula [11]:

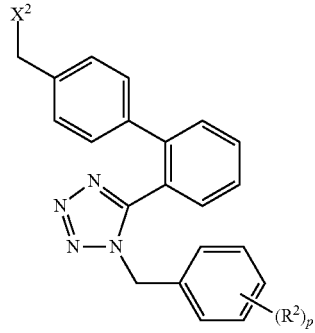

[11]

wherein each $R^2$ is an alkyl group, an alkoxy group or a nitro group, or two alkoxy groups are optionally bonded to form an alkylenedioxy group, p is an integer of 0 to 5, and $X^2$ is a halogen atom, or a salt thereof (to be also referred to as compound [11]) with a compound represented by the formula [24]:

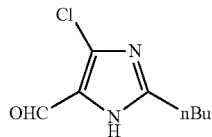

[24]

or a salt thereof (to be also referred to as compound [24]) to give a compound represented by the formula [25]:

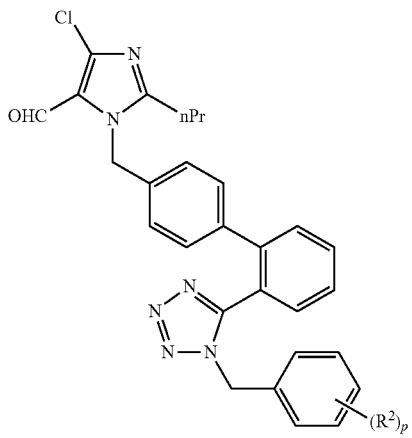

[25]

wherein the symbol is as defined above, or a salt thereof (to be also referred to as compound [25]); and 2-A) reducing compound [25] with a reducing agent to give a compound represented by the formula [26]:

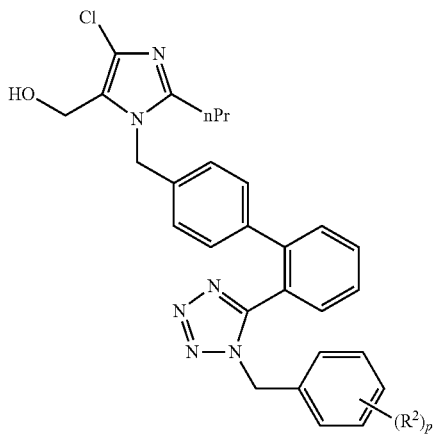

[26]

wherein the symbol is as defined above,
or a salt thereof (to be also referred to as compound [26]), and (i) further reducing compound [26] in the presence of a metal catalyst and an alkaline earth metal salt, or (ii) reacting compound [26] with 0.1 equivalents-50 equivalents of Brønsted acid relative to compound [26],
or
2-B) (i) reducing compound [25] in the presence of a metal catalyst and an alkaline earth metal salt, or (ii) reacting compound [25] with 0.1 equivalents-50 equivalents of Brønsted acid relative to compound [25], to give a compound represented by the formula [27]:

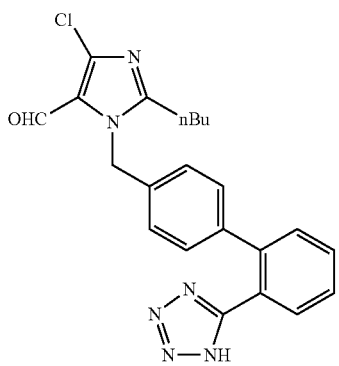

[27]

or a salt thereof (to be also referred to as compound [27]), and further reducing compound [27] with a reducing agent (hereinafter to be also referred to as "production method 4");
[5] a method of producing a compound represented by the formula [35]:

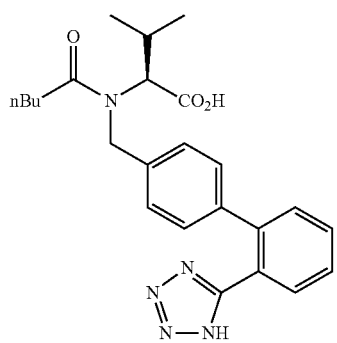

[35]

or a salt thereof (that is, valsartan or a salt thereof, hereinafter to be also referred to as compound [35]), comprising
1) reacting a compound represented by the formula [11]:

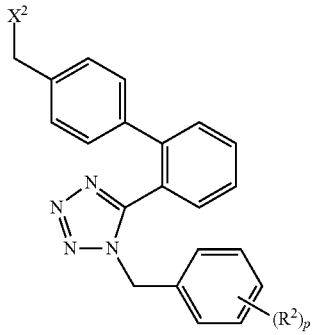
[11]

wherein each $R^2$ is an alkyl group, an alkoxy group or a nitro group, or two alkoxy groups are optionally bonded to form an alkylenedioxy group, p is an integer of 0 to 5, and $X^2$ is a halogen atom,
or a salt thereof (to be also referred to as compound [11]) with a compound represented by the formula [29]:

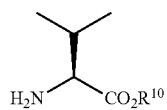
[29]

wherein $R^{10}$ is a carboxy-protecting group, or a salt thereof (to be also referred to as compound [29]) to give a compound represented by the formula [30]:

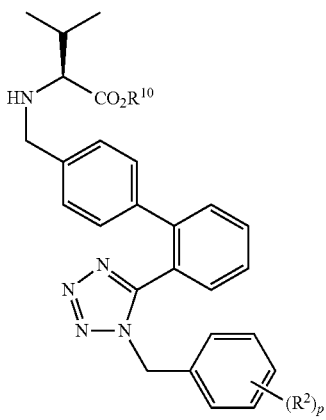
[30]

wherein the symbols are as defined above,
or a salt thereof (to be also referred to as compound [30]);
2-A) (i) reducing compound [30] in the presence of a metal catalyst and an alkaline earth metal salt, or (ii) reacting compound [30] with 0.1 equivalents-50 equivalents of Brønsted acid relative to compound [30], to give a compound represented by the formula [31]:

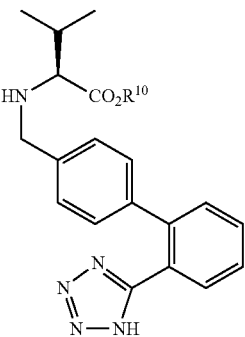
[31]

wherein the symbol is as defined above,
or a salt thereof (to be also referred to as compound [31]);
3-A) reacting compound [31] with a compound represented by the formula [32]: $CH_3CH_2CH_2CH_2CO$—$X^3$ wherein $X^3$ is a leaving group (to be also referred to as compound [32]) to give a compound represented by the formula [33]:

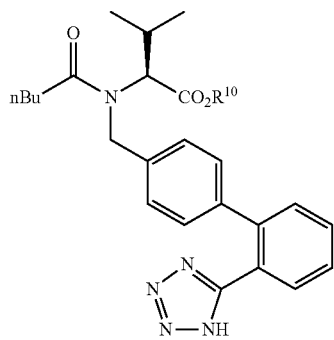
[33]

wherein the symbol is as defined above,
or a salt thereof (to be also referred to as compound [33]);
4-A) removing $R^{10}$ of compound [33]; or
2-B) reacting compound [30] with compound [32] to give a compound represented by the formula [34]:

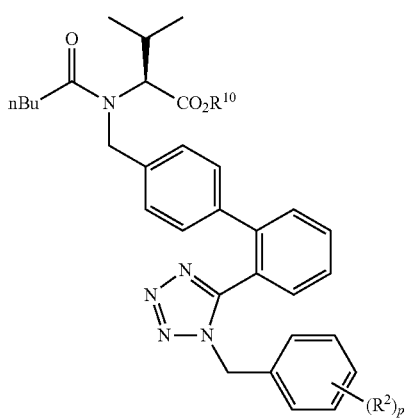
[34]

wherein the symbols are as defined above,
or a salt thereof (to be also referred to as compound [34]);
and 3-B) (i) reducing compound [34] in the presence of a metal catalyst and an alkaline earth metal salt to remove $R^{10}$ (preferably, reducing in the presence of a metal catalyst and an alkaline earth metal salt while removing $R^{10}$), or (ii) reacting compound [34] with 0.1 equivalents-50 equivalents of Brønsted acid relative to compound [34] to remove $R^{10}$ (preferably, reacting with 0.1 equivalents-50 equivalents of Brønsted acid relative to compound [34] while removing $R^{10}$) (hereinafter to be also referred to as "production method 5");

[6] a method of producing a compound represented by the formula [38]:

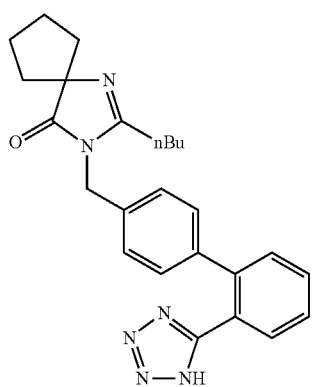

[38]

or a salt thereof (that is, irbesartan or a salt thereof, hereinafter to be also referred to as compound [38]), comprising
1) reacting a compound represented by the formula [11]:

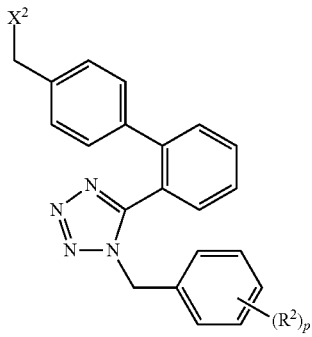

[11]

wherein each $R^2$ is an alkyl group, an alkoxy group or a nitro group, or two alkoxy groups are optionally bonded to form an alkylenedioxy group, p is an integer of 0 to 5, and $X^2$ is a halogen atom,
or a salt thereof (to be also referred to as compound [11]) with a compound represented by the formula [36]:

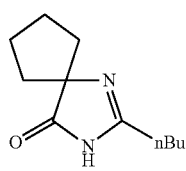

[36]

or a salt thereof (to be also referred to as compound [36]) to give a compound represented by the formula [37]:

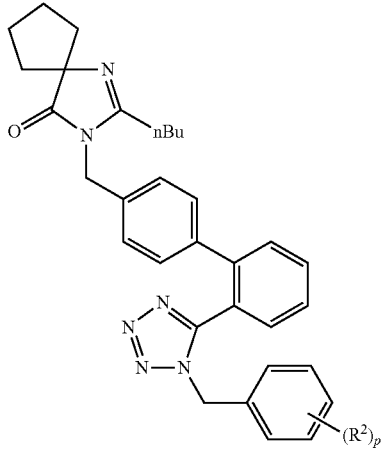

[37]

wherein the symbol is as defined above,
or a salt thereof (to be also referred to as compound [37]), and
2) (i) further reducing compound [37] in the presence of a metal catalyst and an alkaline earth metal salt, or (ii) reacting compound [37] with 0.1 equivalents-50 equivalents of Brønsted acid relative to compound [37]
(hereinafter to be also referred to as "production method 6");
[7] a method of producing a compound represented by the formula [47]:

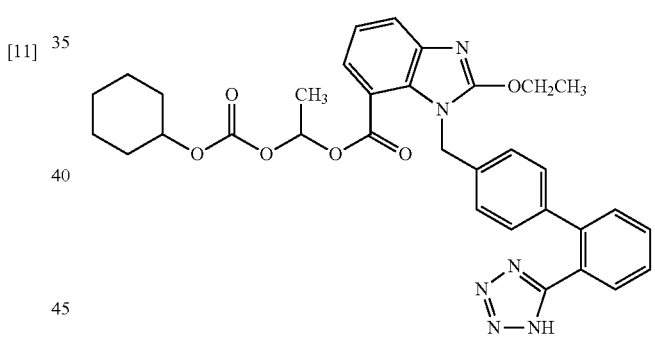

[47]

or a salt thereof (that is, candesartan cilexetil or a salt thereof, hereinafter to be also referred to as compound [47]), comprising
1-A-i) reacting a compound represented by the formula [11]:

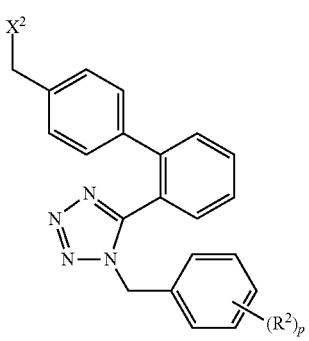

[11]

wherein each $R^2$ is an alkyl group, an alkoxy group or a nitro group, or two alkoxy groups are optionally bonded to form an alkylenedioxy group, p is an integer of 0 to 5, and $X^2$ is a halogen atom, or a salt thereof (to be also referred to as compound [11]), with a compound represented by the formula [39]:

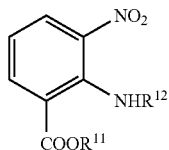
[39]

wherein $R^{11}$ is a carboxy-protecting group, and $R^{12}$ is an amino-protecting group, or a salt thereof (to be also referred to as compound [39]) to give a compound represented by the formula [40]:

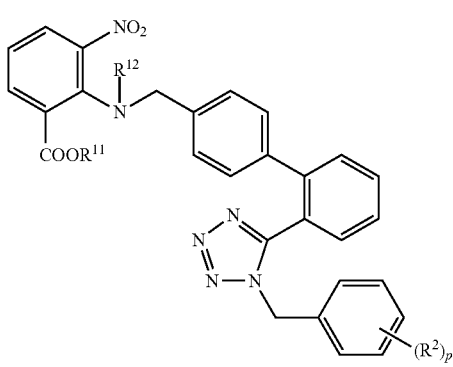
[40]

wherein the symbols are as defined above, or a salt thereof (to be also referred to as compound [40]);

1-A-ii) removing $R^{12}$ of compound [40] to give a compound represented by the formula [41]:

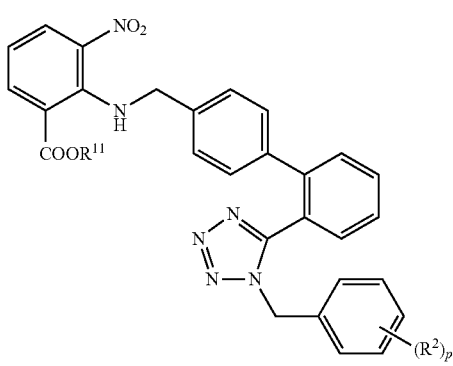
[41]

wherein the symbols are as defined above, or a salt thereof (to be also referred to as compound [41]);

1-A-iii) reducing compound [41] to give a compound represented by the formula [42]:

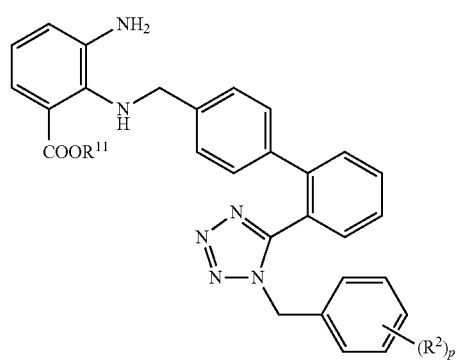
[42]

wherein the symbols are as defined above, or a salt thereof (to be also referred to as compound [42]);

1-A-iv) reacting compound [42] with tetraethoxymethane; or

1-B) reacting a compound represented by the formula [11]:

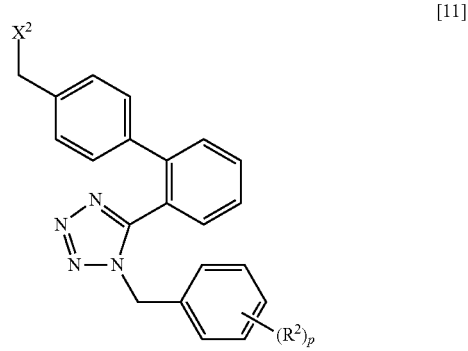
[11]

wherein each $R^2$ is an alkyl group, an alkoxy group or a nitro group, or two alkoxy groups are optionally bonded to form an alkylenedioxy group, p is an integer of 0 to 5, and $X^2$ is a halogen atom, or a salt thereof, with a compound represented by the formula [49]:

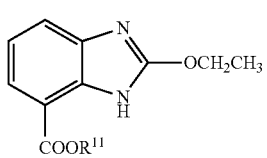
[49]

wherein the symbol is as defined above, to give a compound represented by the formula [43]:

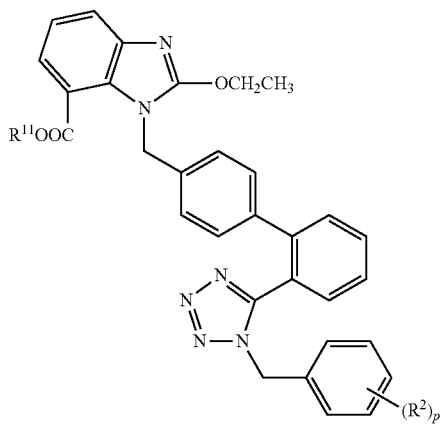

wherein the symbols are as defined above, or a salt thereof (to be also referred to as compound [43]);

2) removing $R^{11}$ of compound [43] to give a compound represented by the formula [44]:

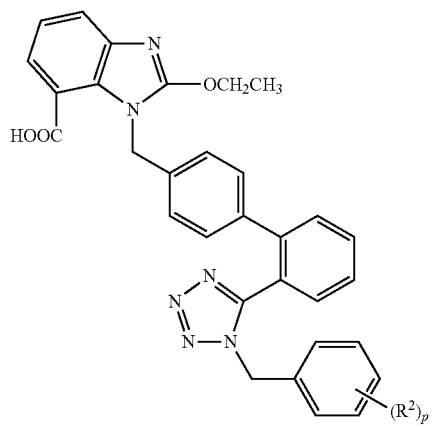

wherein the symbol is as defined above, or a salt thereof (to be also referred to as compound [44]);

3) reacting compound [44] with a compound represented by the formula [45]:

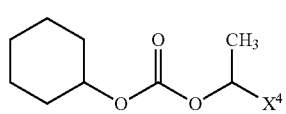

wherein $X^4$ is a leaving group or a hydroxyl group, or a salt thereof (to be also referred to as compound [45]) to give a compound represented by the formula [46]:

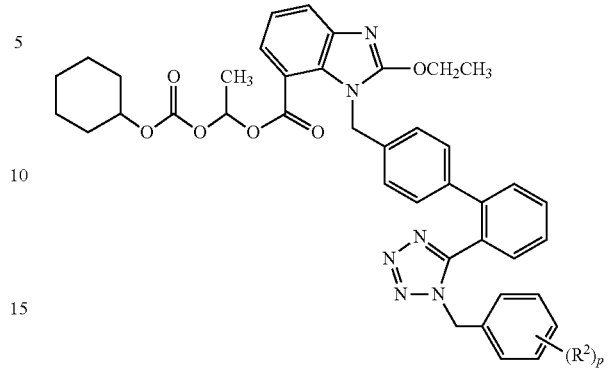

wherein the symbol is as defined above, or a salt thereof (to be also referred to as compound [46]); and 4) (i) reducing compound [46] in the presence of a metal catalyst and an alkaline earth metal salt, or (ii) reacting compound [46] with 0.1 equivalents-50 equivalents of Brønsted acid relative to compound [46]

(hereinafter to be also referred to as "production method 7");

[8] a compound represented by the formula [48]:

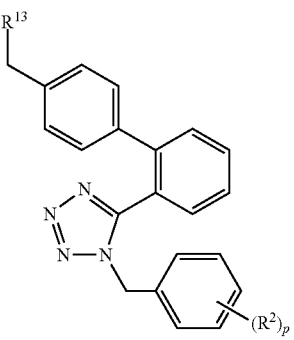

wherein each $R^2$ is an alkyl group, an alkoxy group or a nitro group, or two alkoxy groups are optionally bonded to form an alkylenedioxy group, p is an integer of 0 to 5, and $R^{13}$ is

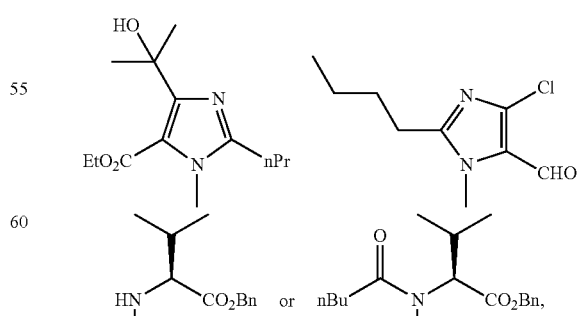

or a salt thereof;

[9] a method of producing a compound represented by the formula [3]:

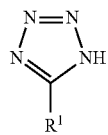

wherein $R^1$ is an alkyl group, an aralkyl group or an aryl group, each of which is optionally substituted,
or a salt thereof (to be also referred to as compound [3]), or a compound represented by the formula [4]:

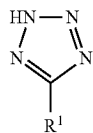

wherein the symbol is as defined above,
or a salt thereof (to be also referred to as compound [4]), comprising reducing a compound represented by the formula [1]:

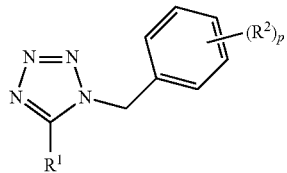

wherein $R^1$ is as defined above, each $R^2$ is an alkyl group, an alkoxy group or a nitro group, or two alkoxy groups are optionally bonded to form an alkylenedioxy group, and p is an integer of 0 to 5,
or a salt thereof (to be also referred to as compound [1]), or a compound represented by the formula [2]:

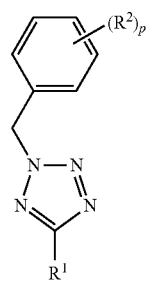

wherein the symbols are as defined above,
or a salt thereof (to be also referred to as compound [2]), in the presence of a metal catalyst and an alkaline earth metal salt
(hereinafter to be also referred to as "production method 1A");
[10] the method of the above-mentioned [9], wherein the metal catalyst is supported by the alkaline earth metal salt;

[11] a method of producing a compound represented by the formula [23]:

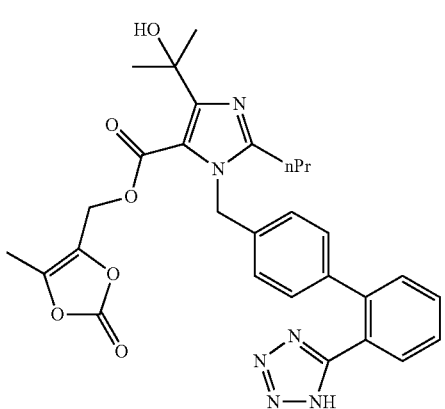

or a salt thereof (that is, olmesartan medoxomil or a salt thereof, hereinafter to be also referred to as compound [23]), comprising
1) reacting a compound represented by the formula [11]:

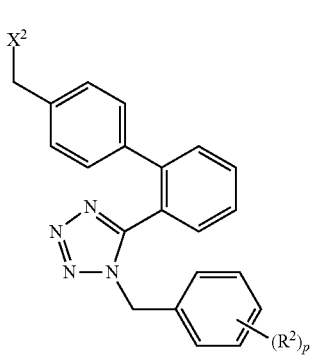

wherein each $R^2$ is an alkyl group, an alkoxy group or a nitro group, or two alkoxy groups are optionally bonded to form an alkylenedioxy group, p is an integer of 0 to 5, and $X^2$ is a halogen atom,
or a salt thereof (to be also referred to as compound [11]), in the presence of a base, with a compound represented by the formula [15]:

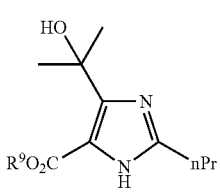

wherein $R^9$ is a carboxy-protecting group,
or a salt thereof (to be also referred to as compound [15]) to give a compound represented by the formula [16]:

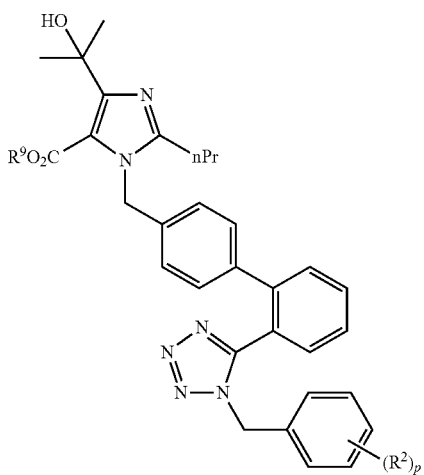

wherein the symbols are as defined above,
or a salt thereof (to be also referred to as compound [16]);
2) reducing compound [16] in the presence of a metal catalyst and an alkaline earth metal salt to give a compound represented by the formula [17]:

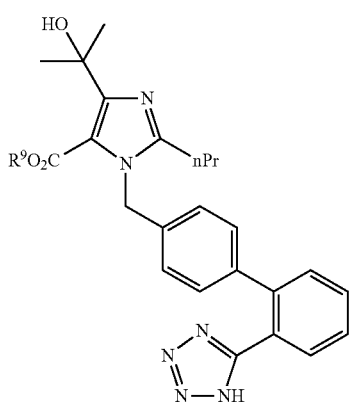

wherein the symbol is as defined above,
or a salt thereof (to be also referred to as compound [17]);
3) reacting compound [17] with a compound represented by the formula [18]: Tr-X wherein Tr is a trityl group, and X is a halogen atom (to be also referred to as compound [18]) in the presence of a base to give a compound represented by the formula [19]:

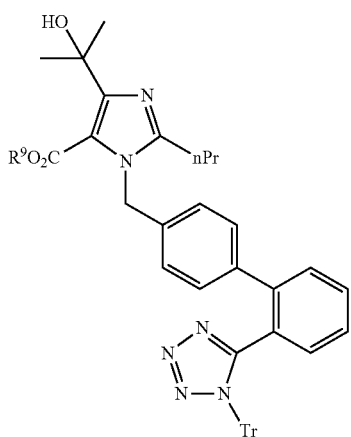

wherein the symbols are as defined above,
or a salt thereof (to be also referred to as compound [19]);
4) removing $R^9$ of compound [19] to give a compound represented by the formula [20]:

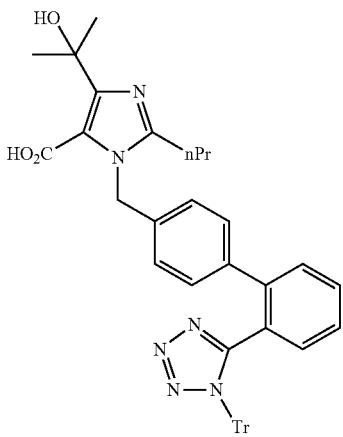

wherein the symbol is as defined above,
or a salt thereof (to be also referred to as compound [20]);
5) reacting compound [20] with a compound represented by the formula [21]:

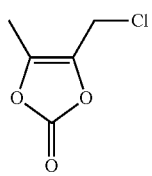

(to be also referred to as compound [21]) to give a compound represented by the formula [22]:

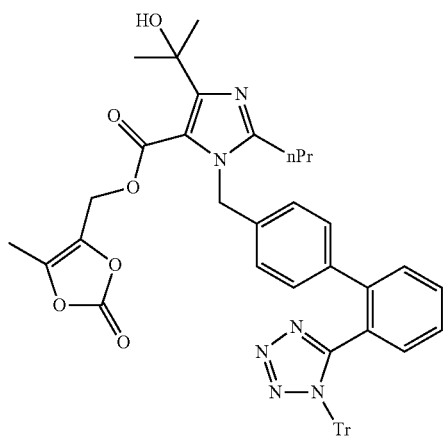

wherein the symbol is as defined above,
or a salt thereof (to be also referred to as compound [22]); and 6) removing a trityl group of compound [22]
(hereinafter to be also referred to as "production method 3A");

[12] a method of producing a compound represented by the formula [28]:

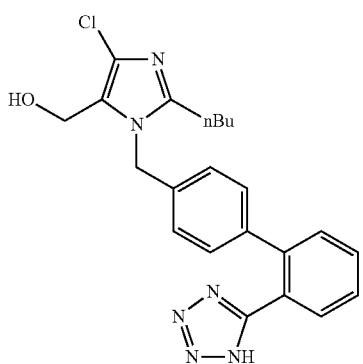

[28]

or a salt thereof (that is, losartan or a salt thereof, hereinafter to be also referred to as compound [28]), comprising 1) reacting a compound represented by the formula [11]:

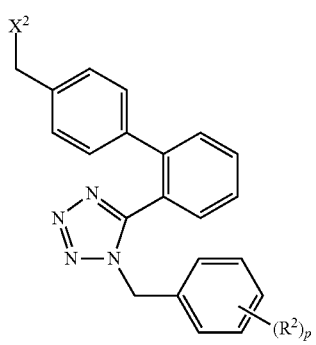

[11]

wherein each $R^2$ is an alkyl group, an alkoxy group or a nitro group, or two alkoxy groups are optionally bonded to form an alkylenedioxy group, p is an integer of 0 to 5, and $X^2$ is a halogen atom, or a salt thereof (to be also referred to as compound [11]) with a compound represented by the formula [24]:

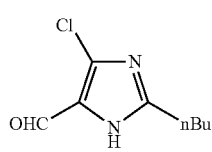

[24]

or a salt thereof (to be also referred to as compound [24]) to give a compound represented by the formula [25]:

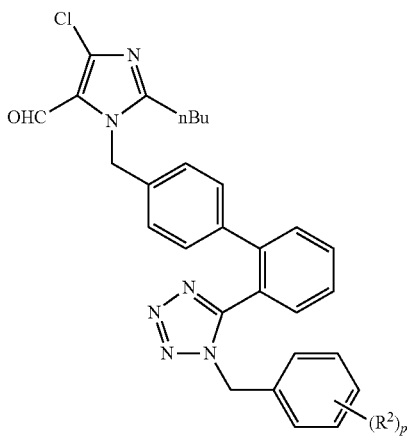

[25]

wherein the symbol is as defined above,
or a salt thereof (to be also referred to as compound [25]);
2-A) reducing compound [25] with a reducing agent to give a compound represented by the formula [26]:

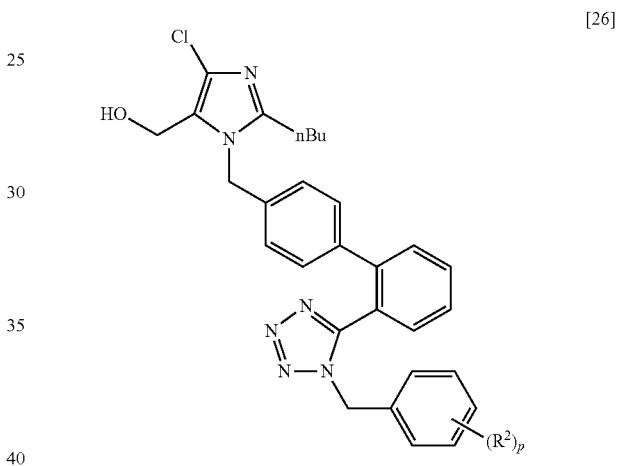

[26]

wherein the symbol is as defined above,
or a salt thereof (to be also referred to as compound [26]), further reducing compound [26] in the presence of a metal catalyst and an alkaline earth metal salt, or
2-B) reducing compound [25] in the presence of a metal catalyst and an alkaline earth metal salt to give a compound represented by the formula [27]:

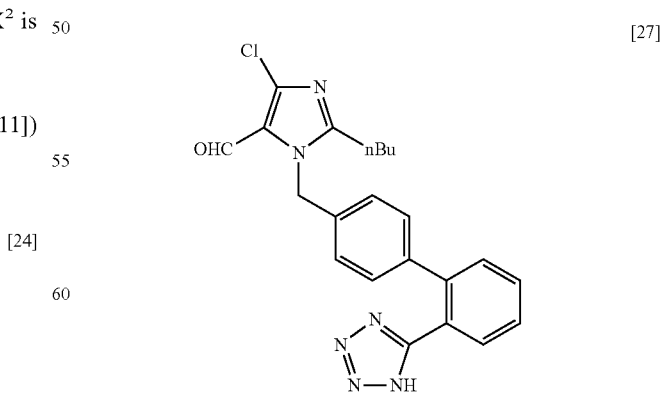

[27]

or a salt thereof (to be also referred to as compound [27]), and further reducing compound [27] with a reducing agent (hereinafter to be also referred to as "production method 4A");

[13] a method of producing a compound represented by the formula [35]:

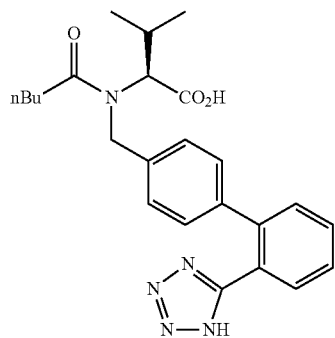

or a salt thereof (that is, valsartan or a salt thereof, hereinafter to be also referred to as compound [35]), comprising
1) reacting a compound represented by the formula [11]:

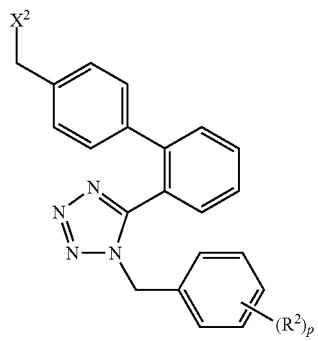

wherein each $R^2$ is an alkyl group, an alkoxy group or a nitro group, or two alkoxy groups are optionally bonded to form an alkylenedioxy group, p is an integer of 0 to 5, and $X^2$ is a halogen atom, or a salt thereof (to be also referred to as compound [11]) with a compound represented by the formula [29]:

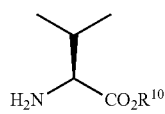

wherein $R^{10}$ is a carboxy-protecting group,
or a salt thereof (to be also referred to as compound [29]) to give a compound represented by the formula [30]:

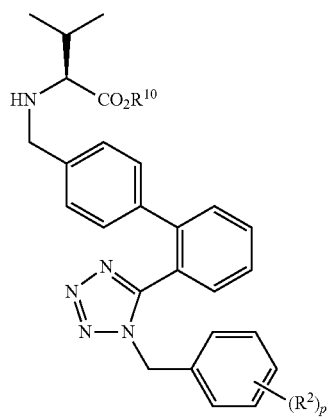

wherein the symbols are as defined above,
or a salt thereof (to be also referred to as compound [30]);
2-A) reducing compound [30] in the presence of a metal catalyst and an alkaline earth metal salt to give a compound represented by the formula [31]:

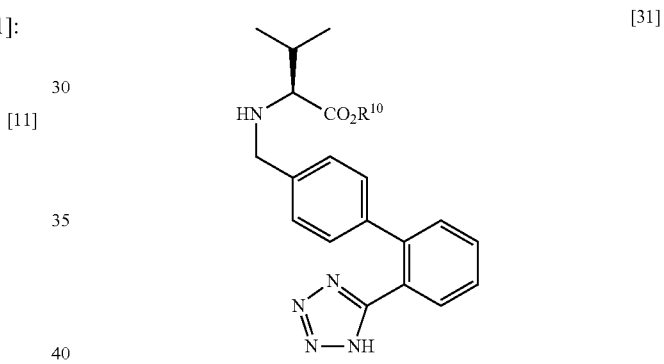

wherein the symbol is as defined above,
or a salt thereof (to be also referred to as compound [31]);
3-A) reacting compound [31] with a compound represented by the formula [32]: $CH_3CH_2CH_2CH_2CO-X^3$ wherein $X^3$ is a leaving group (to be also referred to as compound [32]) to give a compound represented by the formula [33]:

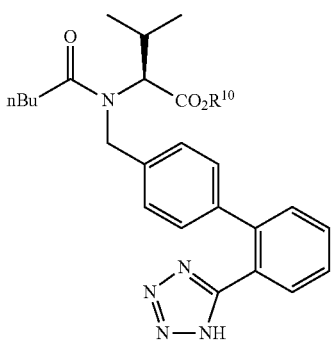

wherein the symbol is as defined above,
or a salt thereof (to be also referred to as compound [33]);

4-A) removing $R^{10}$ of compound [33]; or
2-B) reacting compound [30] with compound [32] to give a compound represented by the formula [34]:

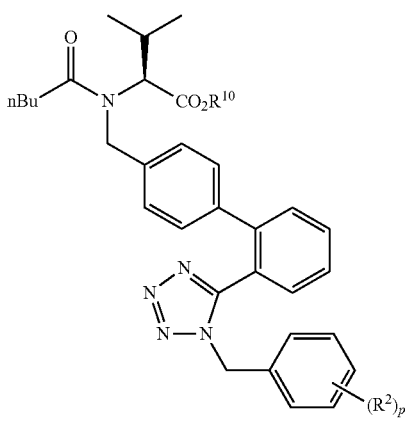

wherein the symbols are as defined above,
or a salt thereof (to be also referred to as compound [34]);
3-B) reducing compound [34] in the presence of a metal catalyst and an alkaline earth metal salt while removing $R^{10}$ (hereinafter to be also referred to as "production method 5A");
[14] a method of producing a compound represented by the formula [38]:

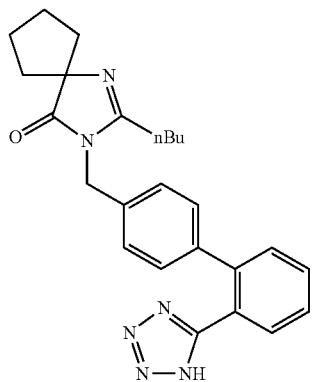

or a salt thereof (that is, irbesartan or a salt thereof, hereinafter to be also referred to as compound [38]), comprising
1) reacting a compound represented by the formula [11]:

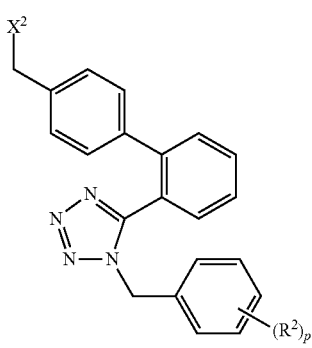

wherein each $R^2$ is an alkyl group, an alkoxy group or a nitro group, or two alkoxy groups are optionally bonded to form an alkylenedioxy group, p is an integer of 0 to 5, and $X^2$ is a halogen atom,
or a salt thereof (to be also referred to as compound [11]) with a compound represented by the formula [36]:

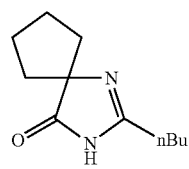

or a salt thereof (to be also referred to as compound [36]) to give a compound represented by the formula [37]:

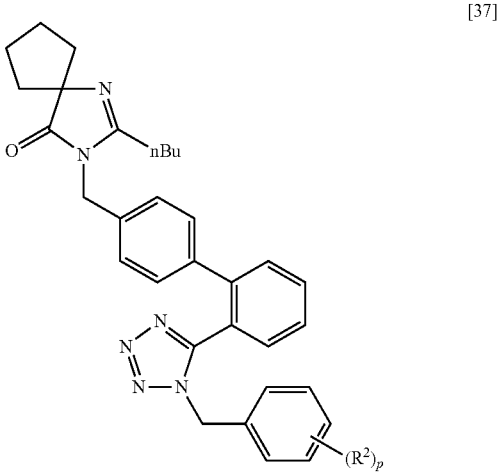

wherein the symbol is as defined above,
or a salt thereof (to be also referred to as compound [37]), and further reducing compound [37] in the presence of a metal catalyst and an alkaline earth metal salt (hereinafter to be also referred to as "production method 6A");
[15] a method of producing a compound represented by the formula [47]:

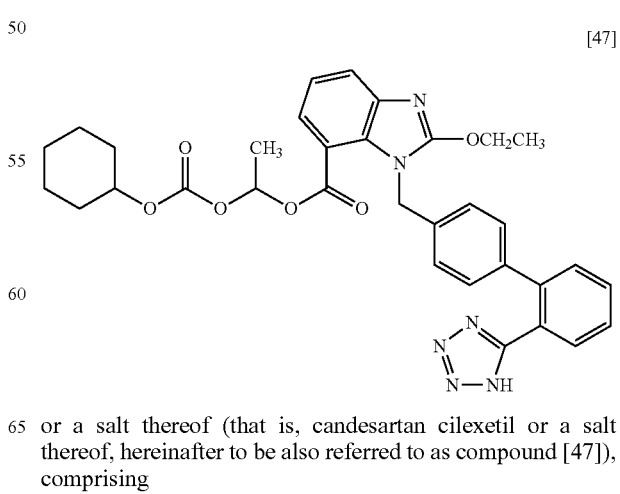

or a salt thereof (that is, candesartan cilexetil or a salt thereof, hereinafter to be also referred to as compound [47]), comprising 1) reacting a compound represented by the formula [11]:

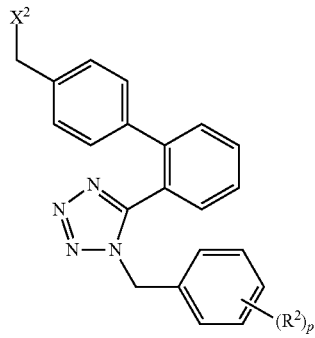

[11]

wherein each $R^2$ is an alkyl group, an alkoxy group or a nitro group, or two alkoxy groups are optionally bonded to form an alkylenedioxy group, p is an integer of 0 to 5, and $X^2$ is a halogen atom, or a salt thereof (to be also referred to as compound [11]) with a compound represented by the formula [39]:

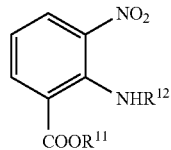

[39]

wherein $R^{11}$ is a carboxy-protecting group, and $R^{12}$ is an amino-protecting group, or a salt thereof (to be also referred to as compound [39]) to give a compound represented by the formula [40]:

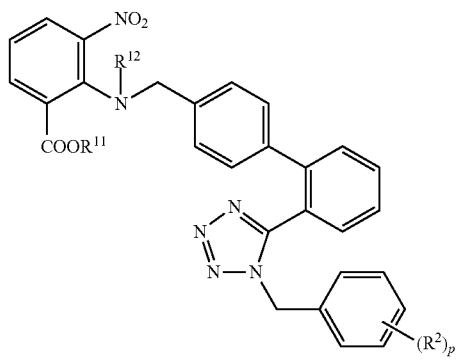

[40]

wherein the symbols are as defined above, or a salt thereof (to be also referred to as compound [40]);

2) removing $R^{12}$ of compound [40] to give a compound represented by the formula [41]:

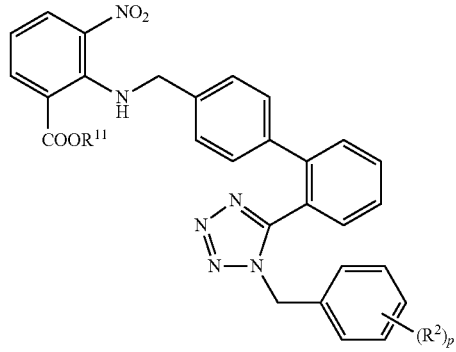

[41]

wherein the symbols are as defined above, or a salt thereof (to be also referred to as compound [41]);

3) reducing compound [41] to give a compound represented by the formula [42]:

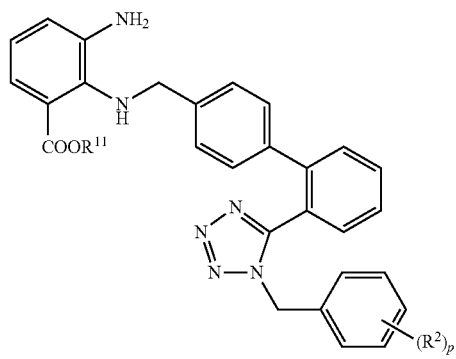

[42]

wherein the symbols are as defined above, or a salt thereof (to be also referred to as compound [42]);

4) reacting compound [42] with tetraethoxymethane to give a compound represented by the formula [43]:

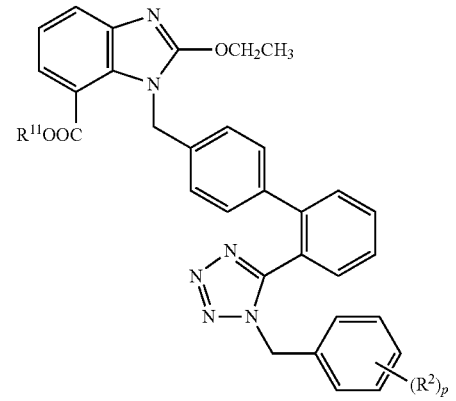

[43]

wherein the symbols are as defined above, or a salt thereof (to be also referred to as compound [43]);

5) removing $R^{11}$ of compound [43] to give a compound represented by the formula [44]:

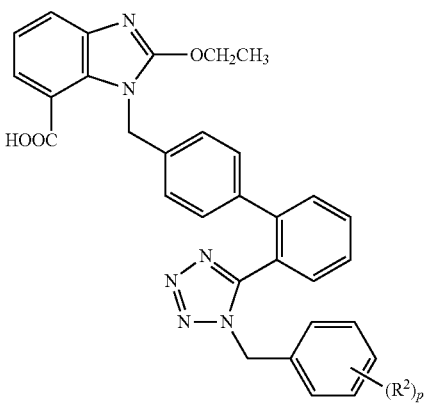

[44]

wherein the symbol is as defined above,
or a salt thereof (to be also referred to as compound [44]);
6) reacting compound [44] with a compound represented by the formula [45]:

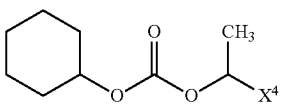

[45]

wherein $X^4$ is a leaving group or a hydroxyl group,
or a salt thereof (to be also referred to as compound [45]) to give a compound represented by the formula [46]:

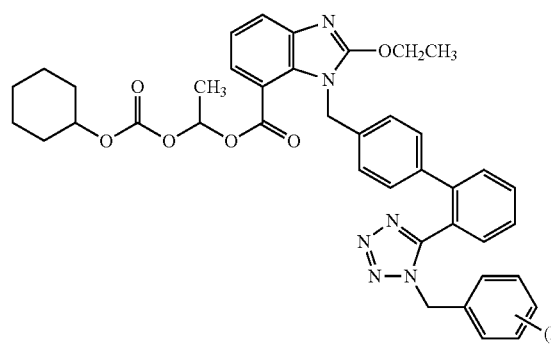

[46]

wherein the symbol is as defined above,
or a salt thereof (to be also referred to as compound [46]); and
7) reducing compound [46] in the presence of a metal catalyst and an alkaline earth metal salt
(hereinafter to be also referred to as "production method 7A").

Effect of the Invention

According to the present invention, a tetrazole compound, useful as an intermediate for angiotensin II receptor blockers, can be deprotected and an angiotensin II receptor blocker can be produced, under conditions that are economical and suitable for industrial production, by (i) reducing in the presence of a metal catalyst and an alkaline earth metal salt, or (ii) reacting with 0.1 equivalents-50 equivalents of Brønsted acid.

DESCRIPTION OF EMBODIMENTS

The definitions of the symbols and terms used in the present invention are described in detail in the following.

In the present specification, the "tetrazolyl-protecting group" is not particularly limited as long as it can stably protect a tetrazolyl group during reactions. Specifically, those described in Protective Groups in Organic Synthesis $3^{rd}$ Ed., T. W. Greene, P. G. M. Wuts, John Wiley and Sons, Inc., 1999 can be mentioned.

Examples of the tetrazolyl-protecting group include $C_{7-19}$ aralkyl group (e.g., benzyl, diphenylmethyl, trityl etc.); substituted $C_{7-19}$ aralkyl groups such as substituted benzyl, substituted diphenylmethyl and the like (preferably, $C_{7-19}$ aralkyl substituted by 1 to 3 substituents selected from the group consisting of $C_{1-6}$ alkyl, nitro, $C_{1-6}$ alkylenedioxy and $C_{1-6}$ alkoxy (when two or more substituents are present, they may be the same or different and the substituents may be bonded to each other to form a ring), for example, p-methylbenzyl, p-nitrobenzyl, 2,4-dimethoxybenzyl, 3,4-dimethoxybenzyl, 3,4-(methylenedioxy)benzyl, p-methoxybenzyl, o-methoxybenzyl, 3,4,5-trimethoxybenzyl etc.);
substituted $C_{1-6}$ alkyl group (preferably, $C_{1-6}$ alkyl substituted by 1 to 3 substituents selected from the group consisting of hydroxy, alkoxy (e.g., $C_{1-6}$ alkoxy), aryloxy (e.g., $C_{6-10}$ aryloxy) and dialkylamino (e.g., di($C_{1-6}$ alkyl)amino), for example, hydroxymethyl, alkoxymethyl, aryloxymethyl, dialkylaminomethyl etc.);
trialkylsilyl group (preferably, tri($C_{1-6}$ alkyl)silyl);
$C_{1-6}$ alkyl group (e.g., t-butyl etc.)
and the like.

In the present specification, the "carboxy-protecting group" is not particularly limited as long as it can stably protect a carboxy group during reaction, and specific examples thereof include those described in Protective Groups in Organic Synthesis $3^{rd}$ Ed., T. W. Greene, P. G. M. Wuts, John Wiley and Sons, Inc., 1999.

Examples of the carboxy-protecting group include alkyl group (preferably, $C_{1-6}$ alkyl, for example, methyl, ethyl, propyl, isopropyl, butyl, tert-butyl, pentyl, hexyl),
$C_{3-8}$ cycloalkyl group (e.g., cyclohexyl),
$C_{7-19}$ aralkyl group (e.g., benzyl, diphenylmethyl, trityl),
$C_{2-6}$ alkenyl group (e.g., allyl)
and the like.

Examples of the protecting group not deprotected by reduction (e.g., formic acid reduction, catalytic reduction) include an alkyl group, a $C_{3-8}$ cycloalkyl group and the like. Examples of the protecting group deprotected by reduction (e.g., formic acid reduction, catalytic reduction) include benzyl.

In the present specification, the "amino-protecting group" is not particularly limited as long as it can stably protect an amino group during reaction, and specific examples thereof include those described in Protective Groups in Organic Synthesis $3^{rd}$ Ed., T. W. Greene, P. G. M. Wuts, John Wiley and Sons, Inc., 1999.

Examples of the amino-protecting group include acyl group (preferably, $C_{1-6}$ alkyl-carbonyl, $C_{3-8}$ cycloalkyl-carbonyl, $C_{6-10}$ aryl-carbonyl, for example, acetyl, propionyl, butyryl, isobutyryl, pivaloyl, cyclohexylcarbonyl, benzoyl etc.), lower alkoxycarbonyl group and the like.

In the present specification, examples of the "lower alkoxycarbonyl group" include linear or branched chain $C_{1-12}$ alkoxy-carbonyl group, with preference given to methoxycarbonyl, ethoxycarbonyl, butoxycarbonyl (e.g., tert-butoxycarbonyl) and the like.

Examples of the "leaving group" for $X^1$ include halogen atom, $C_{6-10}$ arylsulfonyloxy group optionally substituted by 1 to 3 $C_{1-6}$ alkyl group (e.g., toluenesulfonyloxy etc.), $C_{1-6}$ alkylsulfonyloxy group optionally substituted by 1 to 3 halogen atoms (e.g., methanesulfonyloxy, trifluoromethanesulfonyloxy etc.)

and the like.

Examples of the "leaving group" for $X^3$ and $X^4$ include halogen atom, $C_{6-10}$ arylsulfonyloxy group optionally substituted by 1 to 3 $C_{1-6}$ alkyl groups (e.g., toluenesulfonyloxy etc.), $C_{1-6}$ alkylsulfonyloxy group optionally substituted by 1 to 3 halogen atoms (e.g., methanesulfonyloxy etc.), alkanoyloxy group (preferably, $C_{1-6}$ alkyl-carbonyloxy), aroyloxy group (preferably, $C_{6-10}$ aryl-carbonyloxy), dialkoxyphosphoryloxy group (preferably, di($C_{1-6}$ alkoxy) phosphoryloxy), diaryloxyphosphoryloxy group (preferably, di($C_{6-10}$ aryloxy)phosphoryloxy)

and the like.

Examples of the "halogen atom" in the present specification include fluorine, chlorine, bromine and iodine.

Examples of the "alkyl group" in the present specification include, unless otherwise specified, linear or branched chain alkyl groups having 1-12 carbon atoms, such as methyl, ethyl, propyl, isopropyl, butyl, isobutyl, sec-butyl, tert-butyl, pentyl, isopentyl, neopentyl, hexyl, heptyl, octyl, nonyl, decyl and the like.

Examples of the "aralkyl group" in the present specification include, unless otherwise specified, aralkyl groups having 7-14 carbon atoms, such as benzyl, phenethyl, 1-methyl-2-phenylethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like.

Examples of the "alkoxy group" in the present specification include, unless otherwise specified, linear or branched chain alkoxy groups having 1-12 carbon atoms, such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, octyloxy, nonyloxy, decyloxy and the like.

Examples of the "alkylenedioxy group" in the present specification include, unless otherwise specified, alkylenedioxy groups having 1-6 carbon atoms, such as methylenedioxy, ethylenedioxy, trimethylenedioxy, tetramethylenedioxy, pentamethylenedioxy, hexamethylenedioxy and the like.

Examples of the "aryl group" in the present specification include, unless otherwise specified, aryl groups having 6-14 carbon atoms, such as phenyl, 1-naphthyl, 2-naphthyl, 2-biphenylyl, 3-biphenylyl, 4-biphenylyl, 2-anthryl and the like. The aryl group may be fused with "$C_{3-8}$ cycloalkane" or "$C_{3-8}$ cycloalkene" described below and, for example, tetrahydronaphthyl and the like can be mentioned.

Examples of the "heterocyclic group" in the present specification include, unless otherwise specified, a 3- to 14-membered (monocyclic, bicyclic or tricyclic)heterocyclic group containing, as a ring-constituting atom besides carbon atom, one or two kinds of 1 to 4 heteroatoms selected from a nitrogen atom, a sulfur atom and an oxygen atom, which is optionally fused with carbocycle. Preferred are (i) 5- to 14-membered (preferably, 5- to 10-membered) aromatic heterocyclic group, (ii) 3- to 14-membered non-aromatic heterocyclic group and the like. Of these, a 5- or 6-membered aromatic heterocyclic group or a 5- to 10-membered non-aromatic heterocyclic group is preferable.

Specific examples thereof include aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1-triazolyl, 2-triazolyl), tetrazolyl, pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furyl (e.g., 2-benzo[b]furyl, 3-benzo[b]furyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazolopyridinyl (e.g., pyrazolo[1,5-a]pyridin-3-yl) and the like;

non-aromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., piperidino, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, morpholino), thiomorpholinyl (e.g., 2-thiomorpholinyl, 3-thiomorpholinyl, thiomorpholino), tetrahydrofuryl, tetrahydropyranyl, 1,3-azaspiro[4.4]nonenyl and the like, and the like.

Examples of the "cycloalkyl group" in the present specification include, unless otherwise specified, cycloalkyl groups having 3-8 carbon atoms, such as cyclopropyl, cyclobutyl, cyclopentyl, cyclohexyl, cycloheptyl, cyclooctyl and the like.

Examples of the "$C_{3-8}$ cycloalkane" in the present specification include cyclopropane, cyclobutane, cyclopentane, cyclohexane, cycloheptane, cyclooctane and the like.

Examples of the "$C_{3-8}$ cycloalkene" in the present specification include cyclopropene, cyclobutene, cyclopentene, cyclohexene and the like.

Examples of "an alkyl group, an aralkyl group or an aryl group, each of which is optionally substituted" in the present specification include "alkyl group", "aralkyl group" and "aryl group", each optionally having, at substitutable position(s), 1 to 5 substituents selected from (1) a halogen atom;
(2) hydroxy;
(3) amino;
(4) nitro;
(5) cyano;
(6) a heterocyclic group optionally substituted by 1 to 3 substituents selected from halogen atom, hydroxy, amino, nitro, cyano, $C_{1-6}$ alkyl optionally substituted by 1 to 3 halogen atoms or hydroxy, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkoxy-carbonyl, $C_{7-14}$ aralkyloxy-carbonyl, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl, mono- or di-$C_{6-14}$ aryl-sulfamoyl, oxo and $C_{3-8}$ cycloalkyloxycarbonyloxy-$C_{1-6}$ alkoxy-carbonyl;
(7) mono- or di-$C_{1-6}$ alkyl-amino;
(8) mono- or di-$C_{6-14}$ aryl-amino;
(9) mono- or di-$C_{7-14}$ aralkyl-amino;
(10) N—$C_{1-6}$ alkyl-N—$C_{6-14}$ aryl-amino;
(11) N—$C_{1-6}$ alkyl-N—$C_{7-14}$ aralkyl-amino;
(12) $C_{3-8}$ cycloalkyl;
(13) optionally halogenated $C_{1-6}$ alkoxy;
(14) $C_{1-6}$ alkylsulfanyl;
(15) $C_{1-6}$ alkylsulfinyl;
(16) $C_{1-6}$ alkylsulfonyl;
(17) optionally esterified carboxyl;
(18) $C_{1-6}$ alkyl-carbonyl;
(19) $C_{3-8}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) N—$C_{1-6}$ alkyl-N—$C_{6-14}$ aryl-carbamoyl;
(26) mono- or di-5- to 7-membered heterocyclyl-carbamoyl;
(27) $C_{1-6}$ alkyl-carbonylamino optionally substituted by carboxyl;
(28) $C_{6-14}$ aryloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(29) $C_{6-14}$ aryl optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(30) heterocyclyl-oxy;
(31) sulfamoyl;
(32) mono- or di-$C_{1-6}$ alkyl-sulfamoyl;
(33) mono- or di-$C_{6-14}$ aryl-sulfamoyl;
(34) $C_{7-14}$ aralkyloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(35) $C_{1-6}$ alkyl-carbonyloxy;
(36) $C_{7-14}$ aralkyloxy-carbonyl;
(37) tri-$C_{1-6}$ alkylsilyloxy;
(38) $C_{1-6}$ alkyl;
(39) $C_{2-6}$ alkenyl;
(40) $C_{2-6}$ alkynyl;
(41) $C_{1-6}$ alkoxy-carbonyl;
(42) N—$C_{1-6}$ alkyl (said $C_{1-6}$ alkyl is optionally substituted by $C_{7-14}$ aralkyloxy-carbonyl)-N—$C_{1-6}$ alkyl-carbonylamino; and the like. When a plurality of substituents exist, the respective substituents may be the same or different. The substituents are optionally further substituted by 1 to 5 substituents selected from the above-mentioned (1)-(42). When a plurality of substituents exist, the respective substituents may be the same or different.

Examples of the "linear or branched chain alkyl group having 1-20 carbon atoms, aralkyl group having 7-14 carbon atoms, aryl group having 6-18 carbon atoms and cycloalkyl group having 3-7 carbon atoms, each optionally having a nitrogen atom, an oxygen atom or a sulfur atom" in the present specification include dimethylaminomethyl, methoxymethyl, methylthiomethyl, anilinomethyl, phenoxymethyl, pyridyl, pyrimidyl, piperidinyl, morpholinyl and the like.

The deprotection method in the present invention is explained below.

[Production Method 1] and [Production Method 1A] (Deprotection Method)
(i) Deprotection Method by Reducing in the Presence of Metal Catalyst and Alkaline Earth Metal Salt

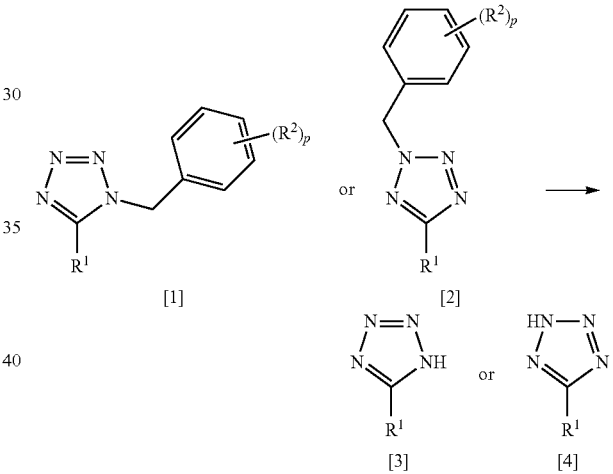

wherein $R^1$ is an alkyl group, an aralkyl group or an aryl group, each of which is optionally substituted, each $R^2$ is an alkyl group, an alkoxy group or a nitro group, or two alkoxy groups are optionally bonded to form an alkylenedioxy group, and p is an integer of 0 to 5.

Compound [3] or [4] can be produced by reduction (e.g., formic acid reduction, catalytic reduction etc.) of compound [1] or [2] in the presence of a metal catalyst and an alkaline earth metal salt, followed by deprotection (elimination of the following substituent).

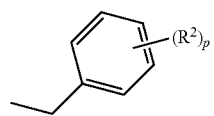

Compounds [3] and [4] form an equilibrium mixture.

Examples of the metal catalyst include palladium catalyst, rhodium catalyst, platinum catalyst and the like. Preferred is palladium catalyst.

The amount of the metal catalyst to be used is generally 0.00001 equivalents-1 equivalent, preferably, 0.001 equivalents-0.5 equivalents, more preferably, 0.01 equivalents-0.1 equivalents, relative to compound [1] or [2].

While the alkaline earth metal salt is not particularly limited, for example, an alkaline earth metal salt of inorganic acid can be mentioned. Preferred is barium sulfate or calcium carbonate.

The amount of the alkaline earth metal salt to be used is generally 0.00001 equivalents-1 equivalent, preferably, 0.001 equivalents-0.5 equivalents, more preferably, 0.01 equivalents-0.1 equivalents, relative to compound [1] or [2].

The metal catalyst can also be used by being supported by an alkaline earth metal salt. It is preferably a supported type palladium catalyst, particularly preferably palladium barium sulfate (Rosenmund catalyst) or palladium calcium carbonate (Lindlar catalyst).

In the case of formic acid reduction, formic acid or formic acid salt (ammonium formate, sodium formate, potassium formate, lithium formate, magnesium formate etc.) is added as an additive.

In the case of catalytic reduction, the hydrogen pressure is 1 atm-100 atm, preferably 1 atm-10 atm.

Reduction (deprotection) can also be performed in the presence of a solvent. While the solvent is not particularly limited as long as the reaction proceeds, isopropyl alcohol, n-propyl alcohol, methanol, ethanol, tetrahydrofuran, methylene chloride, ethyl acetate and the like, or a mixed solvent of the above-mentioned solvent and water can be mentioned. The amount of the solvent to be used is generally 0.1 mL-100 mL, preferably 0.5 mL-10 mL, per 1 mmol of compound [1] or [2].

The reaction temperature is generally 0° C.-150° C., preferably, 10° C.-80° C.

The reaction time is generally 0.1 hr-72 hr, preferably, 0.5 hr-24 hr.

The above-mentioned compound [1] or [2] can be produced by the method described in WO 2011/061996, or a method analogous thereto. For example, a biphenyltetrazole derivative can be produced by the following method.

(ii) Deprotection Method by Reaction with Brønsted Acid

Compound [3] or [4] can be produced by reacting compound [1] or [2] with 0.1 equivalents-50 equivalents of Brønsted acid relative to compound [1] or [2]. It is industrially preferable since a catalyst is not necessary for the reaction with Brønsted acid.

In the case of deprotection by this method, $R^1$ in compounds [1], [2], [3] and [4] is preferably a benzyl group substituted by an alkoxy group, particularly preferably a benzyl group wherein the 2-position and the 4-position are substituted by the same alkoxy group. As the alkoxy group, an alkoxy group having 1-6 carbon atoms is preferable, an alkoxy group having 1-3 carbon atoms is further preferable. Particularly preferred is a methoxy group.

As Brønsted acid, trifluoroacetic acid, methanesulfonic acid, p-toluenesulfonic acid, hydrochloric acid, sulfuric acid, phosphoric acid, phosphate and the like can be mentioned. Preferred is trifluoroacetic acid. The amount of the Brønsted acid to be used is generally 0.1-50 equivalents, preferably 0.5 equivalents-10 equivalents, relative to compound [1] or [2].

While the solvent is not particularly limited as long as the reaction proceeds, halogenated solvents such as methylene chloride, chloroform, chlorobenzene and the like, polar solvents such as N-methyl-2-pyrrolidone, N,N-dimethylformamide, N,N-dimethylacetamide, dimethyl sulfoxide, water and the like, and non-polar solvents such as toluene, xylene and the like are preferable. These halogenated solvents, polar solvents and/or non-polar solvents may be used as a mixture. The amount of the solvent to be used is generally 0 mL-100 mL, preferably 0.1 mL-10 mL, per 1 mmol of compound [1] or [2].

This method can be performed in the presence of a scavenger as necessary. While the scavenger is not particularly limited as long as the reaction proceeds, mercaptans such as anisole, mesitylene, 1-octanethiol and the like, and the like can be mentioned. The amount of the scavenger to be used is generally 0.001 mL-10 mL, preferably 0.1 mL-5 mL, per 1 mmol of compound [1] or [2].

The reaction temperature is generally 0° C.-100° C., preferably 5° C.-50° C., particularly preferably 10° C.-40° C.

The reaction time is generally 0.01-200 hr, preferably 0.5-12 hr.

[Production Method 2]

2-Phenyltetrazole derivative [5] and benzene derivative [6] may be commercially available products, and 2-phenyltetrazole derivative [5] may be produced by the method described in WO 2009/49305, or a method analogous thereto.

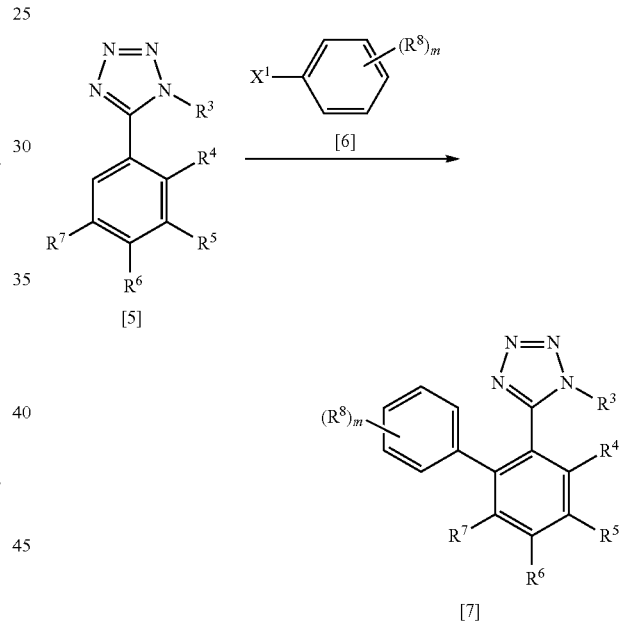

wherein $R^3$ is a tetrazolyl-protecting group, $R^4$ to $R^7$ are each independently a hydrogen atom or an alkyl group, an aralkyl group or an aryl group, each optionally having substituent(s), $R^8$ is an alkyl group, an aralkyl group or an aryl group, each optionally having substituent(s), m is an integer of 0 to 5, and $X^1$ is a leaving group.

Biphenyltetrazole derivative [7] can be produced by reacting 2-phenyltetrazole derivative [5] with benzene derivative [6] in the presence of a metal catalyst, a base and one or more kinds of compounds selected from the group consisting of the aforementioned (a)-(d). This reaction can also be performed in a solvent.

As the metal catalyst, ruthenium catalyst, iridium catalyst, rhodium catalyst or palladium catalyst can be used. Examples of the ruthenium catalyst include dichlorotris(triphenylphosphine)ruthenium (II) ($RuCl_2(PPh_3)_3$), dichloro(1,5-cyclooctadiene)ruthenium (II) polymer (sometimes indicated as $[RuCl_2(\eta^4\text{-COD})]_n$ or $poly[(\eta^2,\eta^2\text{-cy-}$ cloocta-1,5-diene)ruthenium-di-μ-chloro]), [RuCl$_2$(η$^6$-C$_6$H$_6$)]$_2$, dichloro(p-cymene)ruthenium (II) dimer ([Ru(p-cymene)Cl$_2$]$_2$), dichloro(mesitylene)ruthenium (II) dimer ([Ru(mesitylene)Cl$_2$]$_2$), ruthenium chloride (III) (RuCl$_3$), ruthenium chloride (III) hydrate (RuCl$_3$.xH$_2$O), ruthenium carbon, and dipivaloyloxy(p-cymene)ruthenium (II). Preferred are ruthenium catalysts (e.g., dichloro(p-cymene) ruthenium (II) dimer ([Ru(p-cymene)Cl$_2$]$_2$), ruthenium chloride (III) hydrate (RuCl$_3$.xH$_2$O), dipivaloyloxy(p-cymene) ruthenium (II)).

The amount of the metal catalyst to be used is generally 0.00001-10 equivalents, preferably, 0.001 equivalents-0.3 equivalents, more preferably, 0.003 equivalents-0.015 equivalents, relative to 2-phenyltetrazole derivative [5].

Examples of the base include potassium carbonate (K$_2$CO$_3$), sodium carbonate (Na$_2$CO$_3$), sodium hydrogen carbonate (NaHCO$_3$), potassium hydrogen carbonate (KHCO$_3$), potassium phosphate (K$_3$PO$_4$), cesium carbonate (Cs$_2$CO$_3$), rubidium carbonate (Rb$_2$CO$_3$) and the like. Preferred is potassium carbonate.

The amount of the base to be used is generally 0.1 equivalents-10 equivalents, preferably, 0.1 equivalents-3 equivalents, more preferably, 0.3 equivalents-2 equivalents, relative to 2-phenyltetrazole derivative [5].

While (a) monocarboxylic acid metal salt of the present invention is not particularly limited, for example, a carboxylic acid metal salt represented by RCO$_2$M and the like can be mentioned.

R is a hydrogen atom, or a straight chain or branched chain alkyl group having 1-20 carbon atoms, an aralkyl group having 7-14 carbon atoms, an aryl group having 6-18 carbon atoms or a cycloalkyl group having 3-7 carbon atoms, each of which optionally contains a nitrogen atom, an oxygen atom or a sulfur atom, and the alkyl group, aralkyl group, cycloalkyl group and aryl group optionally have substituent(s). R is preferably a straight chain or branched chain alkyl group having 1-12 carbon atoms (e.g., methyl, tert-butyl, 2-ethyl-hexyl, n-dodecyl), an aralkyl group having 7-10 carbon atoms, an aryl group having 6-12 carbon atoms optionally substituted by an alkyl group having 1-6 carbon atoms (e.g., mesityl), or a cycloalkyl group having 3-7 carbon atoms (e.g., cyclohexyl), particularly preferably, a methyl group or a tert-butyl group.

M is a metal atom, which is preferably Li (lithium), Na (sodium), K (potassium), Rb (rubidium), Cs (cesium), Mg (magnesium) or Zn (zinc), more preferably an alkali metal atom, particularly preferably K.

Preferable examples of the monocarboxylic acid metal salt include a potassium salt of carboxylic acid wherein R is a straight chain or branched chain alkyl group having 1-12 carbon atoms (e.g., methyl, tert-butyl, 2-ethyl-hexyl, n-dodecyl), a cycloalkyl group having a having 3-7 carbon atoms (e.g., cyclohexyl), or an aryl group having 6-12 carbon atoms (e.g., mesityl) optionally substituted by an alkyl group having 1-6 carbon atoms, and a potassium salt of acetic acid or a potassium salt of pivalic acid is particularly preferable.

While (b) dicarboxylic acid metal salt of the present invention is not particularly limited, for example, a metal salt of dicarboxylic acid represented by

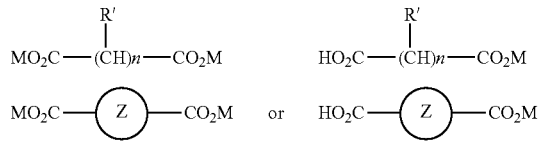

and the like can be mentioned.

R' is a hydrogen atom, or a straight chain or branched chain alkyl group having 1-10 carbon atoms, an aralkyl group having 7-14 carbon atoms or an aryl group having 6-18 carbon atoms, each of which optionally contains a nitrogen atom, an oxygen atom or a sulfur atom. The alkyl group, aralkyl group and aryl group optionally have substituent(s). R' is preferably a hydrogen atom, or a straight chain or branched chain alkyl group having 1-6 carbon atoms, an aralkyl group having 7-10 carbon atoms, or an aryl group having 6-12 carbon atoms, and particularly preferable a hydrogen atom.

n is an integer of 0-10, preferably, an integer of 0-5, particularly preferably, 0 or 3.

Ring Z is cycloalkylene having 3-8 carbon atoms, cycloalkenylene having 3-8 carbon atoms, arylene, or heterocyclylene, preferably, phenylene, naphthylene, anthrylene, phenanthrylene or the like.

M is a metal atom, preferably, Li (lithium), Na (sodium), K (potassium), Rb (rubidium), Cs (cesium), Mg (magnesium) or Zn (zinc), more preferably, an alkali metal atom, particularly preferably, K.

A preferable example of a dicarboxylic acid metal salt is a potassium salt of dicarboxylic acid wherein R' is a hydrogen atom and n is an integer of 0-5, and a potassium salt of oxalic acid and a potassium salt of glutaric acid are particularly preferable.

While (c) sulfonic acid metal salt of the present invention is not particularly limited, for example, a sulfonic acid metal salt represented by R"SO$_3$M and the like can be mentioned.

R" is a hydrogen atom, or a straight chain or branched chain alkyl group having 1-10 carbon atoms, an aralkyl group having 7-14 carbon atoms or an aryl group having 6-18 carbon atoms, each of which optionally contains a nitrogen atom, an oxygen atom or a sulfur atom. The alkyl group, aralkyl group and aryl group optionally have substituent(s). Preferred are a straight chain or branched chain alkyl group having 1-6 carbon atoms, an aralkyl group having 7-10 carbon atoms, and an aryl group having 6-12 carbon atoms (e.g., 2,4,6-trimethylphenyl or 4-dodecylphenyl) which is optionally substituted by an alkyl group having 1-12 carbon atoms, and particularly preferred is a 4-dodecylphenyl group.

M is a metal atom, preferably, Li (lithium), Na (sodium), K (potassium), Rb (rubidium), Cs (cesium), Mg (magnesium) or Zn (zinc), more preferably, an alkali metal atom, particularly preferably, K. A preferable example of (c) a sulfonic acid metal salt of the present invention is a potassium salt of sulfonic acid wherein R" is a phenyl group optionally substituted by an alkyl group having 1-12 carbon atoms, and potassium 4-dodecylbenzenesulfonate is particularly preferable.

R'" of (d) phosphate metal salt represented by (R'"O)$_x$P(O)(OM)$_y$ of the present invention is a hydrogen atom, or a straight chain or branched chain alkyl group having 1-20 carbon atoms, an aralkyl group having 7-14 carbon atoms or an aryl group having 6-18 carbon atoms, each of which optionally contains a nitrogen atom, an oxygen atom or a sulfur atom. The alkyl group, aralkyl group and aryl group optionally have substituent(s). Two R'" may form a ring in a molecule. Preferred are a straight chain or branched chain alkyl group having 1-12 carbon atoms (e.g., ethyl, n-butyl, t-butyl, dodecyl, 2-ethyl-n-hexyl), an aralkyl group having 7-10 carbon atoms and an aryl group having 6-12 carbon atoms (e.g., 2-naphthyl), and particularly preferred is a 2-ethyl-n-hexyl group.

x and y are each independently an integer of 1 or 2, and x+y is 3.

M is a metal atom, preferably, Li (lithium), Na (sodium), K (potassium), Rb (rubidium), Cs (cesium), Mg (magnesium) or Zn (zinc), more preferably, an alkali metal atom, particularly preferably, K.

A preferable example of (d) phosphate metal salt represented by (R'''O)$_x$P(O)(OM)$_y$ of the present invention is a potassium salt of phosphate wherein R''' is a straight chain or branched chain alkyl group having 1-12 carbon atoms (e.g., ethyl, n-butyl, t-butyl, dodecyl, 2-ethyl-n-hexyl) or an aryl group having 6-12 carbon atoms (e.g., 2-naphthyl), and potassium bis(2-ethyl-n-hexyl)phosphate is particularly preferable.

The amount of one or more kinds of compounds selected from the group consisting of (a)-(d) to be used is generally 0.00001 equivalents-10 equivalents, preferably, 0.001 equivalents-8.0 equivalents, more preferably, 0.005 equivalents-5.0 equivalents, relative to 2-phenyltetrazole derivative [5].

A method of adding a metal catalyst, a base and one or more kinds of compounds selected from the group consisting of (a)-(d) is not particularly limited, and a method including adding a base and one or more kinds of compounds selected from the group consisting of (a)-(d), and then adding a metal catalyst, a method including adding a base, and then adding a ruthenium catalyst prepared from a metal catalyst and one or more kinds of compounds selected from the group consisting of (a)-(d) and the like can be mentioned.

For preferable progress of the reaction, the reaction may be performed in the further presence of a phosphine compound. Examples of the phosphine compound include triphenylphosphine (sometimes referred to as triphenylphosphane), tri(t-butyl)phosphine, triethylphosphine, tricyclohexylphosphine, tri(o-tolyl)phosphine, tri(p-tolyl)phosphane, tri(p-methoxyphenyl)phosphane, cyclohexyldiphenylphosphane and the like, with preference given to triphenylphosphine.

The amount of the phosphine compound to be used is generally 0.00001 equivalents-10 equivalents, preferably, 0.001 equivalents-1 equivalent, relative to 2-phenyltetrazole derivative [5].

In addition, the reaction may be performed in the presence of a conjugate acid of a metal salt described in the above-mentioned (a)-(d).

The amount of the conjugate acid to be used is generally 0.00001 equivalents-3 equivalents, preferably, 0.05 equivalents-1.0 equivalent, more preferably, 0.1 equivalents-0.5 equivalents, relative to 2-phenyltetrazole derivative [5].

While the solvent is not particularly limited as long as the reaction proceeds, polar solvents such as N-methyl-2-pyrrolidone (sometimes to be abbreviated as NMP), N,N-dimethylformamide (sometimes to be abbreviated as DMF), N,N-dimethylacetamide (sometimes to be abbreviated as DMA), dimethyl sulfoxide (sometimes to be abbreviated as DMSO) and the like, non-polar solvents such as toluene, xylene and the like, and a mixture of the polar solvent and the non-polar solvent are preferable.

The amount of the solvent to be used is generally 0 mL-100 mL, preferably, 0.1 mL-10 mL, per 1 mmol of 2-phenyltetrazole derivative [5].

The reaction temperature is generally 20° C.-300° C., preferably, 100° C.-200° C.

The reaction time is generally 0.01 hr-200 hr, preferably, 0.5 hr-24 hr.

[Production Method 2-1]

Compound [11] which is compound [1] wherein R$^1$ is 4'-halomethylbiphenyl-2-yl can be produced by the following method.

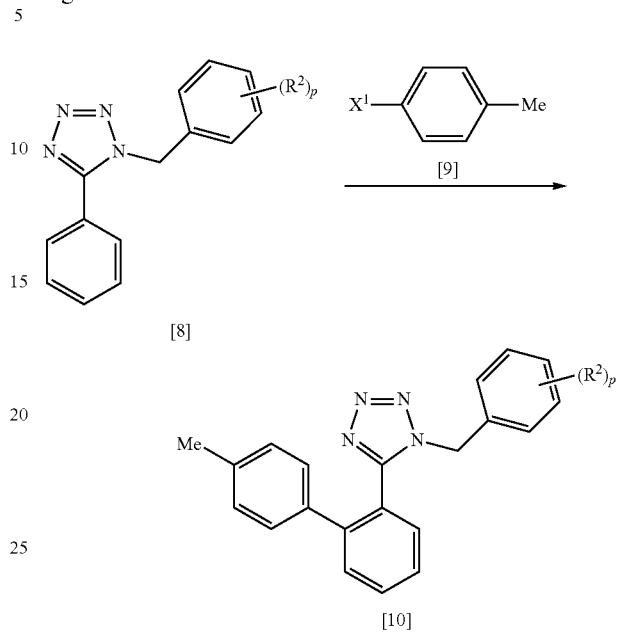

wherein the symbols are as defined above.

(Step 1)

A biphenyltetrazole derivative or a salt thereof [10] can be produced by processing a phenyltetrazole derivative or a salt thereof [8] and a benzene derivative [9] in the same manner as in the method described in the above-mentioned Production method 2.

(Step 2)

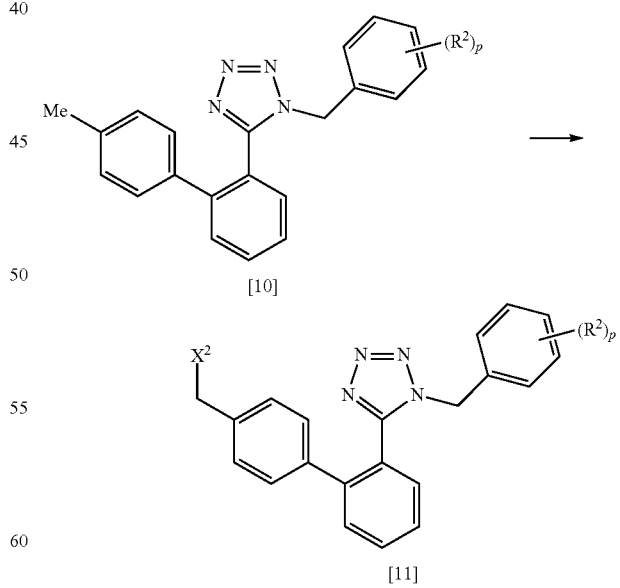

wherein R$^2$ is as defined above, and X$^2$ is a halogen atom.

Compound [11] can be produced by reacting a biphenyltetrazole derivative or a salt thereof [10] with a halogenating agent.

As the halogenating agent, a halogenating agent known per se can be used. Preferably, 1,3-dibromo-5,5-dimethylhydantoin (DBDMH), sodium bromate (NaBrO$_3$) and the like can be mentioned. The amount of the halogenating agent to be used is generally 0.1 equivalents-10 equivalents, preferably 0.5 equivalents-1.1 equivalents, relative to the biphenyltetrazole derivative or a salt thereof [10].

The reaction can also be performed in the presence of a reaction initiator. As the reaction initiator, 2,2'-azobisisobutyronitrile (AIBN), benzoyl peroxide (BPO) and the like can be mentioned. The amount of the reaction initiator to be used is generally 0.0001 equivalents-10 equivalents, preferably 0.005 equivalents-0.1 equivalents, relative to the biphenyltetrazole derivative or a salt thereof [10].

To accelerate the reaction rate, the reaction can also be performed in the presence of an acid. As the acid, aromatic acid is preferable, for example, p-toluenesulfonic acid, benzenesulfonic acid, 2,4,6-trimethylbenzoic acid, 1-adamantylcarboxylic acid and the like can be mentioned, and p-toluenesulfonic acid is particularly preferable. The amount of the acid to be used is generally 0.00001 equivalents-10 equivalents, preferably 0.01 equivalents-5 equivalents, relative to the biphenyltetrazole derivative or a salt thereof [10].

The reaction can also be performed using a solvent. While the solvent is not particularly limited as long as the reaction proceeds, ester solvents such as ethyl acetate, methyl acetate and the like, non-polar solvents such as cyclohexane, n-hexane, n-heptane and the like, halogen solvents such as methylene chloride, chloroform, carbon tetrachloride and the like, ether solvents such as tert-butyl methyl ether, THF and the like, polar solvents such as N-methyl-2-pyrrolidone, N,N-dimethylformamide, N,N-dimethylacetamide, dimethyl sulfoxide, water and the like, and a mixture of these polar solvents and non-polar solvents are preferable. The amount of the solvent to be used is generally 0 mL-100 mL, preferably 0.1 mL-10 mL, per 1 mmol of the biphenyltetrazole derivative or a salt thereof [10].

The reaction temperature is generally 0° C.-200° C., preferably 20° C.-110° C.

The reaction time is generally 0.01 hr-200 hr, preferably 0.5 hr-24 hr.

[Production Method 2-2]

A compound which is compound [7] wherein R$^4$ to R$^7$ are hydrogen, R$^8$ is 4-bromomethyl, and m is 1 can be produced by the following method.

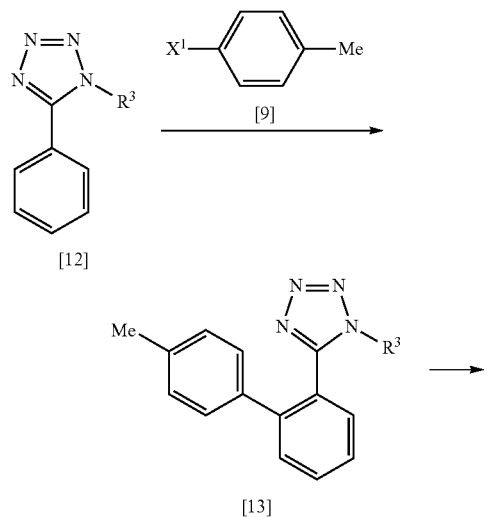

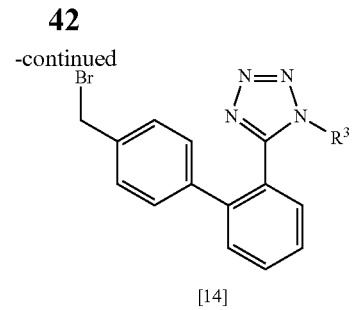

wherein the symbols are as defined above.

(Step 1)

A biaryltetrazole derivative or a salt thereof [13] can be produced by processing a phenyltetrazole derivative or a salt thereof [12] and a benzene derivative [9] in the same manner as in the method described in the above-mentioned Production method 2.

Of the biaryltetrazole derivatives or a salt thereof [13] obtained in this step, one wherein R$^3$ is benzyl is superior in crystallinity and can be purified by a mere crystallization step.

(Step 2)

A biaryltetrazole derivative or a salt thereof [14] can be produced by reacting a biaryltetrazole derivative or a salt thereof [13] with a brominating agent by a method similar to that in the above-mentioned Production method 2-1, step 2.

As the brominating agent, 1,3-dibromo-5,5-dimethylhydantoin (DBDMH) or sodium bromate (NaBrO$_3$) is preferably used.

[Production Method 3] and [Production Method 3A] (Olmesartan Medoxomil Production Method)

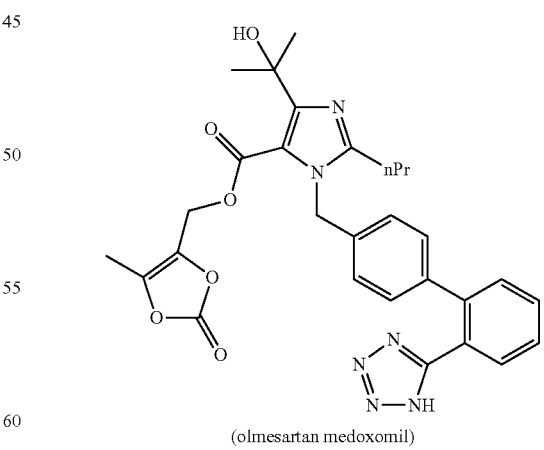

(olmesartan medoxomil)

Olmesartan medoxomil or a salt thereof can be produced from compound [11] by a known method described in JP-B-7-121918, JP-A-2010-505926 and the like. It can also be produced by the following method.

(Step 1)

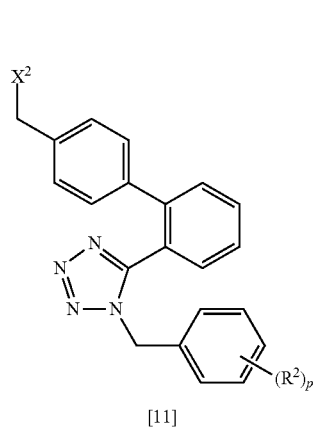

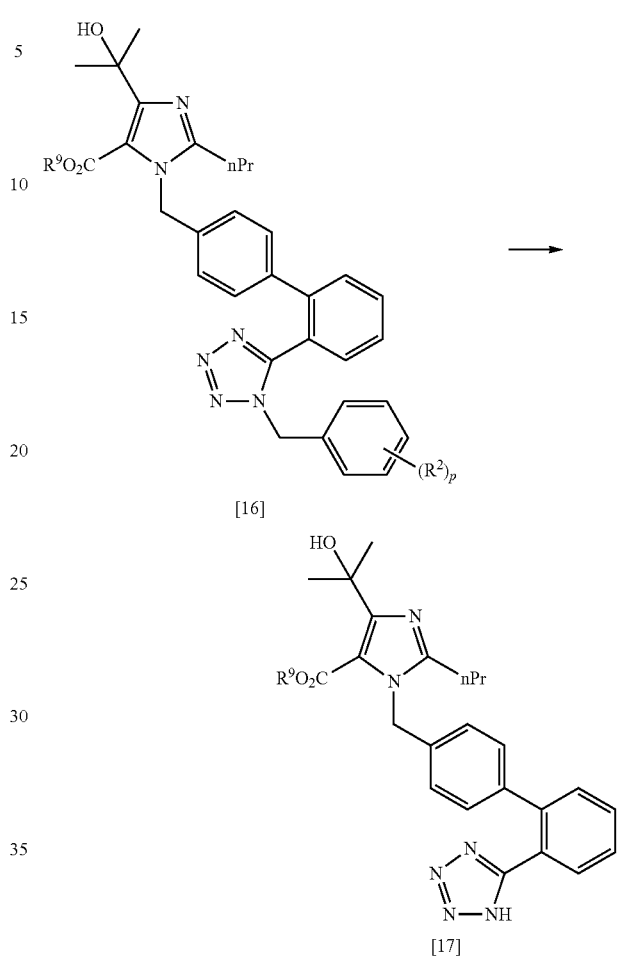

wherein $R^9$ is a carboxy-protecting group, and other symbols are as defined above.

Compound [16] can be produced by reacting compound [11] with compound [15] in the presence of a base. This reaction can also be performed in a solvent.

$R^9$ in compound [15] is a carboxy-protecting group, and is a protecting group not deprotected by reduction (e.g., formic acid reduction, catalytic reduction). Preferred is an alkyl group.

The base is not particularly limited, and a base known per se can be applied. For example, potassium carbonate, cesium carbonate, sodium hydroxide, potassium hydroxide, triethylamine, diisopropylethylamine, 1,8-diazabicyclo[5.4.0]undec-7-ene (DBU) and the like can be mentioned. The amount of the base to be used is generally 1 equivalent-10 equivalents, preferably 1 equivalent-3 equivalents, relative to compound [11].

The solvent is not particularly limited as long as the reaction proceeds, and DMA, DMF, DMSO, NMP, acetonitrile, toluene, THF, dioxane, acetone and the like can be mentioned. The amount of the solvent to be used is generally 0.001 mL-100 mL, preferably 0.1 mL-10 mL, per 1 mmol of compound [11].

The reaction temperature is generally −50° C.-150° C., preferably 20° C.-50° C.

The reaction time is generally 0.1 hr-48 hr, preferably 0.5 hr-5 hr.

(Step 2)

wherein the symbols are as defined above.

Compound [17] can be produced using compound [16] in the same manner as in the method described in the above-mentioned Production method 1.

(Step 3)

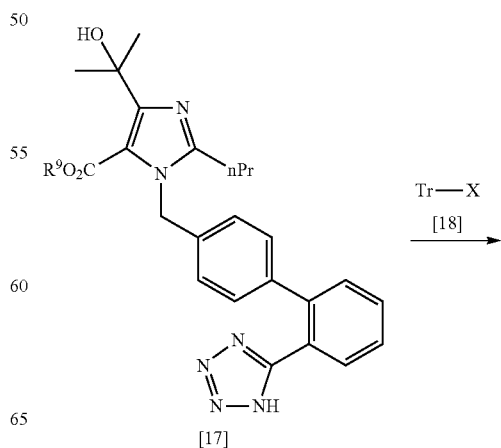

-continued

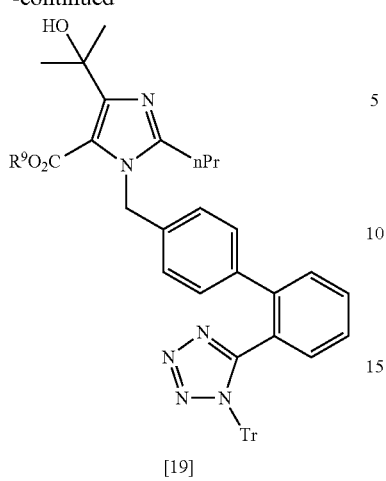

[19]

wherein Tr is a trityl group, X is a halogen atom, R[9] is as defined above.

Compound [19] can be produced by reacting compound [17] with compound [18] in the presence of a base. This reaction can also be performed in a solvent.

The base is not particularly limited, and a base known per se can be applied. For example, triethylamine, N,N-diisopropylethylamine, pyridine, lutidine, sodium carbonate, potassium carbonate, cesium carbonate and the like can be mentioned. The amount of the base to be used is generally 0.1 equivalents-10 equivalents, preferably 1 equivalent-5 equivalents, relative to compound [17].

The solvent is not particularly limited as long as the reaction proceeds, and methylene chloride, chloroform, toluene, acetone, tetrahydrofuran, ethyl acetate, N,N-dimethylformamide and the like can be mentioned. The amount of the solvent to be used is generally 0.01 mL-50 mL, preferably 0.5 mL-5 mL, per 1 mmol of compound [17].

The reaction temperature is generally −10° C.-50° C., preferably −5° C.-30° C.

The reaction time is generally 0.1 hr-24 hr, preferably 1 hr-5 hr.

(Step 4)

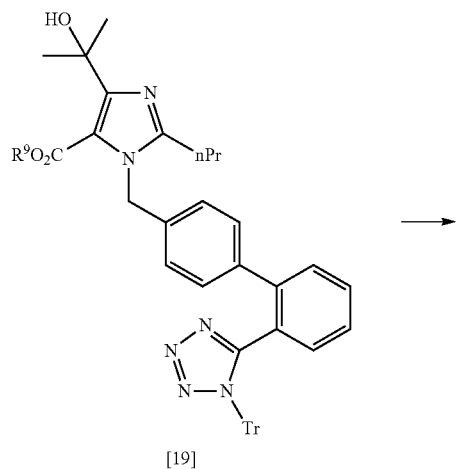

[19]

-continued

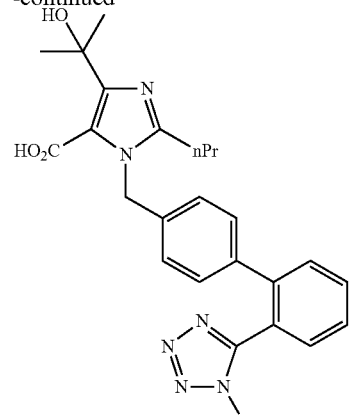

[20]

wherein the symbols are as defined above.

Compound [20] can be produced by hydrolysis of compound [19] in the presence a base and a water-soluble organic solvent.

While the base is not particularly limited, a base known per se can be applied. For example, potassium hydroxide, potassium carbonate, sodium hydroxide, sodium hydride and the like can be mentioned. The amount of the base to be used is generally 1 equivalent-10 equivalents, preferably 1 equivalent-3 equivalents, relative to compound [19].

As the water-soluble organic solvent, methanol, ethanol, acetone and the like can be mentioned. The amount of the solvent to be used is generally 0.001 mL-100 mL, preferably 0.1 mL-10 mL, per 1 mmol of compound [19].

The reaction temperature is generally 0° C.-120° C., preferably 50° C.-100° C.

The reaction time is generally 0.1 hr-48 hr, preferably 0.5 hr-5 hr.

(Step 5)

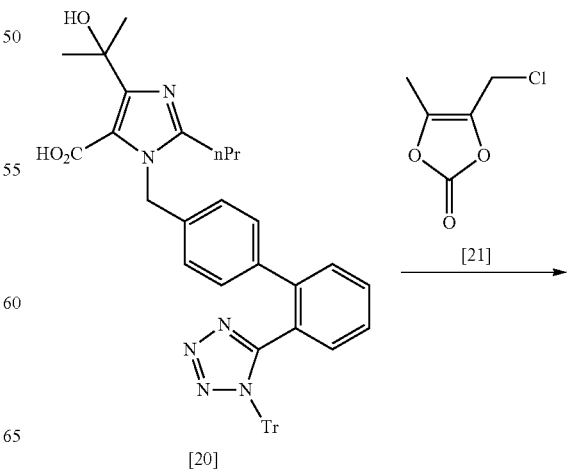

[20]

-continued

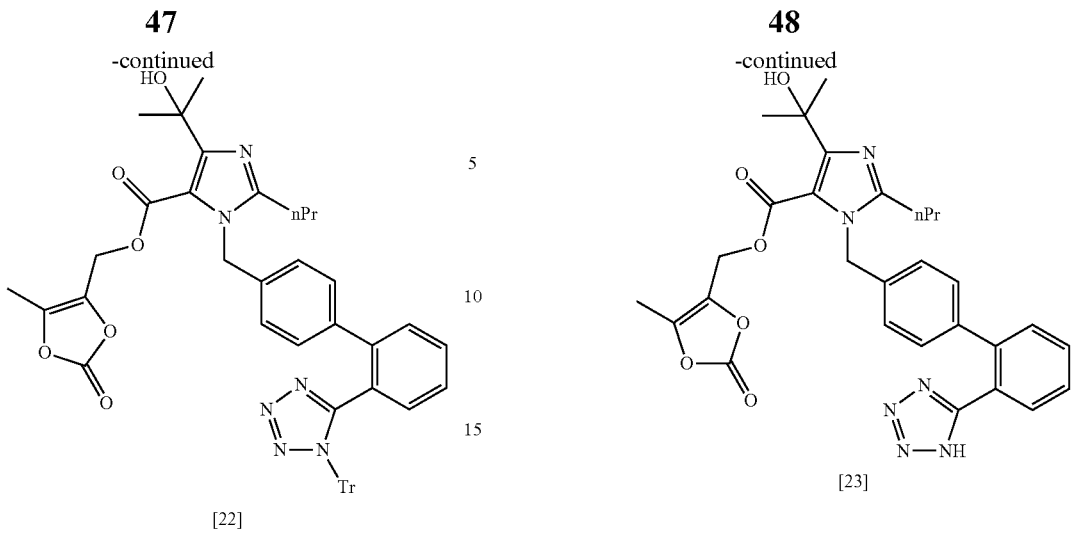

[22]

wherein Tr is as defined above.

Compound [22] can be produced by reacting compound [20] with compound [21] in the presence of a base.

The base is not particularly limited, and a base known per se can be applied. For example, potassium carbonate, cesium carbonate, sodium hydroxide, potassium hydroxide, triethylamine, diisopropylethylamine, 1,8-diazabicyclo [5.4.0]undec-7-ene (DBU) and the like can be mentioned. The amount of the base to be used is generally 1 equivalent-10 equivalents, preferably 1 equivalent-3 equivalents, relative to compound [20].

The solvent is not particularly limited as long as the reaction proceeds, and DMA, DMF, DMSO, NMP, acetonitrile, toluene, THF, dioxane, acetone and the like can be mentioned. The amount of the solvent to be used is generally 0.001 mL-100 mL, preferably 0.1 mL-10 mL, per 1 mmol of compound [20].

The reaction temperature is generally 0° C.-150° C., preferably 30° C.-100° C.

The reaction time is generally 0.1 hr-48 hr, preferably 0.5 hr-5 hr.

(Step 6)

wherein Tr is as defined above.

Compound [23] (olmesartan medoxomil or a salt thereof) can be produced by removing a trityl group of compound [22]. This reaction can also be performed in a solvent.

To remove $R^6$, an acid can be used. The acid is not particularly limited, and acids known per se can be applied. For example, trifluoroacetic acid, trichloroacetic acid, trifluoromethanesulfonic acid, methanesulfonic acid, sulfuric acid, hydrochloric acid, acetic acid and the like can be mentioned. The amount of the acid to be used is generally 0.1 equivalents-1000 equivalents, preferably 1 equivalent-500 equivalents, relative to compound [22].

Removal of a trityl group by an acid can be preferably performed in the presence of a scavenger. While the scavenger is not particularly limited as long as the reaction proceeds, mercaptans such as anisole, mesitylene, 1-octanethiol and the like, and the like can be mentioned. The amount of the scavenger to be used is generally 0.001 mL-10 mL, preferably 0.1 mL-5 mL, per 1 mmol of compound [22].

The above-mentioned acid or scavenger may act as a solvent in this step.

The reaction temperature is generally −50° C.-150° C., preferably 10° C.-100° C.

The reaction time is generally 0.1 hr-48 hr, preferably 0.5 hr-20 hr.

[Production Method 4] and [Production Method 4A] (Losartan Production Method)

(Step 1)

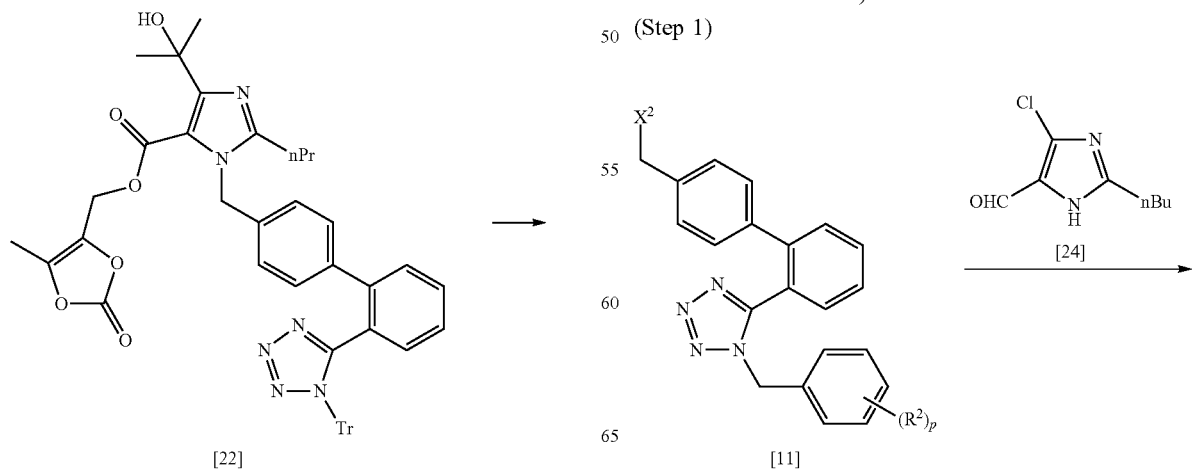

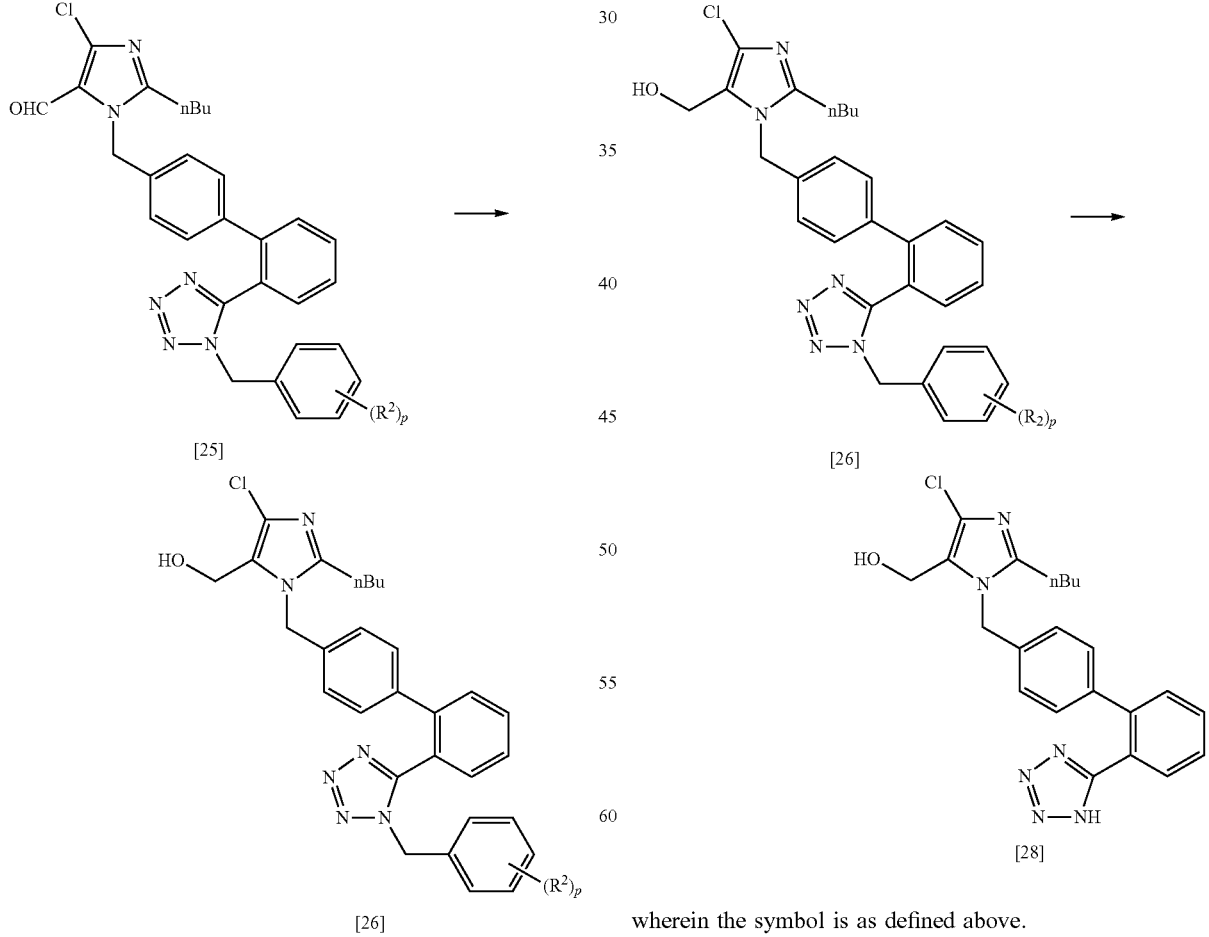

wherein the symbols are as defined above.

Compound [25] can be produced by reacting compound [11] with compound [24] in the same manner as in the method described in Production method 3, step 1.

(Step 2-A(2))

Compound [26] can be produced by reducing compound [25] by using a reducing agent. This reaction can also be performed in a solvent.

The reducing agent is not particularly limited, and reducing agents known per se can be applied. For example, sodium borohydride, lithium borohydride, zinc borohydride, sodium triacetoxyborohydride and the like can be mentioned. The amount of the reducing agent to be used is generally 1 equivalent-10 equivalents, preferably 1 equivalent-5 equivalents, relative to compound [25].

While the solvent is not particularly limited as long as the reaction proceeds, methanol, ethanol, isopropyl alcohol, dimethoxyethane, water and the like can be mentioned. The amount of the solvent to be used is generally 0.01 mL-100 mL, preferably 0.1 mL-10 mL, per 1 mmol of compound [25].

In this reaction, a base can also be used as necessary. Examples of the base include sodium hydroxide and the like. The amount of the base to be used is generally 0 equivalents-10 equivalents, preferably 1 equivalent-2 equivalents, relative to compound [25].

The reaction temperature is generally −50° C.-100° C., preferably 20° C.-50° C.

The reaction time is generally 0.01 hr-48 hr, preferably 0.1 hr-5 hr.

(Step 2-A(3))

wherein the symbol is as defined above.

Compound [28] can be produced using compound [26] by the method described in the above-mentioned Production method 1.

(Step 2-B(1))

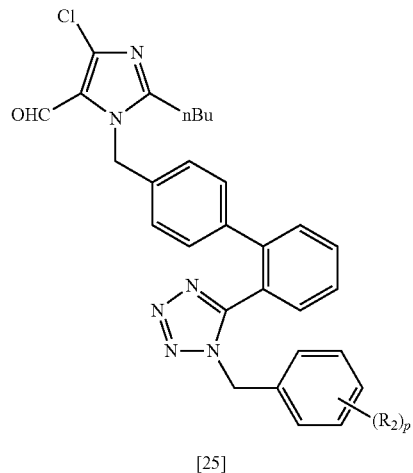

[25]

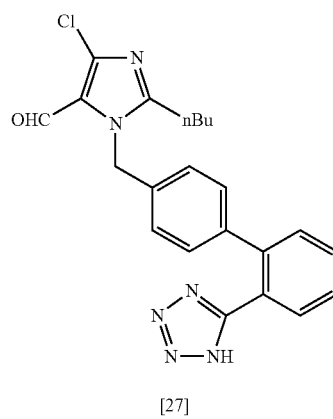

[27]

wherein the symbol is as defined above.

Compound [27] can be produced using compound [25] by the method described in the above-mentioned Production method 1.

(Step 2-B(2))

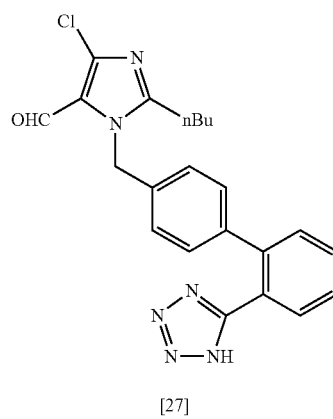

[27]

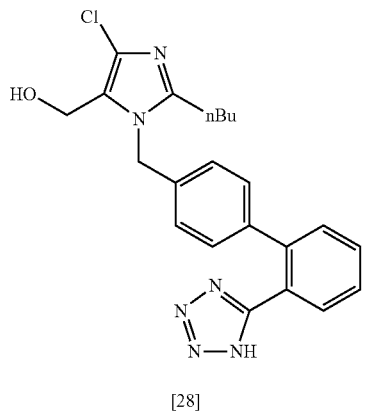

[28]

Compound [28] can be produced by reducing compound [27] in the same manner as in the method described in the above-mentioned step 2-A(1).

[Production Method 5] and [Production Method 5A] (Valsartan Production Method)

(Step 1)

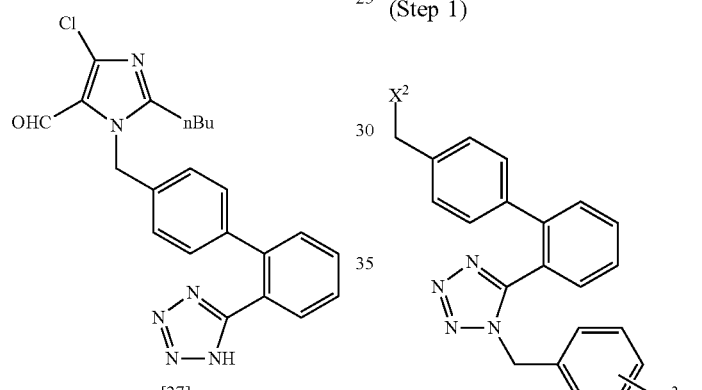

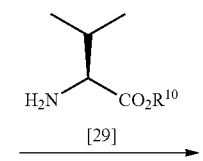

[29]

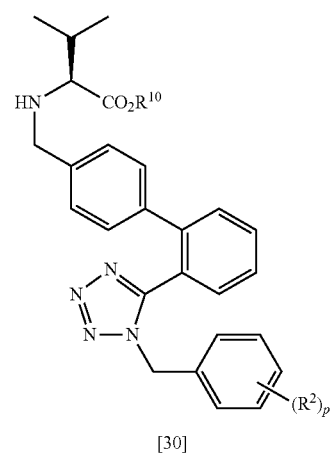

[30]

wherein $R^{10}$ is a carboxy-protecting group, and other each symbol is as defined above.

Compound [30] can be produced by reacting compound [11] with compound [29] (e.g., p-toluenesulfonate, hydrochloride etc.) in the presence of a base. This reaction can also be performed in a solvent.

R[10] of compound [29] is a carboxy-protecting group, and R[10] in step 2-A and 2-B is a protecting group not deprotected by reduction (e.g., formic acid reduction, catalytic reduction), which is preferably an alkyl group. R[10] in step 2-B is a protecting group optionally deprotected by reduction (e.g., formic acid reduction, catalytic reduction), which is preferably a benzyl group.

The base is not particularly limited, and a base known per se can be applied. For example, diisopropylethylamine, triethylamine, pyridine, sodium hydride, potassium t-butoxide and the like can be mentioned. The amount of the base to be used is generally 1 equivalent-10 equivalents, preferably 1 equivalent-5 equivalents, relative to compound [11].

The solvent is not particularly limited as long as the reaction proceeds, and acetonitrile, toluene, THF, dioxane, chloroform, methylene chloride and the like can be mentioned. The amount of the solvent to be used is generally 0.1 mL-100 mL, preferably 0.5 mL-5 mL, per 1 mmol of compound [11].

The reaction temperature is generally −50° C.-150° C., preferably 5° C.-100° C.

The reaction time is generally 0.1 hr-48 hr, preferably 0.5 hr-5 hr.

(Step 2-A)

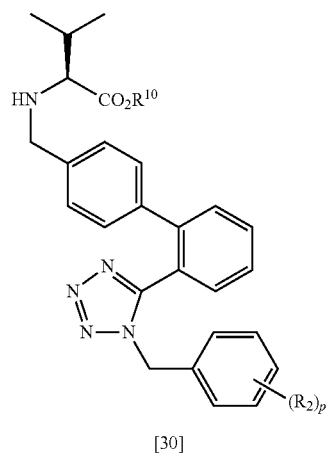

[30]

→

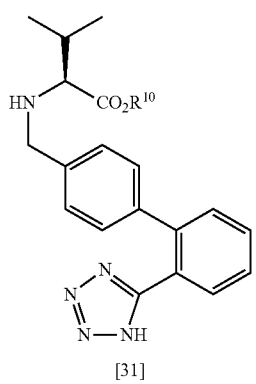

[31]

wherein the symbols are as defined above.

Compound [31] can be produced using compound [30] and in the same manner as in the method described in the above-mentioned Production method 1.

(Step 3-A)

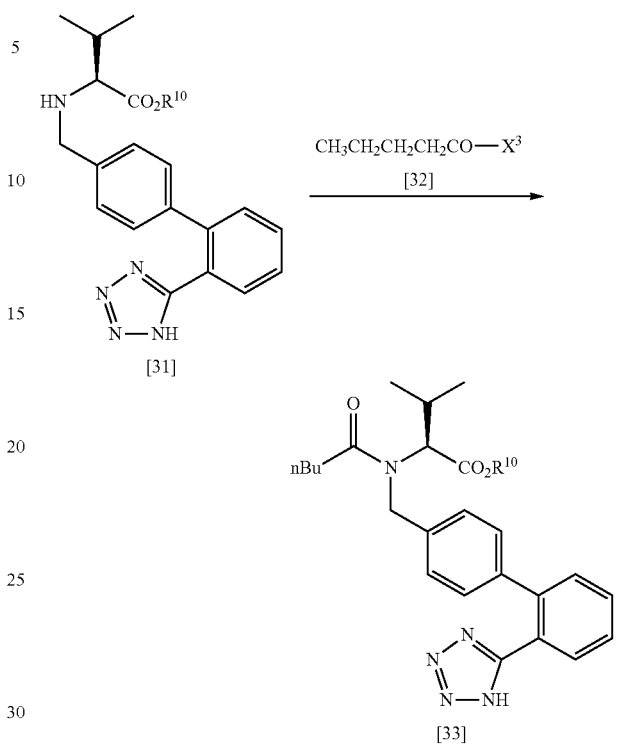

wherein $X^3$ is a leaving group, and other symbols are as defined above.

Compound [33] can be produced by reacting compound [31] with compound [32] in the presence of a base. This reaction can also be performed in a solvent.

While the base is not particularly limited, for example, triethylamine, diisopropylethylamine, DBU, sodium hydroxide, sodium carbonate, sodium hydrogen carbonate, potassium hydroxide, potassium carbonate, potassium hydrogen carbonate, potassium phosphate, 4-dimethylaminopyridine (DMAP), lutidine, pyridine and the like can be mentioned. The amount of the base to be used is generally 1 equivalent-10 equivalents, preferably 1 equivalent-3 equivalents, relative to compound [31].

While the solvent is not particularly limited as long as the reaction proceeds, toluene, xylene, methylene chloride, chloroform, acetonitrile, NMP, DMF, DMSO, THF, dimethoxyethane, t-butyl methyl ether (hereinafter to be also referred to as t-BME), 1,4-dioxane and the like can be mentioned. The amount of the solvent to be used is generally 0.001 mL-100 mL, preferably 0.1 mL-10 mL, per 1 mmol of compound [31].

The reaction temperature is generally −20° C.-150° C., preferably 0° C.-100° C.

The reaction time is generally 0.1 hr-48 hr, preferably 0.5 hr-5 hr.

(Step 4-A)

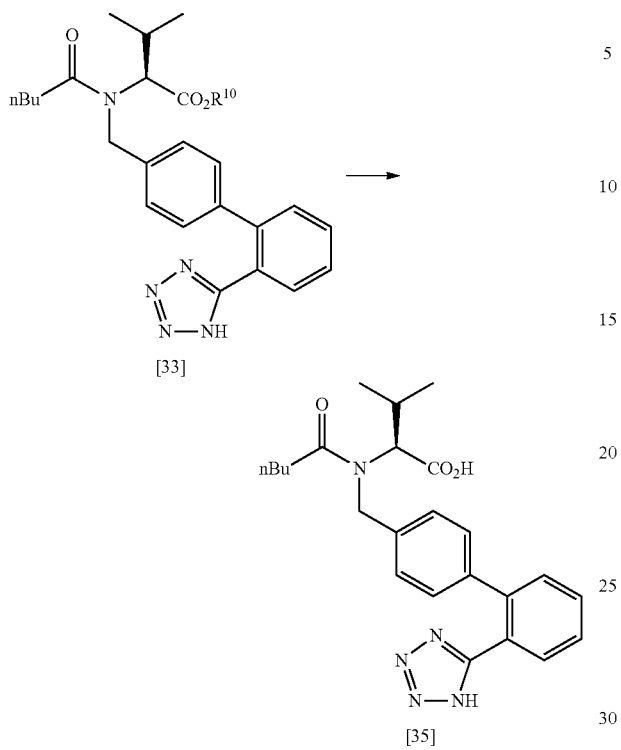

wherein the symbol is as defined above.

Compound [35] can be produced by removing $R^{10}$ of compound [33] in the presence of an acid. This reaction can also be performed in a solvent.

The acid is not particularly limited, and an acid known per se can be applied. For example, trifluoroacetic acid, trichloroacetic acid, trifluoromethanesulfonic acid, methanesulfonic acid, sulfuric acid, hydrochloric acid and the like can be mentioned. The amount of the acid to be used is generally 0.1 equivalents-1000 equivalents, preferably 1 equivalent-500 equivalents, relative to compound [33].

Deprotection by an acid can be preferably performed in the presence of a scavenger. While the scavenger is not particularly limited as long as the reaction proceeds, mercaptans such as anisole, mesitylene, 1-octanethiol and the like, and the like can be mentioned. The amount of the scavenger to be used is generally 0.001 mL-10 mL, preferably 0.1 mL-5 mL, per 1 mmol of compound [33].

The above-mentioned acid or scavenger may act as a solvent in this step.

The reaction temperature is generally −50° C.-150° C., preferably 10° C.-100° C.

The reaction time is generally 0.1 hr 48 hr, preferably 0.5 hr-5 hr.

Alternatively, compound [35] can also be produced by removing $R^{10}$ of compound [33] in the presence of a base. This reaction can also be performed in a solvent.

As the base, sodium methoxide, sodium ethoxide, dimethylamine, methylamine, ammonia, potassium carbonate, sodium carbonate and the like can be mentioned. The amount of the base to be used is generally 0.001 equivalents-10 equivalents, preferably 0.01 equivalents-1 equivalent, relative to compound [34].

The solvent is not particularly limited as long as the reaction proceeds, and methanol, ethanol, propanol and the like can be mentioned. The amount of the solvent to be used is generally 0.01 mL-100 mL, preferably 0.1 mL-10 mL, per 1 mmol of compound [34].

The reaction temperature is generally −50° C.-100° C., preferably 0° C.-20° C.

The reaction time is generally 0.001 hr-10 hr, preferably 0.1 hr-5 hr.

(Step 2-B)

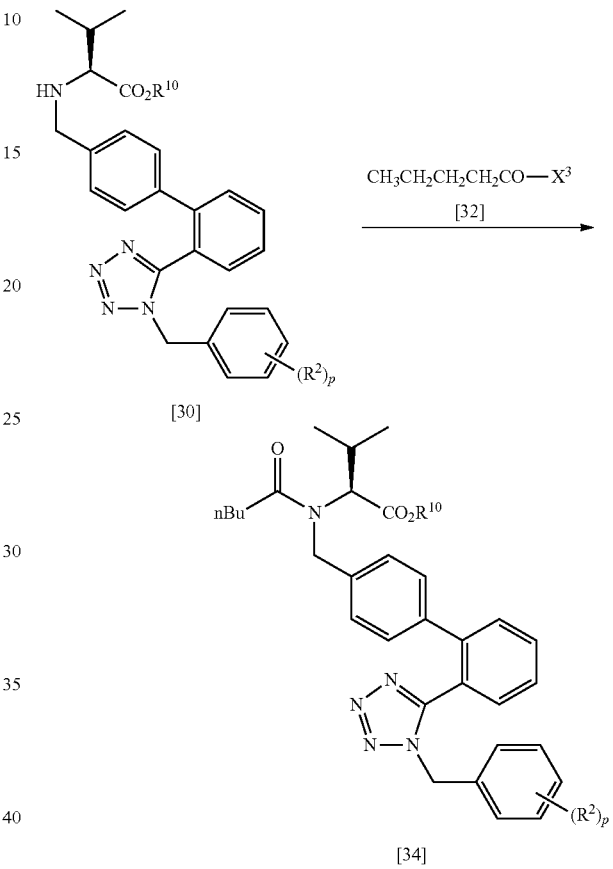

wherein the symbols are as defined above.

Compound [34] can be produced using compound [30] and compound [32] in the same manner as in the method described in the above-mentioned step 3-A.

(Step 3-B)

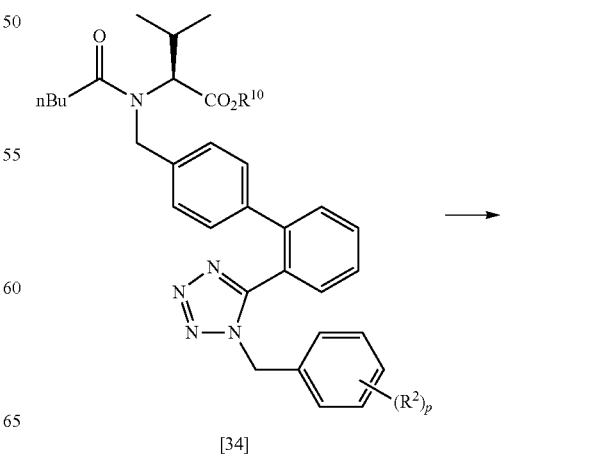

-continued

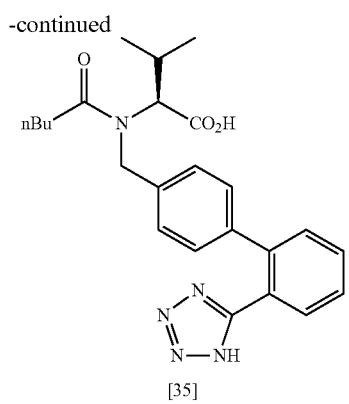

[35]

wherein the symbols are as defined above.

When $R^{10}$ is a protecting group deprotected by reduction, compound [35] can be produced using compound [34] in the same manner as in the method described in the above-mentioned Production method 1.

When $R^{10}$ is a protecting group not deprotected by reduction, compound [35] can be produced by deprotecting compound [34] in the same manner as in the method described in the above-mentioned Production method 1, removing $R^{10}$ in the same manner as in the method described in the above-mentioned step 4-A, or removing $R^{10}$ in the same manner as in the method described in the above-mentioned step 4-A and deprotecting in the same manner as in the method described in the above-mentioned Production method 1.

[Production Method 6] and [Production Method 6A] (Irbesartan Production Method)
(Step 1)

Compound [37] can be produced by reacting compound [11] with compound [36] (e.g., hydrochloride etc.) in the presence of a base or a base and an additive. This reaction can also be performed in a solvent.

While the base is not particularly limited, for example, triethylamine, ethyldiisopropylamine, DBU, sodium hydroxide, sodium carbonate, sodium hydrogen carbonate, potassium hydroxide, potassium carbonate, potassium hydrogen carbonate, potassium phosphate, 4-dimethylaminopyridine (DMAP) and lutidine can be mentioned. The amount of the base to be used is generally 1 equivalent-10 equivalents, preferably 1 equivalent-3 equivalents, relative to compound [11].

As the additive, tetraalkylammonium halide (e.g., tetrabutylammonium bromide), tetraalkylphosphonium halide and the like can be mentioned. The amount of the additive to be used is generally 0.01 equivalents-10 equivalents, preferably 0.05 equivalents-1 equivalent, relative to compound [11].

While the solvent is not particularly limited as long as the reaction proceeds, toluene, xylene, methylene chloride, chloroform, acetonitrile, DMF, DMSO, THF, dimethoxyethane, t-BME, 1,4-dioxane and the like and a mixture of the above-mentioned solvent and water can be mentioned. The amount of the solvent to be used is generally 0.001 mL-100 mL, preferably 0.1 mL-10 mL, per 1 mmol of compound [11].

The reaction temperature is generally −20° C.-150° C., preferably 0° C.-100° C.

The reaction time is generally 0.1 hr-48 hr, preferably 0.5 hr-10 hr.
(Step 2)

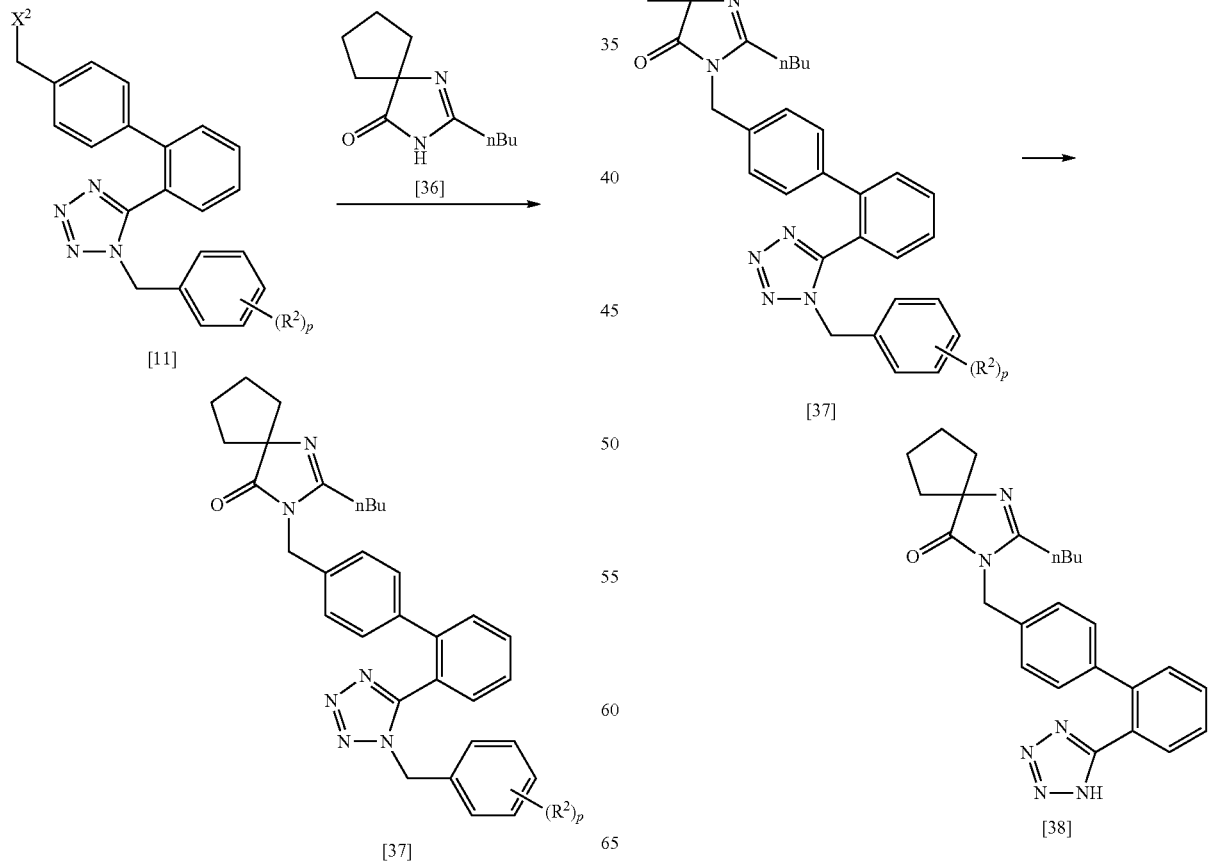

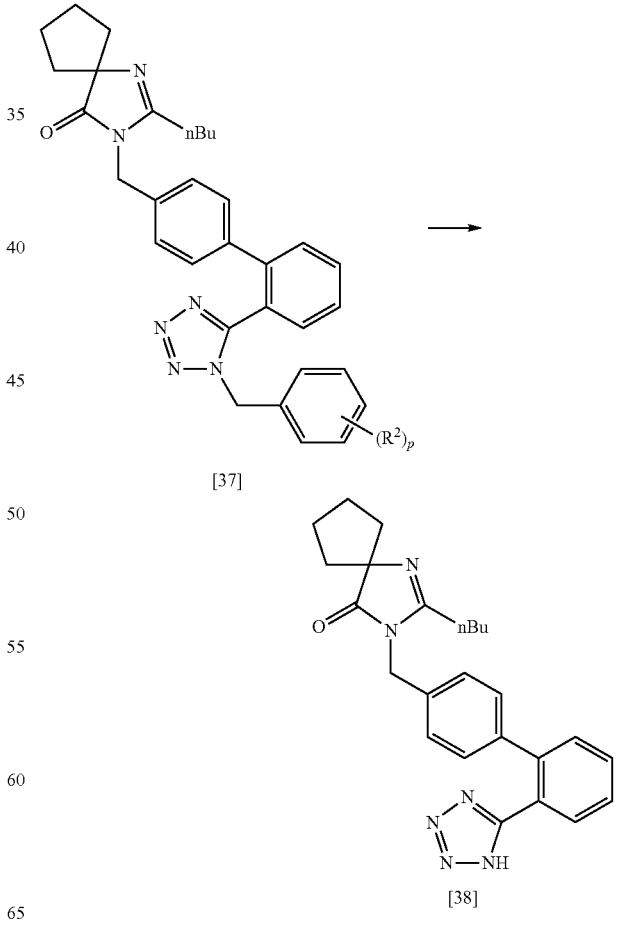

wherein the symbol is as defined above.

wherein the symbol is as defined above.

Compound [38] can be produced using compound [37] and in the same manner as in the methods described in the above-mentioned Production method 1.

[Production Method 7] and [Production Method 7A] (Candesartan Cilexetil Production Method)

(Step 1-A-i)

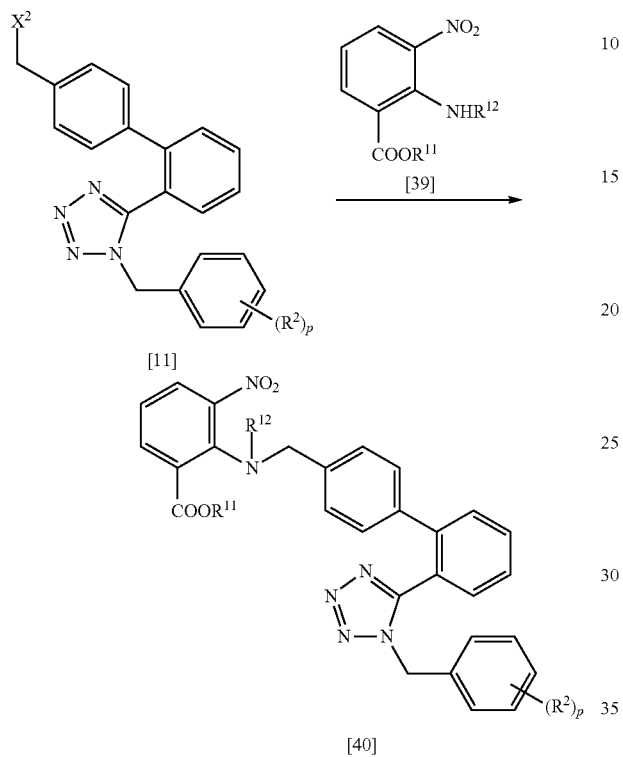

[40]

wherein $R^{11}$ is a carboxy-protecting group, $R^{12}$ is an amino-protecting group, and other each symbol is as defined above.

Compound [40] can be produced by reacting compound [11] with compound [39] in the presence or absence of a base. This reaction can also be performed in a solvent.

This reaction is preferably performed in the presence of a base. As such base, metal hydrides such as sodium hydride and the like, metal alkoxides such as sodium t-butoxide, potassium t-butoxide and the like, carbonates such as potassium carbonate, potassium hydrogen carbonate, sodium carbonate, sodium hydrogen carbonate and the like, and the like can be mentioned. Of these, carbonate, particularly, potassium carbonate, is preferably used. The amount of the base to be used is generally 1 equivalent-5 equivalents relative to compound [11].

As the solvent, aprotic polar solvents such as dimethylformamide, dimethyl sulfoxide, dimethylacetamide and the like, ketones such as acetone, ethylmethylketone and the like, ethers such as tetrahydrofuran, dioxane and the like, esters such as ethyl acetate and the like, aromatic hydrocarbons such as benzene, toluene, xylene and the like, hydrocarbon halides such as dichloromethane, chloroform, carbon tetrachloride, dichloroethane and the like, acetonitrile and the like can be mentioned. Of these, acetonitrile is preferably used. The amount of the solvent to be used is generally 0.1 mL-10 mL per 1 mmol of compound [11].

The reaction temperature is generally 70° C.-90° C., and the reaction time is 3 hr-10 hr.

(Step 1-A-ii)

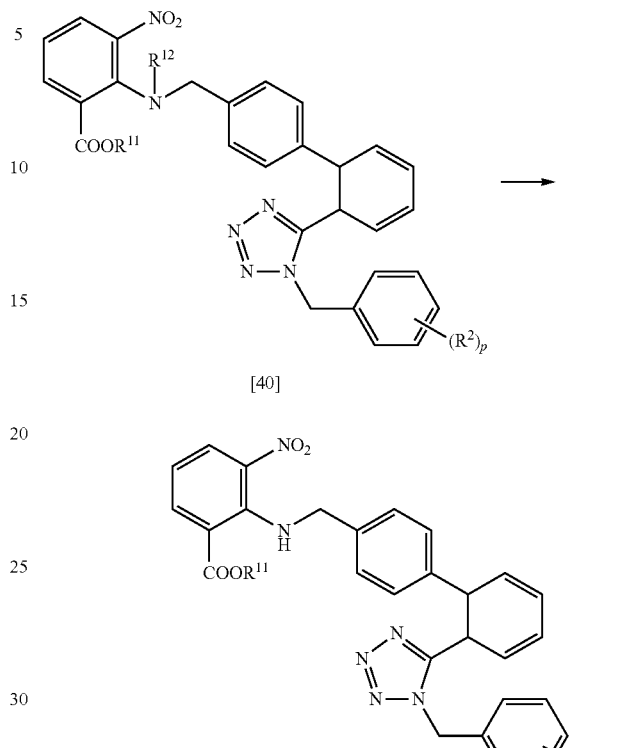

wherein the symbols are as defined above.

Compound [41] can be produced by removing $R^{12}$ of compound [40] in the presence of an acid.

While the acid is not particularly limited, an acid known per se can be applied. For example, Brønsted acid (e.g., trifluoromethanesulfonic acid, methanesulfonic acid, phosphoric acid, sulfuric acid, hydrochloric acid etc.) or Lewis acid (e.g., aluminum chloride, tin chloride, boron fluoride diethyl ether etc.) can be mentioned. The amount of the acid to be used is generally 0.1 equivalents-1000 equivalents, preferably 1 equivalent-500 equivalents, relative to compound [40].

While the solvent is not particularly limited as long as the reaction proceeds, water, methanol, ethanol, isopropyl alcohol, tetrahydrofuran, dimethoxyethane, methyl t-butyl ether and the like can be mentioned. The amount of the solvent to be used is generally 0.01 mL-100 mL, preferably 0.1 mL-10 mL, per 1 mmol of compound [40].

The reaction temperature is generally −50° C.-150° C., preferably 10° C.-100° C.

The reaction time is generally 0.1 hr-48 hr, preferably 0.5 hr-20 hr.

(Step 1-A-iii)

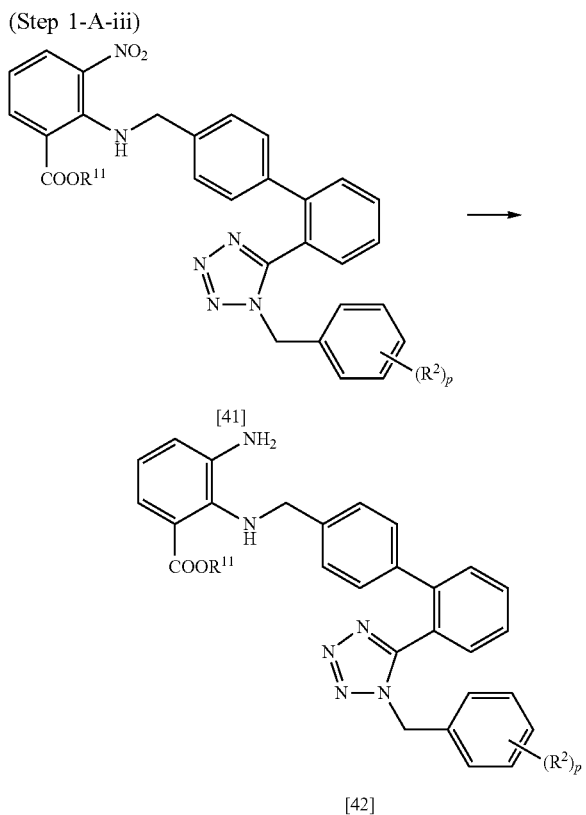

[41]

[42]

wherein the symbols are as defined above.

Compound [42] can be produced by reducing compound [41] with a reducing agent. This reaction can also be performed in a solvent.

While the reducing agent is not particularly limited, a reducing agent known per se can be applied. For example, tin chloride, sodium borohydride, lithium borohydride, boron zinc borohydride, sodium triacetoxyborohydride and the like can be mentioned. The amount of the reducing agent to be used is generally 1 equivalent-10 equivalents, preferably 1 equivalent-5 equivalents, relative to compound [41].

While the solvent is not particularly limited as long as the reaction proceeds, water, methanol, ethanol, isopropyl alcohol, dimethoxyethane, methyl t-butyl ether and the like can be mentioned. The amount of the solvent to be used is generally 0.01 mL-100 mL, preferably 0.1 mL-10 mL, per 1 mmol of compound [41].

The reaction temperature is generally −50° C.-100° C., preferably 20° C.-50° C.

The reaction time is generally 0.01 hr-48 hr, preferably 0.1 hr-5 hr.

(Step 1-A-iv)

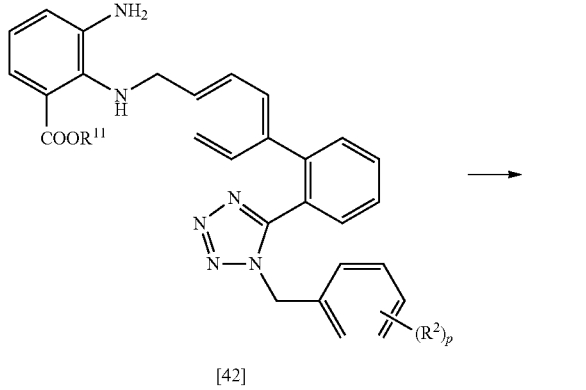

[42]

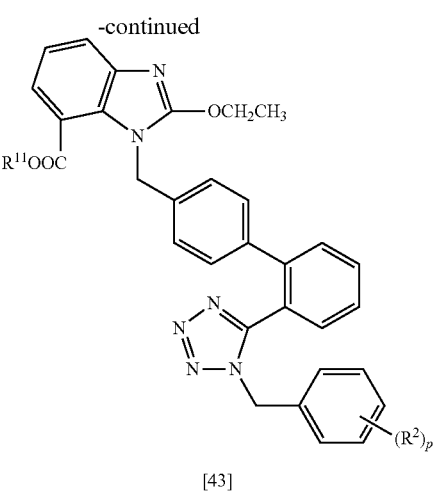

[43]

wherein the symbols are as defined above.

Compound [43] can be produced by reacting compound [42] with tetraethoxymethane in the presence or absence of a solvent.

While the solvent is not particularly limited as long as the reaction proceeds, ethanol, tetrahydrofuran, toluene, ethyl acetate, acetic acid, dimethoxyethane, t-butyl methyl ether and the like can be mentioned.

The reaction temperature is generally 0° C.-120° C., preferably 50° C.-100° C.

The reaction time is generally 0.01 hr-48 hr, preferably 0.1 hr-5 hr.

(Step 1-B)

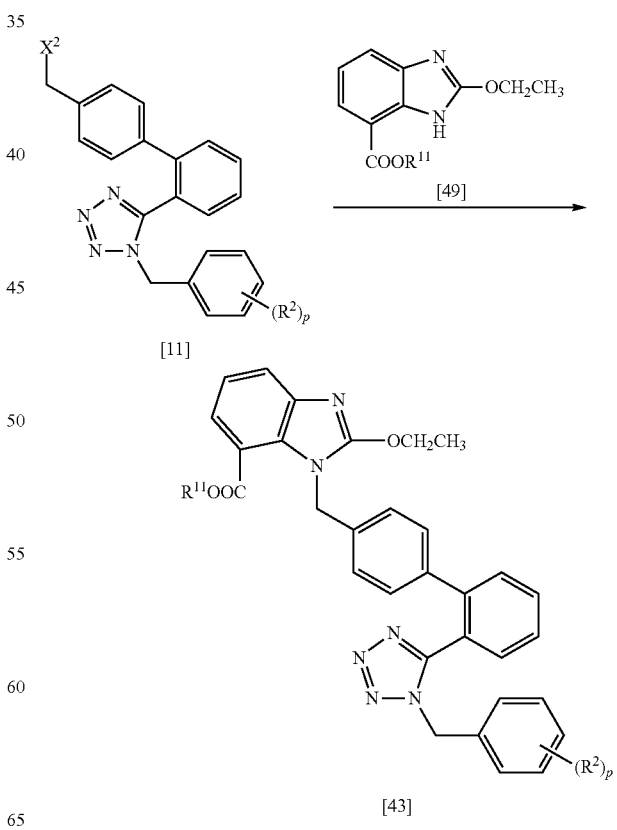

[11]

[49]

[43]

wherein the symbols are as defined above.

Compound [43] can be produced by reacting compound [11] with compound [49] in the presence of a base. This reaction can also be performed in a solvent.

The base is not particularly limited and, for example, potassium carbonate, potassium hydrogen carbonate, potassium phosphate, sodium hydroxide, sodium carbonate, sodium hydrogen carbonate, potassium hydroxide, triethylamine, diisopropylethylamine, DBU, 4-dimethylaminopyridine (DMAP), lutidine, alkali metal salts of carboxylic acid such as sodium acetate, potassium acetate and the like, zinc salts or magnesium salts of carboxylic acid such as zinc acetate, magnesium acetate and the like, alkali metal salts, magnesium salts or zinc salts of phosphate such as potassium salt of bis(2-ethylhexyl)phosphoric acid and the like, alkali metal salts, magnesium salts or zinc salts of sulfonic acid such as potassium n-dodecylsulfonate and the like, and the like can be mentioned. The amount of the base to be used is generally 1 equivalent-10 equivalents, preferably 1 equivalent-3 equivalents, relative to compound [11].

The solvent is not particularly limited as long as the reaction proceeds, and DMA, methanol, ethanol, propanol, toluene, xylene, methylene chloride, chloroform, acetonitrile, DMF, DMSO, NMP, THF, dimethoxyethane, t-butyl methyl ether, 1,4-dioxane, water and the like, and a mixed solvent of two or more kinds selected therefrom can be mentioned. The amount of the solvent to be used is generally 0.001 mL-100 mL, preferably 0.1 mL-10 mL, per 1 mmol of compound [11].

The reaction temperature is generally −20° C.-150° C., preferably 10° C.-40° C.

The reaction time is generally 0.1 hr-48 hr, preferably 0.5 hr-36 hr.

(Step 2)

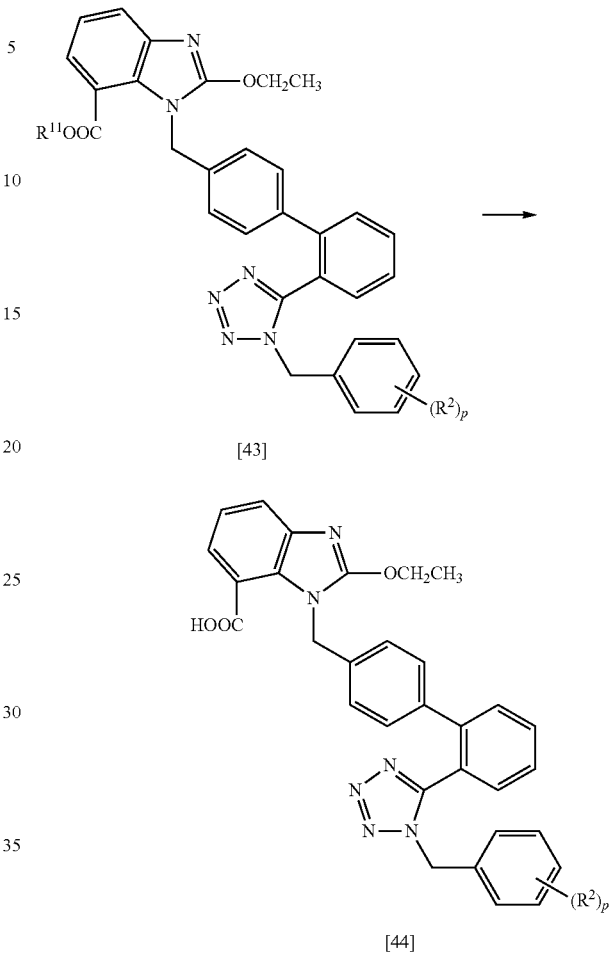

wherein the symbols are as defined above.

Compound [44] can be produced using compound [43] and in the same manner as in the method described in the above-mentioned Production method 5, step 4-A. Furthermore, compound [44] may be purified by crystallization as alkylamine salt such as dicyclohexylamine and the like.

(Step 3)

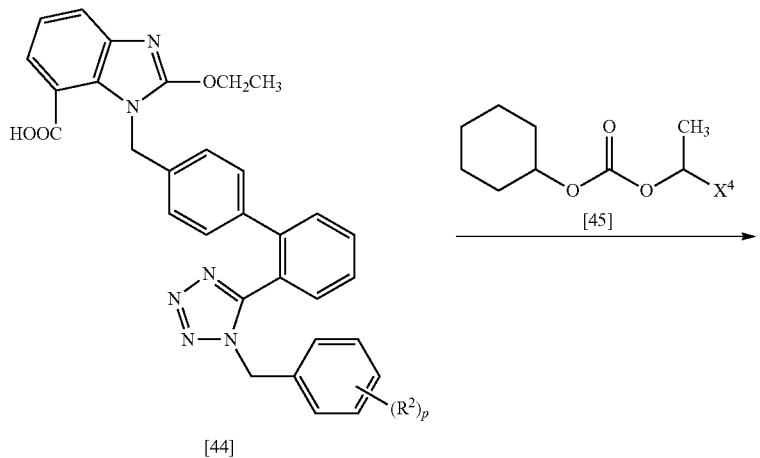

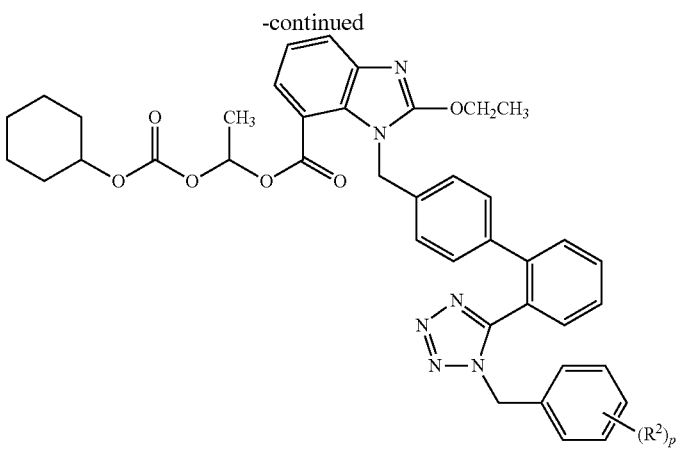

[46]

wherein $X^4$ is a leaving group or a hydroxyl group, and other each symbol is as defined above.

Compound [46] can be produced by reacting compound [44] or an amine salt thereof with compound [45] in the presence or absence of a base. This reaction can also be performed in a solvent.

The base is not particularly limited, and a base known per se can be applied. For example, sodium hydroxide, potassium hydroxide, sodium carbonate, potassium carbonate, sodium hydrogen carbonate, potassium hydrogen carbonate, triethylamine, tributylamine, methylamine, dimethylamine can be mentioned. The amount of the base to be used is generally 0.1 equivalents-10 equivalents relative to compound [44].

The solvent is not particularly limited as long as the reaction proceeds, and methanol, ethanol, isopropyl alcohol, dimethylformamide and the like can be mentioned. The amount of the solvent to be used is generally 0.01 mL-100 mL, preferably 0.1 mL-10 mL, per 1 mmol of compound [44].

The reaction temperature is generally −50° C.-150° C., preferably 10° C.-100° C.

The reaction time is generally 0.1 hr-48 hr, preferably 0.5 hr-20 hr.

(Step 4)

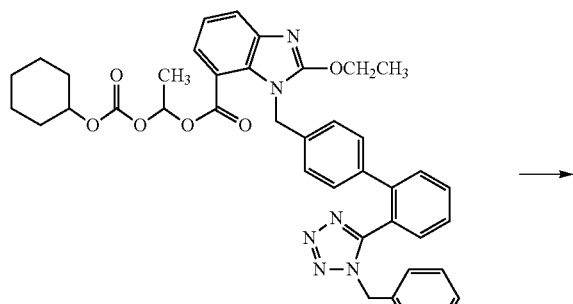

[46]

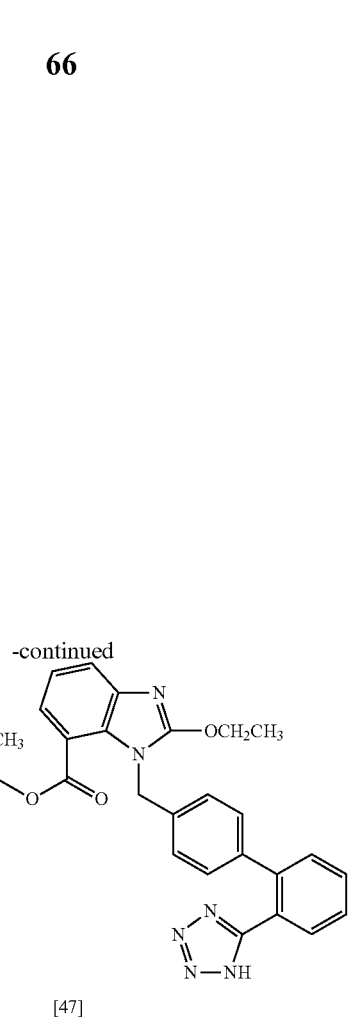

[47]

wherein the symbol is as defined above.

Compound [47] can be produced using compound [46] in the same manner as in the method described in the above-mentioned Production method 1.

The salt of compound [11] is not particularly limited and, for example, salts with hydrochloric acid, sulfuric acid and the like can be mentioned.

The salt of compound [23], compound [28], compound [35], compound [38] or compound [47] is not particularly limited as long as it is pharmacologically acceptable and, for example, salts with mineral acids such as hydrochloric acid, sulfuric acid, hydrobromic acid, phosphoric acid and the like;
salts with organic acids such as methanesulfonic acid, p-toluenesulfonic acid, acetic acid, oxalic acid, citric acid, malic acid, fumaric acid and the like;
salts with alkali metals such as sodium, potassium and the like;
salts with alkaline earth metals such as magnesium and the like;
salts with amines such as ammonia, ethanolamine, 2-amino-2-methyl-1-propanol and the like can be mentioned.

Compound [23], compound [28], compound [35], compound [38], compound [47], and salts thereof include solvates. Examples of the solvate include hydrate and alcohol solvates (e.g., methanol solvate, ethanol solvate).

EXAMPLES

The present invention is specifically explained in the following by referring to Reference Examples and Examples, which are not to be construed as limitative.

In the following Reference Example and Examples, "room temperature" means 15° C.-30° C.

In the following Reference Examples and Examples, "%" of the concentrations and contents means "wt %" unless particularly indicated.

In the following Reference Examples and Examples, "vol" used for solvents means the amount (volume) per 1 g of substrate.

Abbreviations in the Examples show the following compounds.
HBT: 1-benzyl-5-phenyltetrazole
BAC: [2'-(1-benzyl-1H-tetrazol-5-yl)biphenyl-4-yl]methylacetate
BBA: p-bromobenzylacetate
BAL: [2'-(1-benzyl-1H-tetrazol-5-yl)biphenyl-4-yl]methanol
BBR: 1-benzyl-5-[4'-(bromomethyl)biphenyl-2-yl]-1H-tetrazole
VB: benzyl N-({2'-[1-benzyl-1H-tetrazol-5-yl]biphenyl-4-yl}methyl)-L-valinate
VBV: benzyl N-({2'-[1-benzyl-1H-tetrazol-5-yl]biphenyl-4-yl}methyl)-N-pentanoyl-L-valinate
CPI: 2-butyl-1,3-diazaspiro[4.4]non-1-en-4-one hydrochloride
IAL: 2-butyl-4-chloroimidazole-5-carbaldehyde
BIR: 3-[2'-(1-benzyl-1H-tetrazol-5-yl)biphenyl-4-yl]-2-butyl-1,3-diazaspiro[4.4]non-1-en-4-one
LALD: 2-butyl-4-chloro-1-({2'-[1-benzyl-1H-tetrazol-5-yl]biphenyl-4-yl}methyl)imidazole-5-carbaldehyde
LAL: 2-butyl-4-chloro-1-{[2'-(1-benzyl-1H-tetrazol-5-yl)biphenyl-4-yl]methyl}imidazole-5-methanol
BCAN: 1-(cyclohexyloxycarbonyloxy)ethyl 2-ethoxy-1-[[2'-(1H-tetrazol-5-yl)biphenyl-4-yl]methyl]benzoimidazole-7-carboxylate
IME: ethyl 4-(1-hydroxy-1-methylethyl)-2-propyl-imidazole-5-carboxylate
BIA: ethyl 4-(1-hydroxy-1-methylethyl)-2-propyl-1-[[2'-[1-benzyl-1H-tetrazol-5-yl]biphenyl-4-yl]methyl]imidazole-5-carboxylate
BIH: ethyl 4-(1-hydroxy-1-methylethyl)-2-propyl-1-[[2'-[1H-tetrazol-5-yl]biphenyl-4-yl]methyl]imidazole-5-carboxylate
BIT: ethyl 4-(1-hydroxy-1-methylethyl)-2-propyl-1-[[2'-[1-(triphenylmethyl)-1H-tetrazol-5-yl]biphenyl-4-yl]methyl]imidazole-5-carboxylate
BIC: potassium 4-(1-hydroxy-1-methylethyl)-2-propyl-1-[[2'-[1-(triphenylmethyl)-1H-tetrazol-5-yl]biphenyl-4-yl]methyl]imidazole-5-carboxylate
OXC: 4-(chloromethyl)-5-methyl-2-oxo-1,3-dioxol
TOLM: (5-methyl-2-oxo-1,3-dioxol-4-yl)methyl 4-(1-hydroxy-1-methylethyl)-2-propyl-1-[[2'-[1-(triphenylmethyl)-1H-tetrazol-5-yl]biphenyl-4-yl]methyl]imidazole-5-carboxylate
BME: 1-benzyl-5-(4'-methylbiphenyl-2-yl)-1H-tetrazole
BBB: p-bromobenzylbenzoate
BBZ: 1-benzyl-5-[4'-(benzoyloxymethyl)biphenyl-2-yl]-1H-tetrazole
OLM: 4-(1-hydroxy-1-methylethyl)-2-propyl-1-[[2'-(1H-tetrazol-5-yl)biphenyl-4-yl]methyl]imidazole-5-carboxylic acid
OLM MDX: (5-methyl-2-oxo-1,3-dioxol-4-yl)methyl 4-(1-hydroxy-1-methylethyl)-2-propyl-1-[[2'-(2H-tetrazol-5-yl)biphenyl-4-yl]methyl]imidazole-5-carboxylate
BVAL: benzyl N-{4-[2-(1-benzyl-1H-tetrazole-5-yl)phenyl]benzyl}-N-valeryl-L-valinate
VAL: N-{4-[2-(1H-tetrazol-5-yl)phenyl]benzyl}-N-valeryl-L-valine
VM: methyl N-[[2'-benzyl-1H-tetrazol-5-yl][1,1'-biphenyl]-4-yl]methyl]-L-valinate
BMVAL: methyl N-{4-[2-(1-benzyl-1H-tetrazol-5-yl)phenyl]benzyl}-N-valeryl-L-valinate
MVAL: methyl N-{4-[2-(1H-tetrazol-5-yl)phenyl]benzyl}-N-valeryl-L-valinate
IR: 2-butyl-3-{4-[2-(1H-tetrazol-5-yl)phenyl]benzyl}-1,3-diazaspiro[4.4]non-1-en-4-one
LOS: 2-butyl-4-chloro-1-{[2'-(1H-tetrazol-5-yl)biphenyl-4-yl]methyl}imidazole-5-methanol
CAN: (1RS)-1-(cyclohexyloxycarbonyloxy)ethyl 2-ethoxy-1-{[2'-(1H-tetrazol-5-yl)biphenyl-4-yl]methyl}-1H-benzo[d]imidazole-7-carboxylate
BIM: methyl 2-ethoxy-1H-benzimidazole-7-carboxylate
CBCA: 2-ethoxy-1-[2'-[1-benzyl-1H-tetrazol-5-yl]biphenyl-4-yl]-1H-benzimidazole-7-carboxylic acid
CV: 2-ethoxy-1-{[2'-(1H-tetrazol-5-yl)biphenyl-4-yl]methyl}-1H-benzo[d]imidazole-7-carboxylic acid
CBME: methyl 2-ethoxy-1-[2'-[1-benzyl-1H-tetrazol-5-yl]biphenyl-4-yl]-1H-benzimidazole-7-carboxylate
DPOLM: (5-methyl-2-oxo-1,3-dioxol-4-yl)methyl 4-(1-hydroxy-1-methylethyl)-2-propyl-1-[[2'-[2-(2,4-dimethoxybenzyl)-2H-tetrazol-5-yl]biphenyl-4-yl]methyl]imidazole-5-carboxylate Reference Example 1

Synthesis of BBR

1. BME

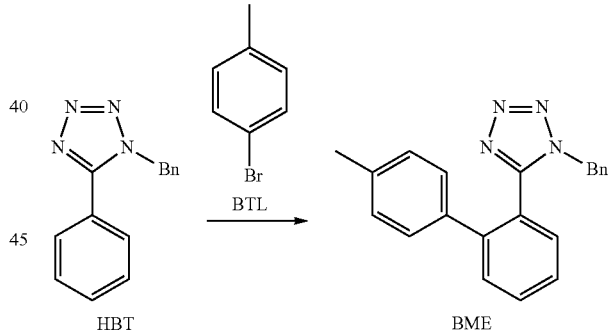

A mixture of triphenylphosphine (0.355 g, 1.35 mmol), 1-benzyl-5-phenyl-1H-tetrazole (HBT, 10 g, 42.3 mmol), potassium carbonate (5.85 g, 42.3 mmol), potassium bis(2-ethylhexyl)phosphate NMP solution (2.5 wt %, 19.46 mL, 1.35 mmol), p-bromotoluene (BTL, 7.96 g, 46.6 mmol) and N-methyl-2-pyrrolidone (50 mL) was heated under a nitrogen atmosphere to 138° C., dichloro(p-cymene)ruthenium (II) dimer (0.207 g, 0.338 mmol as monomer) was added and the mixture was stirred at the same temperature for 12 hr. The reaction mixture was cooled, and mixed with water (20 mL) and t-butyl methyl ether (40 mL). The aqueous layer was extracted with t-butyl methyl ether (40 mL×2), and the organic layers were combined and washed with water (40 mL×2) and brine (20 mL), dried over sodium sulfate, and concentrated under reduced pressure to give a crude product of BME (14.0 g, 101.4% of theoretical yield) as a dark brown oil. t-Butyl methyl ether (6 mL) was added to 2 g of this product to allow for crystallization, and the obtained solid was filtered to give 1-benzyl-5-(4'-methylbiphenyl-2-yl)-1H-tetrazole (BME, 1.5 g, yield 76%).

melting point: 140° C.;

IR (KBr): $\nu_{max}$=1455, 1093 cm$^{-1}$;

$^1$H NMR (CDCl$_3$): δ=7.61 (dt, J=8.0, 1.6 Hz, 1H), 7.56 (dd, J=7.8, 0.8 Hz, 1H), 7.39 (dt, J=7.8, 1.2 Hz, 1H), 7.33 (dd, J=7.8, 1.2 Hz, 1H), 7.22-7.08 (m, 5H), 7.03 (d, J=8.4 Hz, 2H), 6.75 (d, J=7.2 Hz, 2H), 4.76 (s, 2H), 2.34 (s, 3H);

$^{13}$C NMR (CDCl$_3$): δ=154.5, 141.4, 137.7, 135.6, 132.9, 131.3, 130.9, 129.9, 129.4, 128.4, 128.2, 127.6, 127.3, 122.3, 50.5, 20.8;

HRMS: [M+Na]$^+$ calcd for C$_{21}$H$_{18}$N$_4$Na, 349.1429. found 349.1425.

Mass (M+H): 327.0 amu;

HPLC Purity (Area %): 99.3.

2. BBR

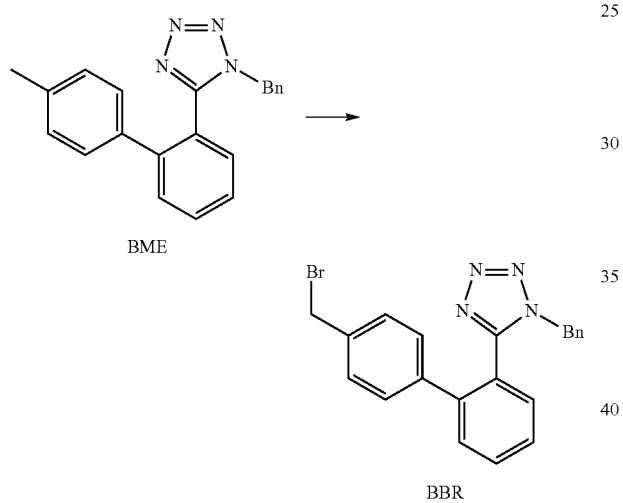

1-Benzyl-5-(4'-methylbiphenyl-2-yl)-1H-tetrazole (BME, 1.0 g, 3.06 mmol) was dissolved in ethyl acetate (4 mL), 1,3-dibromo-5,5-dimethylhydantoin (DBDMH, 0.86 g, 3 mmol) and 2,2'-azobisisobutyronitrile (AIBN, 15 mg, 0.091 mmol) were added, and the mixture was heated under reflux for 6 hr. Crude 1-benzyl-5-(4'-bromomethylbiphenyl-2-yl)-1H-tetrazole (BBR) was produced at a conversion ratio of about 40%. Purification by silica gel column chromatography gave BBR.

melting point: 70.9° C.;

IR (neat): 1603 cm$^{-1}$;

$^1$H NMR (CDCl$_3$): δ=7.65 (td, J=7.5, 1.5 Hz, 1H), 7.57 (dd, J=7.5, 1.5 Hz, 1H), 7.45 (td, J=7.9, 1.4 Hz, 1H), 7.35 (dd, J=7.9, 1.4 Hz, 1H), 7.31 (d, J=8.2 Hz, 2H), 7.22 (t, J=8.2 Hz, 1H), 7.17 (t, J=8.2 Hz, 2H), 7.10 (2H, J=8.2 Hz, 2H), 6.77 (d, J=8.2 Hz, 2H), 4.82 (s, 2H), 4.46 (s, 2H).

$^{13}$C NMR (CDCl$_3$): δ=154.0, 140.3, 139.2, 137.9, 133.0, 131.9, 131.0, 130.2, 129.0, 128.7, 128.6, 128.4, 128.3, 122.4, 50.9, 31.7.

MS: 405 [M+H]$^+$.

HRMS: Calcd for C$_{21}$H$_{17}$BrN$_4$, 427.0534 [M+Na]$^+$. Found 427.0536 [M+Na]$^+$.

Example 1-1

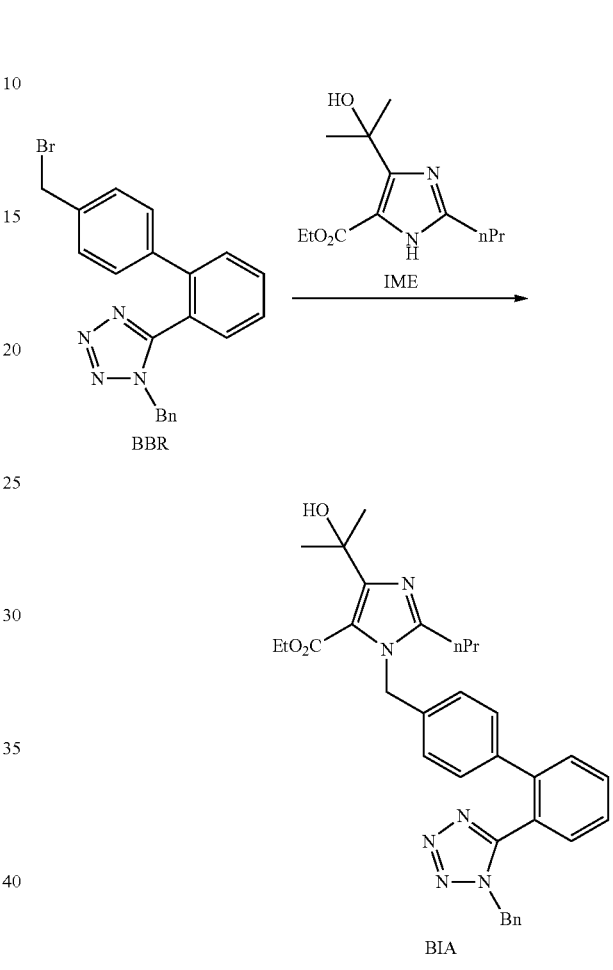

A mixture of IME (5 g, 21.0 mmol), BBR (9.05 g, 22.3 mmol), potassium carbonate (5.1 g, 37.4 mmol) and acetonitrile (50 mL, 10 vol) was stirred at 84° C. for 18 hr. The conversion yield of this reaction was 92.68%. The reaction mixture was filtered through celite, and ethyl acetate was added. The mixture was washed with 2% hydrochloric acid and saturated brine, dried over sodium sulfate, and concentrated under reduced pressure to give BIA (9.78 g, yield 83.2%).

melting point: 88° C.-91° C.;

IR (KBr): $\nu_{max}$=3416, 2967, 1702, 1466, 1218, 1172 cm$^{-1}$;

$^1$H NMR (CDCl$_3$): δ=7.64 (dt, J=15.3, 7.6, 1.2 Hz, 1H), 7.50 (dd, J=7.6, 1.2 Hz, 1H), 7.43 (dt, J=15.3, 7.6, 1.2 Hz, 1H), 7.31 (dd, J=7.6, 1.2 Hz, 1H), 7.27-7.20 (m, 1H), 7.08 (d, J=8.2 Hz, 2H), 6.83 (d, J=8.2 Hz, 2H), 6.78 (d, J=8.0 Hz, 2H), 5.42 (s, 2H), 4.82 (s, 2H), 4.20 (q, J=7.2 Hz, 2H), 2.63 (t, J=7.6 Hz, 2H), 1.75-1.64 (m, 2H), 1.61 (s, 6H), 1.15 (t, J=7.2 Hz, 3H), 0.97 (t, J=7.2 Hz, 3H).

Example 1-2(a)

Deprotection

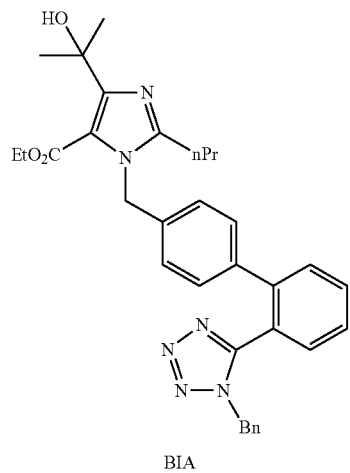
BIA

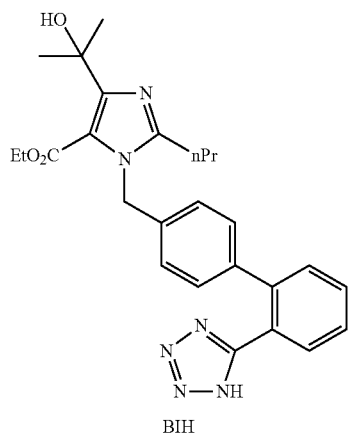
BIH

A mixture of BIA (0.3 g, 0.53 mmol), ammonium formate (0.16 g, 2.58 mmol), 5% Pd—BaSO₄ (0.057 g, 5 mol %), isopropyl alcohol (3 mL, 10 vol) and water (1.8 mL, 6 vol) was stirred at 55° C. for 11 hr. The conversion yield of this reaction was 93.1%. The reaction mixture was filtered, the filtrate was concentrated, and the concentrated residue was purified by silica gel column chromatography (2-3% methanol/methylene chloride) to give the object compound (211 mg, yield 84.3%).

IR (KBr) $v_{max}$=1706, 1604, 1273 cm$^{-1}$;

$^1$H NMR (CDCl$_3$): δ=7.91 (d, J=7.6 Hz, 1H), 7.60-7.52 (m, 2H), 7.42 (d, J=7.6 Hz, 1H), 7.12 (d, J=8.75 Hz, 2H), 6.81 (d, J=8 Hz, 2H), 5.40 (s, 2H), 4.18 (q, J=7.2 Hz, 2H), 2.38 (t, J=7.2 Hz, 2H), 1.70-1.65 (m, 2H), 1.45 (s, 6H), 1.25 (s, 1H), 1.13 (t, J=7.2 Hz, 3H), 0.91 (t, J=7.6 Hz, 3H)

$^{13}$C NMR (CDCl$_3$): δ=161.6, 158.5, 155.5, 151.6, 140.8, 138.9, 136.4, 131.2, 130.8, 130.5, 129.6, 128.1, 125.3, 123.5, 117.1, 70.5, 61.7, 48.9, 29.0, 28.7, 21.7, 13.8;

Mass: 475 [M+H]$^+$.

Example 1-2(b)

Deprotection

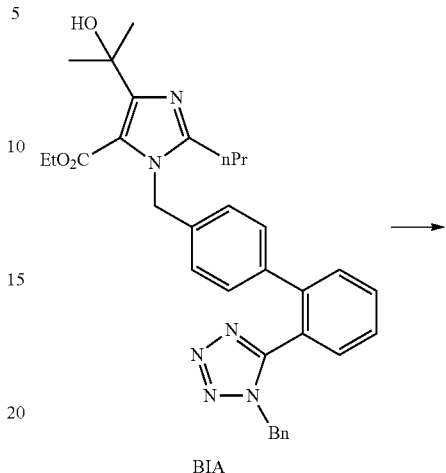
BIA

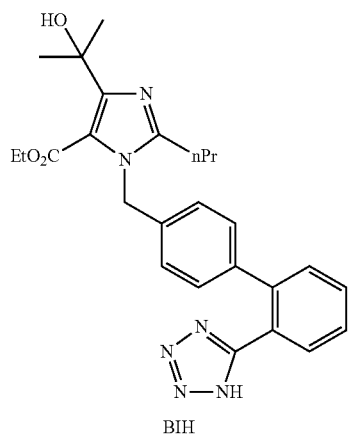
BIH

A mixture of BIA (0.1 g, 0.17 mmol), sodium formate (0.092 g, 0.86 mmol), 5% Pd—BaSO₄ (0.019 g, 5 mol %), isopropyl alcohol (1 mL, 10 vol) and water (0.6 mL, 6 vol) was stirred at 55° C. for 4 hr. The conversion yield of this reaction was 91.16%.

Example 1-2(c)

Deprotection

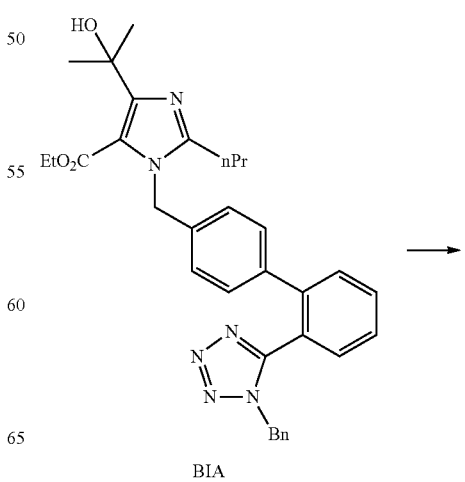
BIA

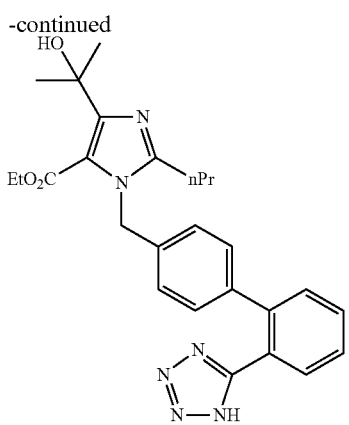

BIH

A mixture of BIA (0.1 g, 0.17 mmol), ammonium formate (0.055 g, 0.86 mmol), 5% Pd—CaCO₃ (0.019 g, 5 mol %), isopropyl alcohol (1 mL, 10 vol) and water (0.6 mL, 6 vol) was stirred at 55° C. for 9 hr. The conversion yield of this reaction was 90.44%.

Example 1-3

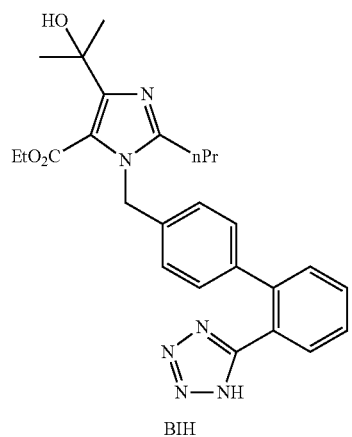

BIH

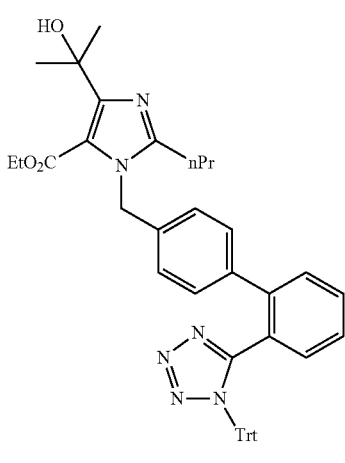

BIT

To a mixture of BIH (0.656 g, 1.38 mmol), triethylamine (0.22 mL, 1.52 mmol) and methylene chloride (7.8 mL, 12 vol) was added a solution of trityl chloride (0.416 g, 1.49 mmol) in methylene chloride (1.5 mL) at 0-5° C., and the mixture was stirred at the same temperature for 1 hr and at 25° C. for 3.5 hr. The reaction mixture was concentrated under reduced pressure, and the concentrated residue was purified by silica gel column chromatography (17-18% ethyl acetate/hexane) to give BIT (746 mg, yield 75.4%).

¹H NMR (CDCl₃): δ=7.88 (d, J=1.6 Hz, 1H), 7.50-7.44 (m, 2H), 7.37-7.24 (m, 6H), 7.09 (d, J=8.4 Hz, 2H), 6.96-6.94 (m, 6H), 6.72 (d, J=8.4 Hz, 2H), 5.81 (s, 1H), 5.35 (s, 2H), 4.13 (q, J=7.2 Hz, 2H), 2.51 (t, J=7.6 Hz, 2H), 1.64 (s, 6H), 1.69-1.61 (m, 2H), 1.08 (t, J=7.2 Hz, 3H), 0.88 (t, J=7.2 Hz, 3H);

Mass: 717.6 [M+H]⁺.

Example 1-4

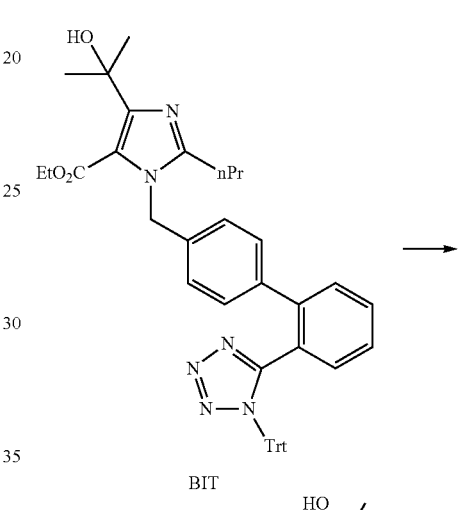

BIT

BIC

To a mixture of BIT (0.7 g, 0.98 mmol) and isopropyl alcohol (10.5 mL, 15 vol) was added a solution of potassium hydroxide in isopropyl alcohol (0.224 g in 5.0 mL), and the mixture was stirred at 40° C. for 4 hr. The reaction mixture was concentrated under reduced pressure, and to the concentrated residue were added water (5 mL), sodium chloride (0.5 g) and ethyl acetate (7 mL). The aqueous layer was extracted with ethyl acetate (3×3.5 mL, 5 vol). The organic layers were combined, washed with aqueous sodium hydrogen carbonate solution (2×3.5 mL, 5 vol), and concentrated under reduced pressure to give BIC (730 mg, quant.).

Mass: 711 [M+Na]⁺.

Example 1-5

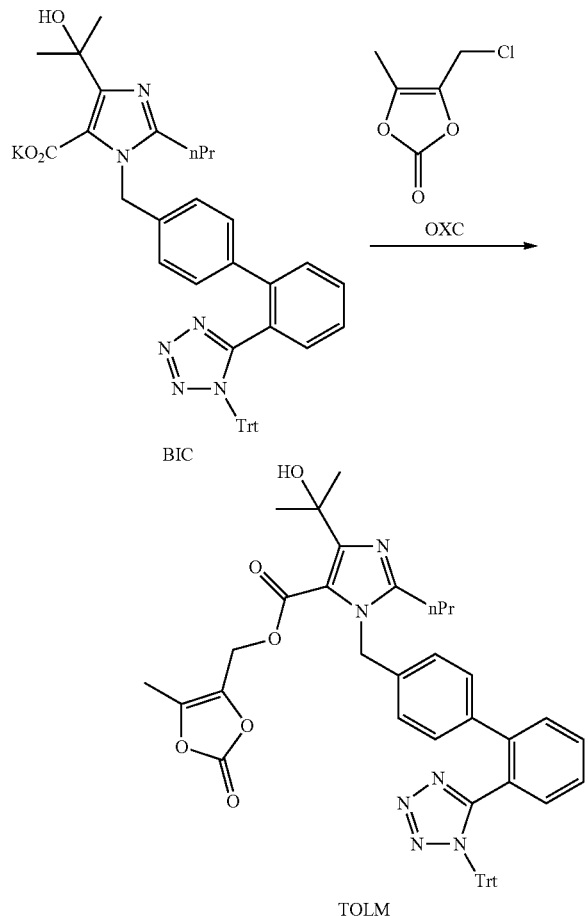

BIC

TOLM

A mixture of BIC (0.6 g, 0.83 mmol), potassium iodide (0.069 g, 0.41 mmol), OXC (0.245 g, 1.65 mmol) and methyl ethyl ketone (9.0 mL, 15 vol) was stirred at 50° C. for 20 hr. The reaction mixture was filtered, the filtrate was concentrated under reduced pressure, and the obtained concentrated residue was purified by silica gel column chromatography (20-22% ethyl acetate/hexane) to give TOLM (650 mg, yield 84.4%).

Mass: 801 [M+H]$^+$, 824 [M+Na]$^+$.

Example 1-6

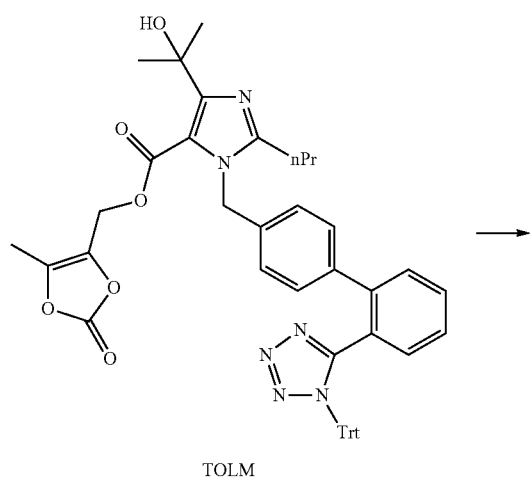

TOLM

-continued

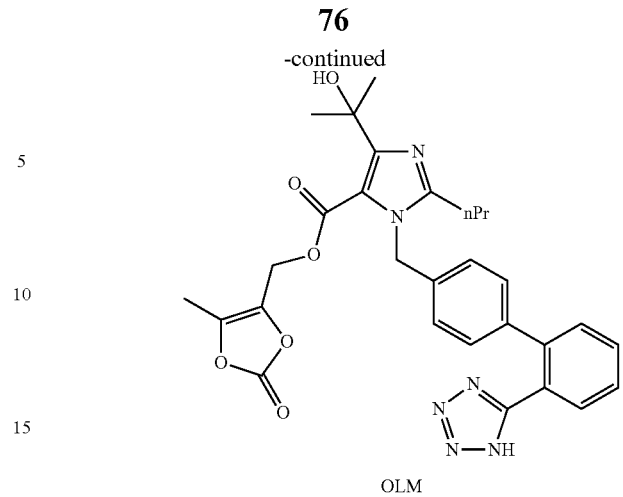

OLM

A mixture of TOLM (0.6 g, 0.75 mmol), sulfuric acid (0.08 g, 0.82 mmol) and 1:1 water-containing acetic acid (2.6 mL, 4.3 vol) was stirred at 25° C. for 1 hr. The reaction mixture was filtered, and the obtained solid was washed with 1:1 water-containing acetic acid (6.0 mL, 10 vol). The filtrates were combined and adjusted to pH 4-5 by adding 25% aqueous sodium carbonate solution. The mixture was partitioned by adding methylene chloride (6.0 mL, 10 vol). The aqueous layer was extracted with methylene chloride (3×5 mL). The organic layer was washed with water (2×5 mL) and saturated brine (5 mL), and concentrated under reduced pressure. The concentrated residue was purified by silica gel column chromatography (5-6% methanol/methylene chloride) and recrystallized from acetonitrile to give OLM (0.45 g, yield 100%).

melting point: 174.5° C.-175.2° C.;

IR (KBr): $\nu_{max}$=2969, 1831, 1706, 1475, 1226, 1134, 760 cm$^{-1}$;

$^1$H NMR (DMSO-d$_6$): δ=7.70-7.63 (m, 2H), 7.59-7.52 (m, 2H). 7.04 (d, J=8 Hz, 2H), 6.85 (d, J=8.4 Hz, 2H), 5.42 (s, 2H), 5.21 (s, 1H), 5.05 (s, 2H), 2.60 (t, J=7.6 Hz, 2H), 2.07 (s, 3H), 1.60-1.55 (m, 2H), 1.47 (s, 6H), 0.87 (t, J=7.2 Hz, 3H);

Mass: 559 [M+H]$^+$.

Example 2-1

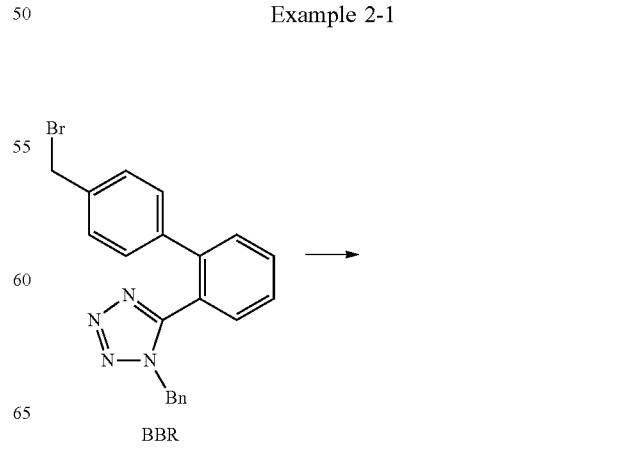

BBR

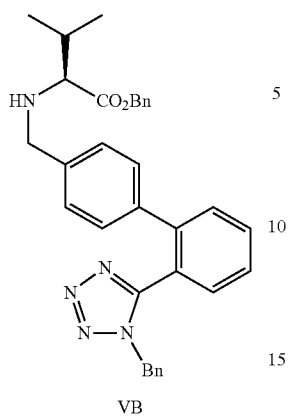

VB

A mixture of L-valine benzyl ester p-toluenesulfonate (2 g, 5.27 mmol), BBR (2.35 g, 5.8 mmol), diisopropylethylamine (2.18 mL, 13.8 mmol) and acetonitrile (20 mL, 10 vol) was stirred at 78° C. for 8 hr. The reaction mixture was concentrated under reduced pressure, and ethyl acetate was added to the concentrated residue. The mixture was washed with water and saturated brine, and concentrated under reduced pressure. The concentrated residue was purified by neutral alumina column chromatography (25-30% ethyl acetate/hexane) to give VB (2.4 g, yield 85.7%).

$^1$H NMR (CDCl$_3$): δ=7.64-7.62 (m, 1H), 7.61 (dd, J=14.0, 1.6 Hz, 1H), 7.57-7.06 (m, 14H), 6.75 (d, J=1.6 Hz, 1H), 5.19 (d, J=1.2 Hz, 2H), 4.76 (s, 2H), 3.81 (d, J=13.6 Hz, 1H), 3.55 (d, J=13.6 Hz, 1H), 3.01 (d, J=6.0 Hz, 1H), 1.98-1.93 (m, 1H), 0.95-0.92 (m, 6H);

$^{13}$C NMR (CDCl$_3$): δ=174.8, 154.5, 141.3, 140.0, 137.3, 135.6, 132.9, 131.4, 131.1, 130.1, 128.5, 128.4, 128.4, 128.3, 127.7, 127.5, 122.5, 66.5, 66.2, 51.7, 50.6, 31.5, 19.2, 18.4;

Mass: 532 [M+H]$^+$.

Example 2-2

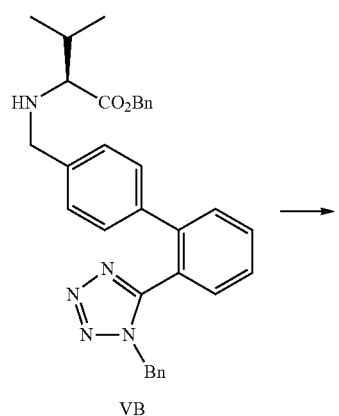

VB

To a mixture of VB (0.4 g, 0.75 mmol), diisopropylethylamine (0.44 mL, 2.65 mmol) and toluene (4 mL, 10 vol) was added dropwise valeryl chloride (0.18 g, 1.5 mmol) at 0-5° C. The reaction mixture was stirred at room temperature for 2 hr, and water (2 mL, 5 vol) was added. The organic layer was washed successively with water (2×10 mL), 0.2N aqueous sodium hydroxide solution (2×10 mL), water (2×10 mL) and saturated brine (10 mL), and concentrated under reduced pressure. The concentrated residue was purified by silica gel column chromatography (20-22% ethyl acetate/hexane) to give BVAL (0.38 g, yield 82.6%).

IR(KBr) $v_{max}$=2961, 1739, 1652, 1467, 1407, 1262, 1188, 1003, 759, 665 cm$^{-1}$;

$^1$H NMR (DMSO-d$_6$): δ=8.318 (s, 0.4H), 7.73 (dt, J=1.5, 8.0, 15.0 Hz, 0.8H), 7.56-7.51 (m, 2H), 7.37-7.33 (m, 2H), 7.27-7.21 (m, 2H), 7.09 (d, J=8.3 Hz, 1H), 7.00 (d, J=8 Hz, 0.5H), 6.86 (d, J=8.0 HZ, 1H), 6.81 (dd, J=2.0, 7.6 Hz, 1H), 5.11 (d, J=7.6 Hz, 0.4H), 5.03 (s, 1H), 4.84 (q, J=13.2 Hz, 1.6H), 4.64 (d, J=7.0 Hz, 0.8H), 4.45 (d, J=9.8 Hz, 0.7H), 4.27 (d, J=10.5 Hz, 0.7H), 2.60-2.55 (m, 1H), 2.30-2.08 (m, 2H), 1.54-1.39 (m, 2H), 1.28-1.11 (m, 3H), 0.92 (d, J=6.5 Hz, 2H), 0.87-0.83 (m, 5H);

Mass: 638 [M+H]$^+$.

Example 2-3

Deprotection

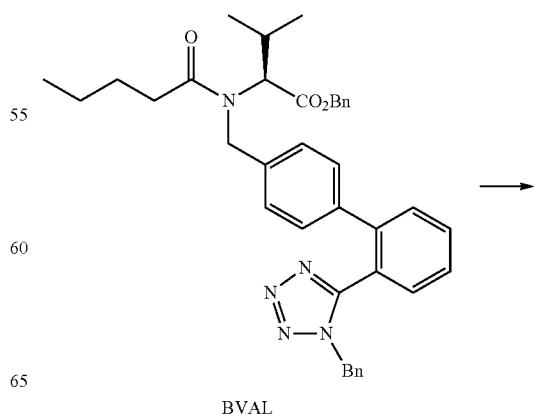

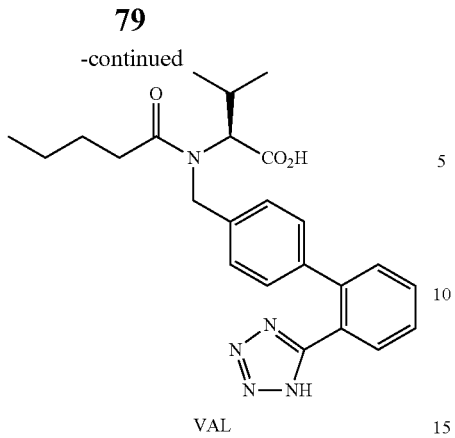

VAL

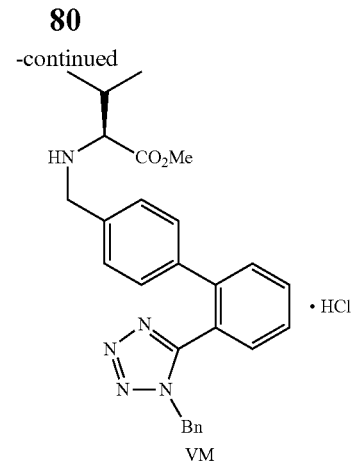

VM

A mixture of BVAL (0.1 g, 0.16 mmol), ammonium formate (0.1 g, 1.58 mmol), 5% Pd—BaSO$_4$ (0.035 g, 10 mol %), isopropyl alcohol (1 mL, 10 vol) and water (0.6 mL, 6 vol) was stirred at 65° C. for 8 hr, the reaction mixture was cooled to 25° C., and 5% Pd—BaSO$_4$ (7.0 mg, 2.0 mol %) was further added. The reaction mixture was stirred at 65° C. for 3 hr. The conversion yield of this reaction was 98.9%. The reaction mixture was filtered through celite, the filtrate was concentrated under reduced pressure, and the obtained concentrated residue was purified by silica gel column chromatography (5% methanol/methylene chloride) to give valsartan (VAL) (0.1 g, yield 70.7%).

melting point: 70° C.-95° C.;

IR (KBr): $\nu_{max}$=1730, 1619 cm$^{-1}$;

$^1$H NMR (DMSO-d$_6$): (C$_M$: major rotamer; C$_m$: minor rotamer): δ=16.3 (brs, 1H), 12.6 (brs, 1H), 7.70-7.63 (m, 2H, C$_M$, C$_m$), 7.58-7.53 (m, 2H, C$_M$, C$_m$), 7.20 (d, J=8.2 Hz, 1H, C$_M$), 7.08 (d, J=8.2 Hz, 1H, C$_m$), 7.07 (d, J=8.2 Hz, 1H, C$_M$), 6.97 (d, J=8.2 Hz, 1H, C$_m$), 4.62 (s, 2H, C$_M$), 4.48 (d, J=15.2 Hz, 1H, C$_m$), 4.46 (d, J=10.3 Hz, 1H, C$_M$), 4.43 (d, J=15.2 Hz, 1H, C$_m$), 4.08 (d, J=10.5 Hz, 1H, C$_m$), 2.53-2.45 (m, 2H, C$_m$), 2.22-2.12 (m, 1H, C$_M$, C$_m$), 2.21 (dt, J=15.8, 7.9 Hz, 1H, C$_M$), 2.03 (dt, J=15.8, 7.9 Hz, 1H, C$_M$), 1.54 (quint, J=6.9 Hz, 2H, C$_m$), 1.41 (dquint, J=14.1, 7.9 Hz, 1H, C$_M$), 1.37 (dquint, J=14.1, 7.9 Hz, 1H, C$_M$), 1.31 (sext, J=6.9 Hz, 2H, C$_m$), 1.15 (sext, J=7.9 Hz, 2H, C$_M$), 0.93 (d, J=6.9 Hz, 3H, C$_m$), 0.93 (d, J=7.9 Hz, 3H, C$_M$), 0.88 (t, J=6.9 Hz, 3H, C$_m$), 0.76 (t, J=7.9 Hz, 3H, C$_M$), 0.75 (d, J=7.9 Hz, 3H, C$_M$), 0.70 (d, J=6.9 Hz, 3H, C$_m$);

HRMS: Calcd for C$_{24}$H$_{29}$N$_5$O$_3$, 435.2270 [M]$^+$. Found 435.2267 [M]$^+$.

Example 3-1

L-valine methyl ester hydrochloride (5 g, 1 equivalent) and acetonitrile (100 mL, 20 vol) were charged in a flask, and potassium carbonate (20.6 g, 5 equivalents) was added. The reaction mixture was stirred for 5 min, and BBR (12 g, 1 equivalent) was added. The mixture was stirred at 40° C.-45° C. for 12 hr. The degree of progression of the reaction was checked by TLC: thin layer chromatography (TLC eluent: 30% ethanol/hexane, detection method: UV), and complete consumption of BBR was confirmed. The reaction mixture was filtered, and the obtained solid was washed with acetonitrile (10 mL, 2 vol). The filtrate and washing were combined, and concentrated under reduced pressure at 40° C.-45° C. to give a crude product. To this crude product was added toluene (12.5 mL, 10 vol). The mixture was adjusted to pH 1-2 with concentrated hydrochloric acid, and stirred at 25° C.-30° C. for 2 hr. The precipitated solid was collected by filtration, and dried with suction for min to give hydrochloride of VM as a crude product. The solid was suspended in 10% ethyl acetate/hexane (25 mL, 5 vol), and the suspension was stirred for 30 min. This suspension was filtered, and washed with hexane (25 mL, 5 vol). The obtained solid was dried with suction for 30 min to give hydrochloride of VM (10.4 g, yield 71%).

Example 3-2

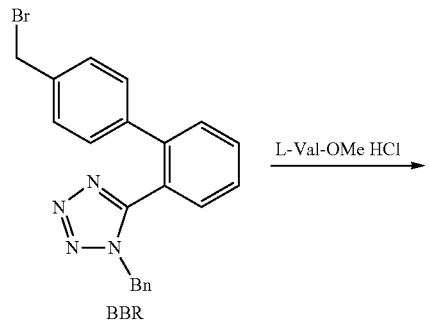

BBR

L-Val-OMe HCl →

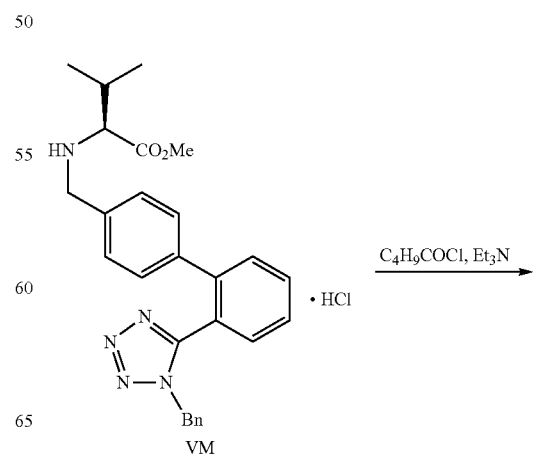

VM

C$_4$H$_9$COCl, Et$_3$N →

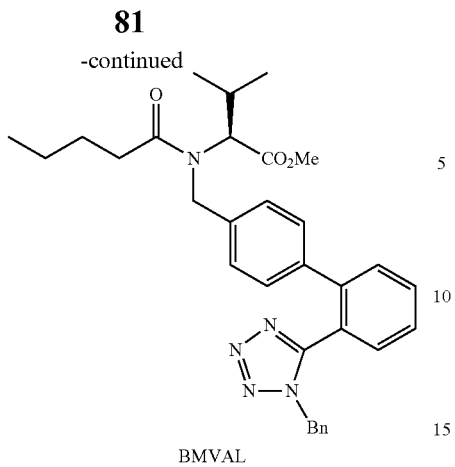

BMVAL

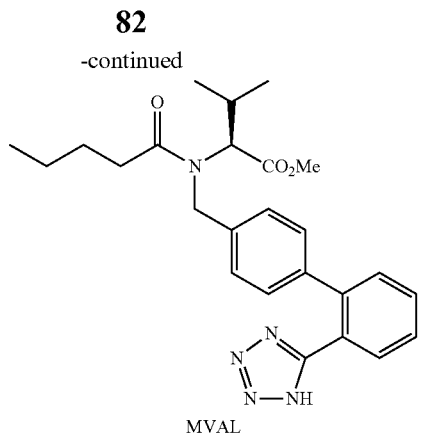

MVAL

Hydrochloride of VM (4.5 g, 1 equivalent) and toluene (45 mL, 10 vol), and diisopropylethylamine (5.7 mL, 3.5 equivalents) were charged in a flask. The mixture was stirred for 5 min, and cooled to 0° C.-5° C. To this mixture was added dropwise valeryl chloride (2.35 mL, 2 equivalents) over 10 min. After completion of the dropwise addition, the mixture was stirred at 25° C.-30° C. for 2 hr. The degree of progression of the reaction was checked by TLC (TLC eluent: 30% ethyl acetate/hexane, detection method: UV), and complete consumption of VM was confirmed. The reaction mixture was cooled to 0° C.-5° C., and water (22.5 mL, 5 vol) was added. A mixture of these two layers was stirred at 25° C.-30° C. for 1 hr, left standing, and partitioned. The organic layer was washed with deionized water (2×10 mL, 2×2.2 vol) and further washed successively with 0.2N aqueous sodium hydroxide solution (2×10 mL, 2×2.2 vol) and saturated brine (2×10 mL), and dried over sodium sulfate. The mixture was filtered, and the filtrate was concentrated under reduced pressure at 40° C.-45° C. to give BMVAL (5.44 g, yield 91%).

Example 3-3

Deprotection

BMVAL (5 g, 1 equivalent), isopropanol (50 mL, 10 vol) and water (30 mL, 6 vol) were charged in a flask. To this mixture were added ammonium formate (5.72 g, 9.8 equivalents) and 5% Pd/BaSO$_4$-Type29a (0.098 g, 10 mol %), and the mixture was stirred at 60° C.-65° C. for 4 hr. The degree of progression of the reaction was checked by TLC (TLC eluent: 30% ethyl acetate/hexane, detection method: UV), and complete consumption of BMVAL was confirmed. The reaction mixture was cooled to 25° C.-30° C., and filtered with a filter lined with celite. The celite was washed with isopropanol (25 mL, 5 vol). The filtrate and washing were combined, and the mixture was concentrated under reduced pressure at 40° C.-45° C. to give a syrup. To this syrup were added t-butyl methyl ether (25 mL, 5 vol) and deionized water (10 mL, 2 vol), and the mixture was stirred for 5 min, left standing for 5 min, and partitioned. The aqueous layer was extracted with t-butyl methyl ether (10 mL, 2 vol). The organic layers were combined, washed with deionized water (15 mL, 3 vol), and dried over sodium sulfate. The mixture was dried under reduced pressure at 40° C.-45° C. to give crude MVAL (2.0 g, yield 48%). The crude product was used without purification for the next step.

Example 3-4

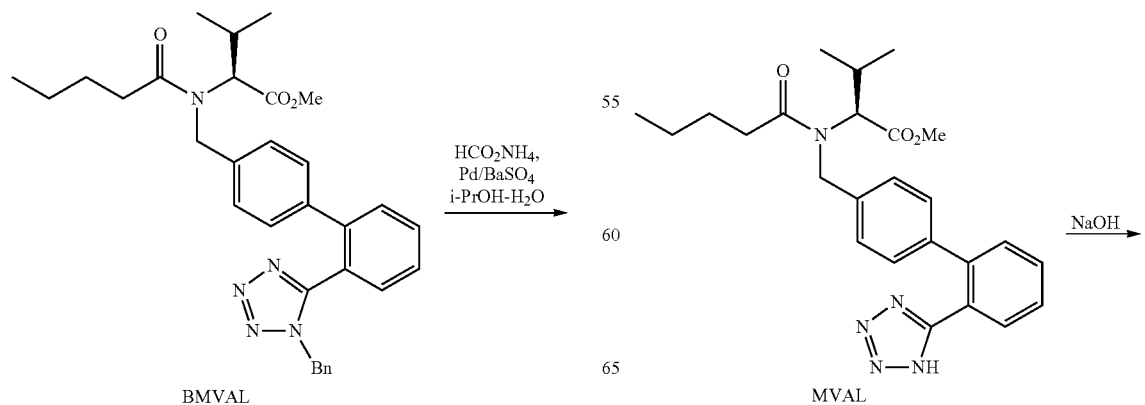

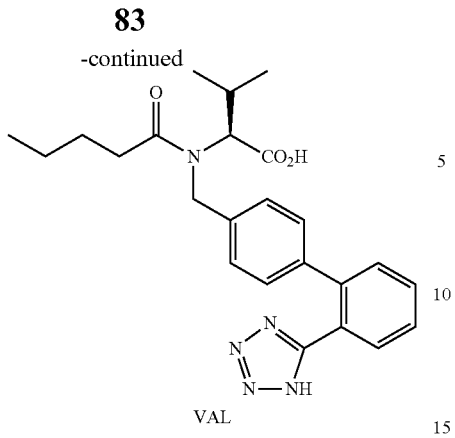

VAL

MVAL (2 g, 1 equivalent) was dissolved in methanol (5 mL, 2.5 vol). The solution was cooled to 0° C.-5° C., aqueous sodium hydroxide solution (0.53 g sodium hydroxide/2.5 mL deionized water) was added, and the mixture was stirred at 0° C.-5° C. for 5 min. The mixture was stirred at 60° C.-65° C. for 4 hr. The degree of progression of the reaction was checked by TLC (TLC eluent: 5% methanol/methylene chloride, detection method: UV), and complete consumption of MVAL was confirmed. The reaction mixture was concentrated under reduced pressure at 40° C.-45° C. To the concentrated residue were added deionized water (10 mL, 5 vol) and methylene chloride (10 mL, 5 vol), and the mixture was stirred for 5 min and partitioned. Concentrated hydrochloric acid was added at 0-5° C., and the aqueous layer was adjusted from pH 10-12 to 1-2. The obtained mixture was extracted with methylene chloride (2×10 mL, 2×5 vol). To the organic layer was added sodium sulfate, and the mixture was dried. The mixture was filtered, and the filtrate was concentrated under reduced pressure to give crude VAL (2.1 g, yield 108%). The crude product was recrystallized from ethyl acetate to give the object compound (HPLC purity: 99.72 area %).

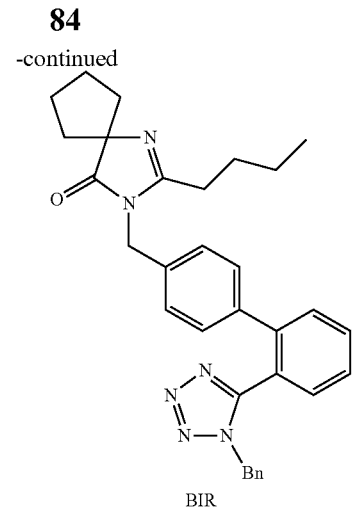

BIR

A mixture of CPI (0.2 g, 0.87 mmol), BBR (0.39 g, 0.95 mmol), potassium carbonate (0.2 g, 1.47 mmol) and acetonitrile (5.0 mL, 25.0 vol) was stirred at 80-85° C. for 20 hr. The reaction mixture was filtered, the filtrate was concentrated under reduced pressure, and the concentrated residue was purified by silica gel column chromatography (1% methanol/methylene chloride) to give BIR (0.43 g, yield 47.7%).

IR(KBr): $\nu_{max}$=1723 (COO), 1632 (CON), 1604 cm$^{-1}$;

$^1$H NMR (CDCl$_3$): δ=7.64 (td, J=7.7, 1.5 Hz, 1H), 7.54 (dd, J=7.7, 1.5 Hz, 1H), 7.44 (td, J=7.7, 1.5 Hz, 1H), 7.38 (dd, J=7.7, 1.5 Hz, 1H), 7.22 (t, J=7.7 Hz, 1H), 7.16 (t, J=7.7 Hz, 1H), 7.10 (d, J=7.7 Hz, 1H), 7.08 (d, J=7.7 Hz, 2H), 7.07 (d, J=7.7 Hz, 1H), 6.77 (d, J=7.7 Hz, 2H), 4.81 (s, 2H), 4.65 (s, 2H, CH$_2$N), 2.28 (t, J=7.7 Hz, 2H), 2.03-1.94 (m, 6H), 1.83-1.81 (m, 2H), 1.58 (quint, J=7.7 Hz, 2H), 1.33 (sext, J=7.7 Hz, 2H), 1.87 (t, J=7.7 Hz, 2H);

$^{13}$C NMR (CDCl$_3$): δ=187, 161, 154, 141, 141, 138, 137, 133, 132, 131, 131, 130, 129, 129, 129, 129, 128, 128, 128, 127, 127, 123, 51, 43, 37, 29, 28, 26, 22, 14; Mass: 519 [M+H]$^+$.

Example 4-2(a)

Deprotection

Example 4-1

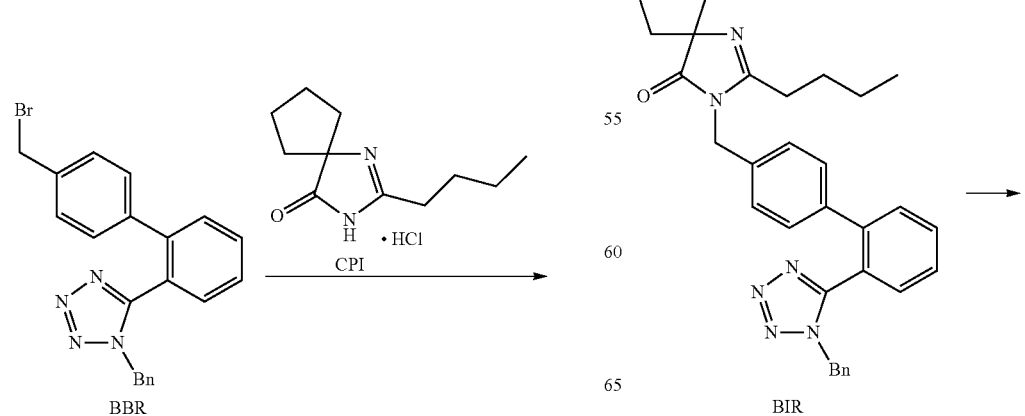

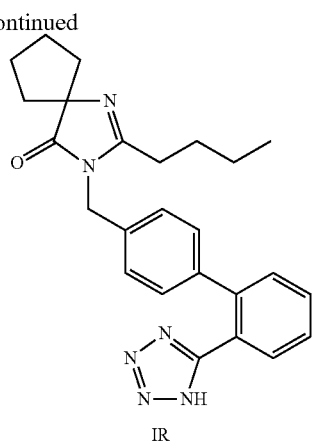

IR

A mixture of BIR (0.1 g, 0.19 mmol), ammonium formate (0.059 g, 0.94 mmol), 5% Pd—BaSO$_4$ (0.021 g, 5.0 mol %), isopropyl alcohol (1.0 mL, 10 vol) and water (0.6 mL, 6 vol) was stirred at 55° C. for 3.5 hr. The conversion yield of this reaction was 87.42%. The reaction mixture was filtered through celite, the filtrate was concentrated under reduced pressure, and the concentrated residue was purified by silica gel column chromatography to give irbesartan (IR) (0.091 g).

IR (KBr): ν$_{max}$=1725, 1630 cm$^{-1}$;

$^1$H NMR (DMSO-d$_6$): δ=7.68 (t, J=7.8 Hz, 1H), 7.64 (d, J=7.8 Hz, 1H), 7.57 (t, J=7.8 Hz, 1H), 7.04 (d, J=7.8 Hz, 1H), 7.08 (s, 4H), 4.68 (s, 2H), 2.29 (t, J=7.5 Hz, 2H), 1.86-1.60 (m, 8H), 1.47 (quint, J=7.5 Hz, 2H), 1.26 (sext, J=7.5 Hz, 2H), 0.80 (t, J=7.5 Hz, 2H);

Mass: 429 [M+H]$^+$.

Example 4-2(b)

Deprotection

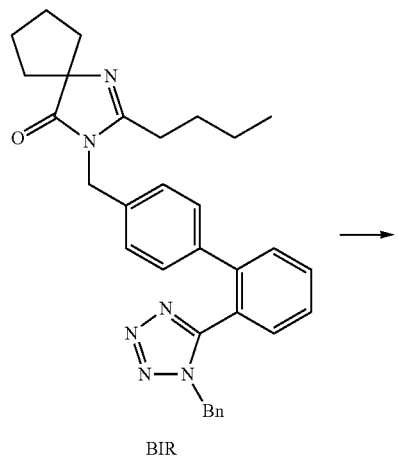

BIR

→

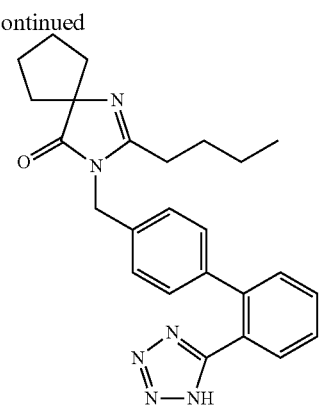

IR

A mixture of BIR (0.1 g, 0.19 mmol), ammonium formate (0.059 g, 0.94 mmol), 5% Pd—BaSO$_4$ (0.021 g, 5.0 mol %), isopropyl alcohol (1.0 mL, 10 vol) and water (0.6 mL, 6 vol) was stirred at 55° C. for 4 hr. The conversion yield of this reaction was 87.42%. The reaction mixture was filtered through celite, and the filtrate was concentrated under reduced pressure. To the concentrated residue were added ethyl acetate and water, and the mixture was partitioned. The aqueous layer was extracted with chloroform, and the organic layers were combined and concentrated under reduced pressure. To the concentrated residue was added 95% ethanol, and the mixture was dissolved by heating, and cooled to 10° C. to allow for crystallization. The precipitated crystals were filtered, washed with cold ethanol, and dried under reduced pressure to give irbesartan (IR) (0.056 g, yield 68.3%).

Example 5-(1)(a)

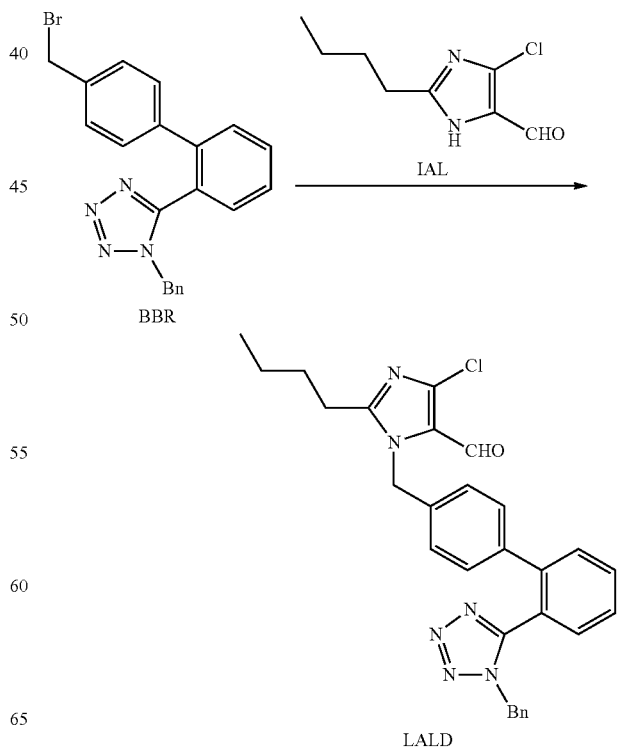

BBR

IAL

→

LALD

A mixture of IAL (0.2 g, 0.11 mmol), BBR (0.48 g, 1.18 mmol), potassium carbonate (0.25 g, 1.82 mmol) and acetonitrile (5 mL, 25 vol) was stirred at 80-85° C. for 20 hr. The reaction mixture was filtered, the filtrate was concentrated under reduced pressure, and the concentrated residue was purified by silica gel column chromatography (18-20% ethyl acetate/hexane) to give LALD (0.4 g, yield 76.9%).

IR (KBr): $\nu_{max}$=1665, 1517, 1459, 1275 cm$^{-1}$;

$^1$H NMR (CDCl$_3$): δ=9.76 (s, 1H), 7.65-7.61 (m, 1H), 7.53 (dd, J=8.0, 1.2 Hz, 1H), 7.44 (dt, J=7.6, 1.2 Hz, 1H), 7.33 (dd, J=7.6, 1.2 Hz, 1H), 7.24-7.14 (m, 3H) 7.08 (d, J=8.0 Hz, 2H), 6.99 (d, J=8 Hz, 2H), 6.78 (d, J=7.6 Hz, 2H), 5.52 (s, 2H), 4.80 (s, 2H), 2.61 (t, J=7.6 Hz, 2H), 1.72-1.64 (m, 2H), 1.40-1.31 (m, 2H), 0.90 (t, J=7.2 Hz, 3H);

Mass: 511 [M]$^+$.

Example 5-(1)(b)

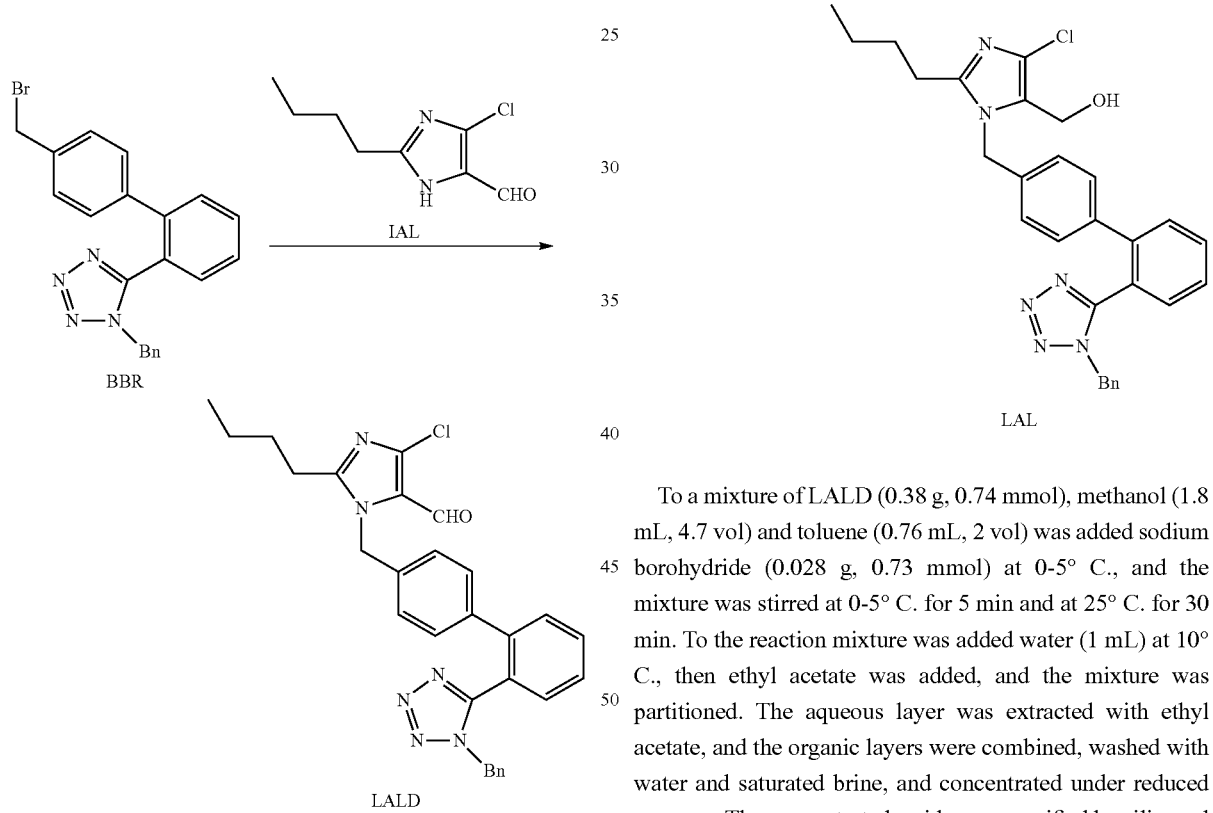

A mixture of IAL (2 g, 10.7 mmol), BBR (4.8 g, 11.8 mmol), potassium carbonate (2.5 g, 18.2 mmol) and acetonitrile (20 mL, 10 vol) was stirred at 25° C. for 20 hr. Furthermore, BBR (0.22 g) was added at 25° C., and the mixture was stirred at the same temperature for 5 hr. The reaction mixture was filtered, the filtrate was concentrated under reduced pressure, and the concentrated residue was purified by silica gel column chromatography (17-18% ethyl acetate/hexane) to give LALD (3.5 g, yield 64.3%).

Example 5-(2)(a)

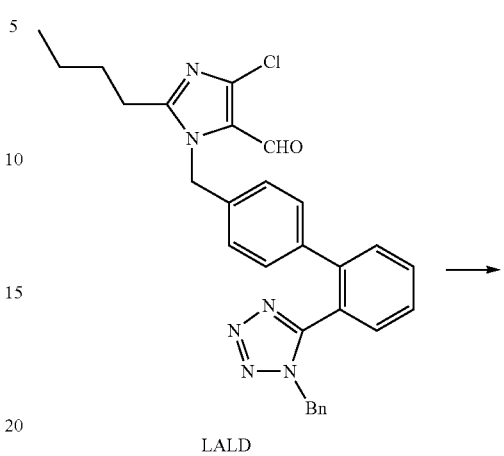

To a mixture of LALD (0.38 g, 0.74 mmol), methanol (1.8 mL, 4.7 vol) and toluene (0.76 mL, 2 vol) was added sodium borohydride (0.028 g, 0.73 mmol) at 0-5° C., and the mixture was stirred at 0-5° C. for 5 min and at 25° C. for 30 min. To the reaction mixture was added water (1 mL) at 10° C., then ethyl acetate was added, and the mixture was partitioned. The aqueous layer was extracted with ethyl acetate, and the organic layers were combined, washed with water and saturated brine, and concentrated under reduced pressure. The concentrated residue was purified by silica gel column chromatography (30% ethyl acetate/hexane) to give LAL (0.3 g, yield 78.7%).

IR (KBr): $\nu_{max}$=2935, 1725, 1577, 1256 cm$^{-1}$;

$^1$H NMR (CDCl$_3$): δ=7.51 (t, J=7.6 Hz, 1H), 7.40 (d, J=6.8 Hz, 1H), 7.32 (t, J=7.6 Hz, 1H), 7.19 (d, J=7.6 Hz, 1H), 7.10-7.00 (m, 3H), 6.95 (d, J=8 Hz, 2H), 6.79 (d, J=8.0 Hz, 2H), 6.66 (d, J=8.0 Hz, 2H), 5.05 (s, 2H), 4.71 (s, 2H), 4.36 (s, 2H), 2.42 (t, J=8.0 Hz, 2H), 1.57-1.50 (m, 2H), 1.25-1.15 (m, 2H), 0.92-0.83 (m, 3H);

$^{13}$C NMR (CDCl$_3$): δ=154.3, 148.4, 141.0, 138.4, 136.1, 132.9, 131.6, 131.1, 130.2, 129.2, 128.7, 128.7, 128.0, 127.8, 127.2, 126.5, 124.9, 122.5, 52.9, 50.9, 47.1, 29.6, 26.7, 22.3, 13.7.

Example 5-(2)(b)

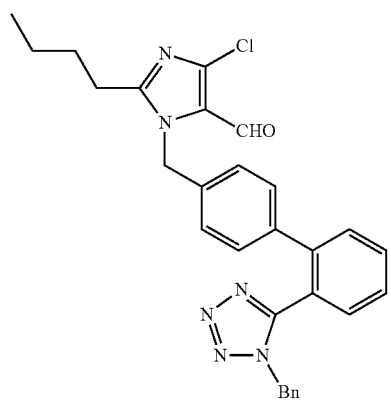

LALD

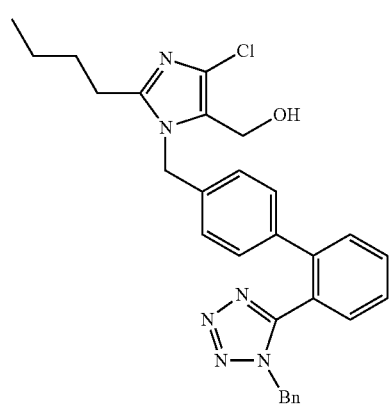

LAL

To a mixture of LALD (2 g, 3.9 mmol), methanol (9.5 mL, 4.75 vol) and toluene (4 mL, 2 vol) was added sodium borohydride (0.145 g, 3.8 mmol) at 0-5° C., and the mixture was stirred at 0-5° C. for 5 min and at 25° C. for 30 min. To the reaction mixture was added water (4 mL) at 10° C., then ethyl acetate was added, and the mixture was partitioned. The aqueous layer was extracted with ethyl acetate, and the organic layers were combined, washed with water and saturated brine, and concentrated under reduced pressure. To the concentrated residue was added a mixture of ethyl acetate/hexane=3/97 to allow for crystallization, and the obtained crystals were washed with hexane and dried under reduced pressure to give LAL (1.9 g, yield 94.6%).

Example 5-3(a)

Deprotection

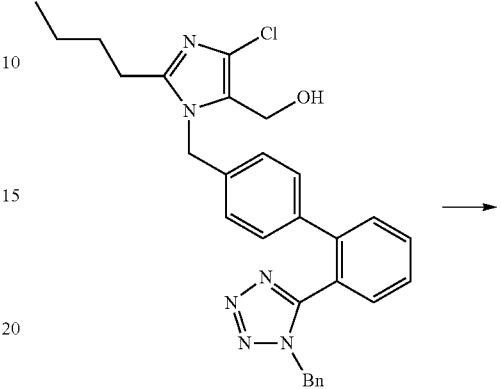

A mixture of LAL (0.1 g, 0.195 mmol), ammonium formate (0.06 g, 0.95 mmol), 5% Pd—BaSO$_4$ (0.033 g, 8.0 mol %), isopropyl alcohol (1.0 mL, 10 vol) and water (0.6 mL, 6 vol) was stirred at 60° C. for 8 hr. The conversion yield of this reaction was 96.98%. The reaction mixture was filtered through celite, and the filtrate was concentrated under reduced pressure. To the concentrated residue was added ethyl acetate, and the mixture was extracted. The aqueous layer was extracted with ethyl acetate, and the organic layers were combined and concentrated under reduced pressure. The concentrated residue was purified by silica gel column chromatography (6% methanol/methylene chloride) to give losartan (LOS) (0.57 g, yield 70.7%).

melting point: 161° C.-164° C.;

IR (KBr): ν$_{max}$=1469, 1256, 1021, 756 cm$^{-1}$;

$^1$H NMR (DMSO-d$_6$): δ=7.70-7.50 (m, 4H), 7.12-7.00 (m, 4H), 5.23 (s, 2H), 4.32 (s, 2H), 2.45 (t, J=7.6 Hz, 2H), 1.46-1.42 (m, 2H), 1.25-1.20 (m, 2H), 0.79 (t, J=8 Hz, 3H);

$^{13}$C NMR (DMSO-d$_6$): δ=147.0, 140.5, 138.0 136.2, 135.4, 130.6, 130.1, 128.6, 127.3, 125.8, 125.5, 50.8, 46.1, 28.4, 25.1, 21.1, 13.1;

MS: 423 [M+H]$^+$.

Example 5-3(b)

Deprotection

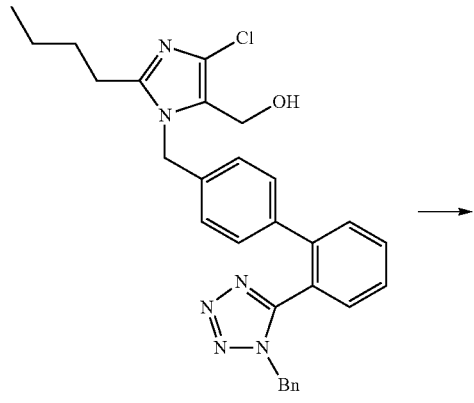

LAL

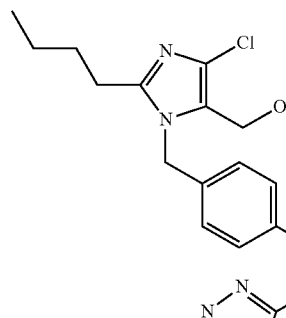

LOS

A mixture of LAL (0.1 g, 0.195 mmol), ammonium formate (0.06 g, 0.95 mmol), 5% Pd—BaSO₄ (0.021 g, 5.0 mol %), isopropyl alcohol (1.0 mL, 10 vol) and water (0.6 mL, 6 vol) was stirred at 30° C. for 20 hr. The conversion yield of this reaction was 93.77%.

Example 6-1

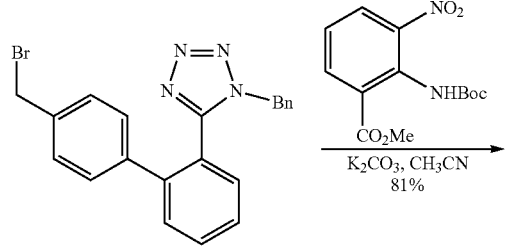

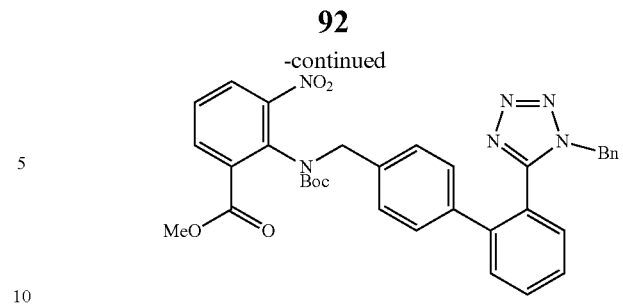

-continued

A mixture of BBR (9.82 g, 24 mmol), 2-(tert-butoxycarbonylamino)-3-nitrobenzoic acid methyl ester (7.32 g, 24.7 mmol), potassium carbonate (3.68 g, 26.7 mmol) and acetonitrile (100 mL) was heated under reflux under an argon stream for 6 hr. To the reaction mixture was added potassium carbonate (1.34 g), and the mixture was heated under reflux for 3 hr. The reaction mixture was cooled and filtered, and the insoluble material was washed with chloroform. The filtrate and washing were combined and concentrated under reduced pressure. The concentrated residue was purified by silica gel column chromatography (hexane-→hexane:ethyl acetate=5:1→4:1→3:1→2:1→3:2) to give a Boc compound of the object compound as a yellow amorphous product (12.17 g, yield 81%).

IR: 1710 cm⁻¹.

$^1$H NMR (CDCl₃): δ=8.05-8.11 and 7.88-7.90 (m, 2H), 7.60-7.61 (m, 1H), 7.50-7.52 (m, 1H), 7.05-7.26 (m, 10H), 6.78-6.80 (m, 2H), 4.85-4.94 and 4.72-4.75 (m, 4H), 3.79 (s, 3H), 1.34 (s, 9H).

MS: m/z=621 (NH⁺)

Example 6-2

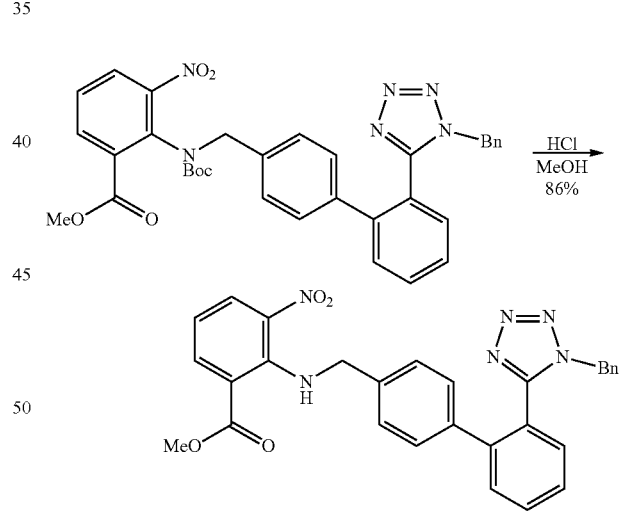

To a mixture of the Boc compound (11.93 g, 19.2 mmol) in methanol (15 mL) was added 2N hydrogen chloride/methanol solution (30 mL) under ice-cooling, and the mixture was stirred at the same temperature for 2 hr and at room temperature overnight. The reaction mixture was concentrated under reduced pressure, methanol and diisopropyl ether were added to the concentrated residue to allow for crystallization, and the crystals were collected by filtration. The obtained crystals were washed with diisopropyl ether and hexane, and dried under reduced pressure to give a nitro compound of the object compound as yellow crystals (8.64 g, yield 86%).

melting point: 115° C.-117° C.
IR: 1696, 1530, 1451, 1256 cm$^{-1}$.
$^1$H NMR (CDCl$_3$): δ=8.59-8.62 (m, 1H), 8.05-8.08 (m, 2H), 7.94-7.96 (m, 2H), 7.73-7.75 (m, 1H), 7.52-7.62 (m, 3H), 7.17-7.26 (m, 4H), 6.94-6.96 (m, 2H), 6.80-6.83 (m, 3H).
MS: m/z=521 (NH$^+$)
Anal: Calcd for C$_{29}$H$_{24}$N$_6$O$_4$: C, 6691; H, 9.65; N, 16.14%. Found: C, 66.75; H, 4.66; N, 16.19%.

Example 6-3

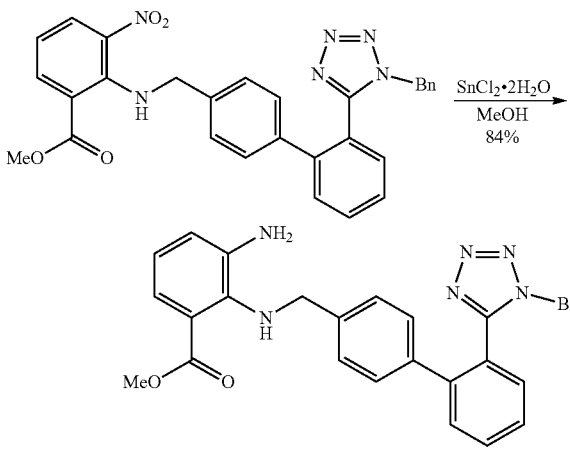

A mixture of the nitro compound (8.396 g), tin(II) chloride dihydrate (13.56 g) and methanol (155 mL) was heated under reflux for 2 hr. The reaction mixture was concentrated under reduced pressure, to the concentrated residue were added saturated aqueous sodium hydrogen carbonate solution and ethyl acetate, and the mixture was stirred for 1 hr. The mixture was filtered, and the insoluble material was washed with ethyl acetate. The filtrate and washing were combined and concentrated under reduced pressure, and the concentrated solution was extracted with ethyl acetate. A solution of the resultant product in ethyl acetate was dried over magnesium sulfate and filtered. The filtrate was concentrated under reduced pressure, and the concentrated residue was purified by silica gel column chromatography (hexane→hexane:ethyl acetate=5:1→4:1→3:1→2:1→3:2) to give a diamino compound of the object compound as a brown amorphous product (6.68 g, yield 84%).
IR: 1692, 1468 cm$^{-1}$.
$^1$H NMR (CDCl$_3$): δ=7.56-7.64 (m, 2H), 7.05-7.43 (m, 10H), 6.86-6.90 (m, 2H), 6.74-6.76 (m, 2H), 4.68 (s, 2H), 4.16 (s, 2H), 3.80 (s, 3H).
MS: m/z=491 (NH$^+$)

Example 6-4

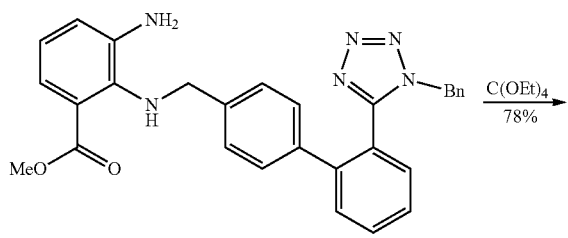

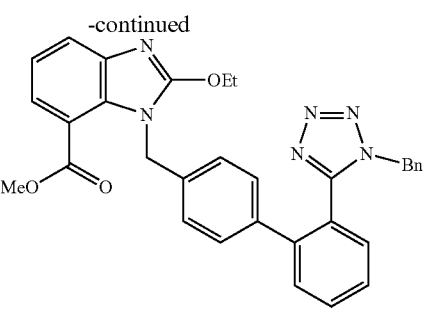

A mixture of the diamino compound (6.46 g, 13 mmol), tetraethoxymethane (3.6 mL, 17 mmol) and acetic acid (8 mL) was stirred at 90° C. for 1 hr. The reaction mixture was cooled, ice and saturated aqueous sodium hydrogen carbonate solution were added, and the mixture was extracted with chloroform. The extract was dried over magnesium sulfate and filtrated, and the filtrate was concentrated under reduced pressure. The concentrated residue was purified by silica gel column chromatography (hexane→hexane:ethyl acetate=5:1→4:1→3:1→2:1→1:1) to give a methyl ester compound of the object product as a brown amorphous product (5.61 g, yield 78%).
IR: 1715, 1548 cm$^{-1}$
$^1$H NMR (CDCl$_3$): δ=7.72-7.74 (m, 1H), 7.10-7.62 (m, 9H), 6.99 (d, J=8 Hz, 2H), 6.90 (d, J=8 Hz, 2H), 6.70-6.72 (m, 2H), 5.59 (s, 2H), 4.70 (q, J=4 Hz, 2H), 4.65 (s, 2H), 3.76 (s, 3H), 1.50 (t, J=4 Hz, 3H).
MS: m/z=545 (NH$^+$)

Example 6-5

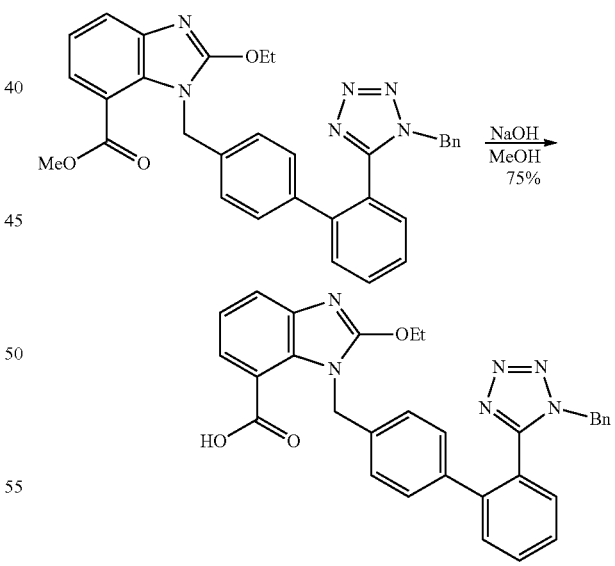

A mixture of the methyl ester compound (5.4 g, 9.9 mmol), 1N aqueous sodium hydroxide solution (30 mL) and methanol (15 mL) was stirred at 90° C. for 2 hr. Methanol was concentrated under reduced pressure, 10% hydrochloric acid was added, and the resultant product was extracted with a mixture of chloroform and THF. The extract was dried over magnesium sulfate and filtrated, and the filtrate was concentrated under reduced pressure. The concentrated residue was purified by silica gel column chromatography (2%→4% methanol/chloroform). A fraction of the object compound was collected and concentrated under reduced pressure. To the concentrated residue was added a mixture of chloroform and diisopropyl ether to allow for crystallization, and the obtained crystals were washed with diisopropyl ether and dried to give a carboxylic acid compound of the object compound as a colorless solid (3.96 g, yield 75%).

melting point: 171° C.-173° C.

IR: 1696, 1530, 1451, 1256 cm$^{-1}$ $^1$H NMR (DMSO-d$_6$): δ=7.65-7.72 (m, 2H), 7.49-7.56 (m, 4H), 7.15-7.23 (m, 4H), 6.86-6.90 (m, 4H), 6.75-6.77 (m, 2H), 5.59 (s, 2H), 4.97 (s, 2H), 4.59 (q, J=8 Hz, 2H), 1.37 (t, J=8 Hz, 3H).

MS: m/z=531 (NH$^+$)

Anal: Calcd for C$_{31}$H$_{26}$N$_6$O$_3$.0.1H$_2$O: C, 69.94; H, 4.96; N, 15.79%. Found: C, 69.83; H, 4.96; N, 15.73%.

Example 6-6

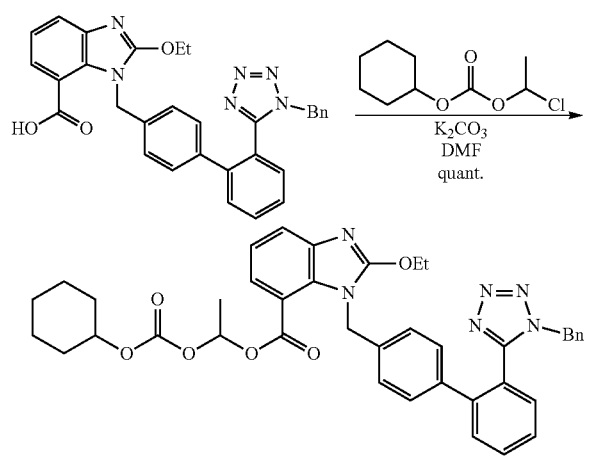

A mixture of the carboxylic acid compound (3.71 g, 6.99 mmol), 1-chloroethylcyclohexyl carbonate (1.73 g), potassium carbonate (1.54 g) and DMF (20 mL) was stirred at 65° C. for 4 hr. To the reaction mixture was added water, and the resultant product was extracted with ethyl acetate. The extract was washed with water, dried over magnesium sulfate and filtered. The filtrate was concentrated under reduced pressure, and the concentrated residue was purified by silica gel column chromatography (hexane→hexane: ethyl acetate=4:1→2:1→3:2→1:1) to give BCAN of the object compound as a yellow amorphous product (4.9 g, quant.).

IR: 1751, 1549, 1458 cm$^{-1}$ $^1$H NMR (CDCl$_3$): δ=7.74-7.76 (m, 1H), 7.57-7.61 (m, 2H), 7.48-7.50 (m, 1H), 7.30-7.40 (m, 2H), 7.13-7.18 (m, 3H), 6.87-7.02 (m, 5H), 6.70-6.72 (m, 2H), 5.56-5.67 (m, 2H), 4.61-4.71 (m, 6H), 1.85-1.93 (m, 2H), 1.65-1.80 (m, 2H), 1.20-1.62 (m, 13H).

MS: m/z=701 (NH$^+$)

Example 6-7

Deprotection

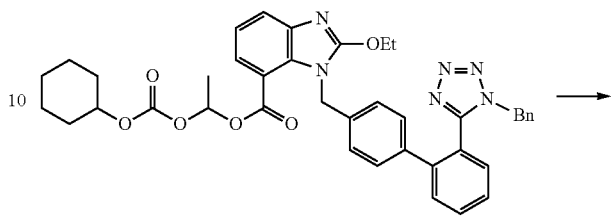

BCAN

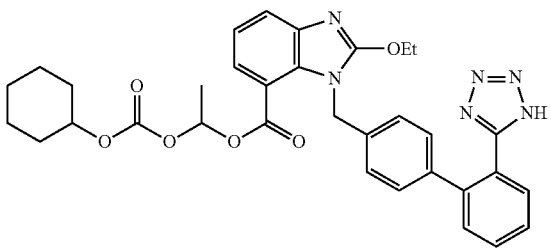

CAN

A mixture of BCAN (0.1 g, 0.14 mmol), ammonium formate (0.044 g, 0.69 mmol), 5% Pd—BaSO$_4$ (0.0152 g, 5 mol %), isopropyl alcohol (1 mL, 10 vol) and water (0.6 mL, 6 vol) was stirred at 25° C. for 14 hr. The conversion yield of this reaction was 92.10%.

Example 6-8

Deprotection

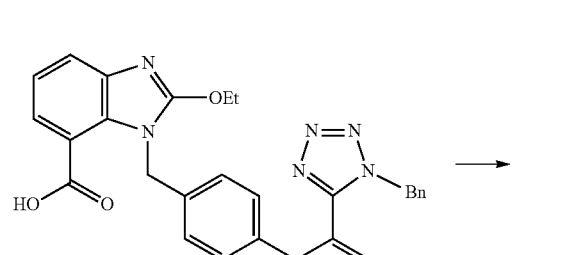

CBCA

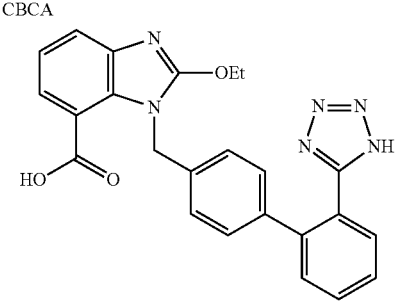

CV

A mixture of 2-ethoxy-1-[2'-[1-benzyl-1H-tetrazol-5-yl] biphenyl-4-yl]-1H-benzimidazole-7-carboxylic acid (CBCA) (0.05 g, 0.094 mmol), ammonium formate (0.029 g, 0.46 mmol), 10% Pd/BaSO$_4$-Type29a (0.005 g, 5 mol %), isopropyl alcohol (0.5 mL, 10 vol) and water (0.3 mL, 6 vol) was stirred at 45-48° C. for 7 hr. After completion of the reaction, the reaction mixture was cooled to 25° C. and filtered through celite. The filtrate was concentrated under reduced pressure, to the concentrated residue were added water (2.0 mL) and methylene chloride (5.0 mL), and the mixture was adjusted to pH 2 with 10% hydrochloric acid (0.3 mL). The precipitated solid was filtered, washed with methylene chloride (2.0 mL), and dried under reduced pressure at 45° C. to give 2-ethoxy-1-{[2'-(2H-tetrazol-5-yl)-1,1'-biphenyl]-4-yl]methyl}-1H-benzimidazole-7-carboxylic acid (CV) (0.03 g, yield 73.2%).

IR (KBr): $v_{max}$=3436, 2986, 2756, 1704, 1550, 1479, 1428, 1283, 1241, 1036, 746 cm$^{-1}$;

$^1$H NMR (DMSO-d$_6$): δ=16.29 (s, 1H), 13.19 (s, 1H), 7.67-1.63 (m, 3H), 7.57-7.48 (m, 3H), 7.19-7.16 (m, 1H), 7.01 (d, J 7.6 Hz, 2H), 6.92 (d, J=7.6 Hz, 2H), 5.62 (s, 2H), 4.57 (t, J=6.8 Hz, 2H), 1.38 (t, J=6.8 Hz, 3H)

Example 7-1

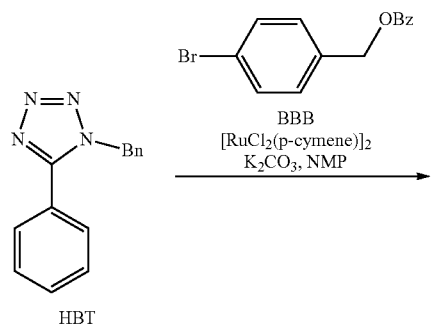

A mixture of 1-benzyl-5-phenyl-1H-tetrazole (HBT, 100 g, 1 eq), p-bromobenzyl benzoate (BBB, 135.5 g, 1.1 eq), potassium carbonate (58.5 g, 1 eq), triphenylphosphine (2.23 g, 2 eq relative to Ru) and N-methyl-2-pyrrolidone (380 mL, 3.8 vol) was stirred for 5 min. A solution (122 mL, 2 eq relative to Ru) of 2.5% potassium bis(2-ethylhexyl)phosphate in N-methyl-2-pyrrolidone was added thereto, and the mixture was stirred for min. Argon gas was blown into the mixture for 10 min to remove oxygen from the mixture. The reaction mixture was heated to 138° C.-140° C., and dichloro(p-cymene)ruthenium (II) dimer (1.3 g, 0.005 eq) was added at 138° C.-140° C. Furthermore, argon gas was blown into the mixture for 10 min to remove oxygen from the reaction mixture. Then, the reaction mixture was stirred at 138° C.-140° C. for 8 hr. The reaction was checked by TLC (TLC eluent: 30% ethyl acetate/hexane, detection method: UV) and HBT contained therein was confirmed to be in a trace amount.

The reaction mixture was cooled to 25° C.-30° C., t-butyl methyl ether (500 mL, 5 vol) was added thereto, and the mixture was stirred for 5 min and filtered through a filter lined with celite. The celite layer was washed with t-butyl methyl ether (500 mL, 5 vol). The filtrate and washing were combined, deionized water (500 mL, 5 vol) was added thereto, and the mixture was stirred for 10 min and left standing for 5 min. After partitioning, the aqueous layer was extracted with t-butyl methyl ether (2×500 mL, 2×5 vol). The extracts were combined with the organic layer, deionized water (500 mL, 5 vol) was added, and the mixture was stirred for 10 min. The mixture was left standing for 5 min and partitioned. To the t-butyl methyl ether layer was added saturated brine (500 mL, 5 vol), and the mixture was stirred for 10 min. After standing, the mixture was partitioned, and the t-butyl methyl ether layer was dried over sodium sulfate (50 g, 0.5 w/w). The residue was filtered and the filtrate was concentrated under reduced pressure at 40° C.-45° C. to give a crude product of BBZ (220 g) as a green syrup.

To the obtained crude product was added t-butyl methyl ether (400 mL, 4 vol), and the mixture was stirred at 25° C.-30° C. for 24 hr to allow for precipitation of a solid. The obtained solid was collected by filtration and dried with suction to give BBZ as a green solid (140 g, yield 68.5%).

Example 7-2

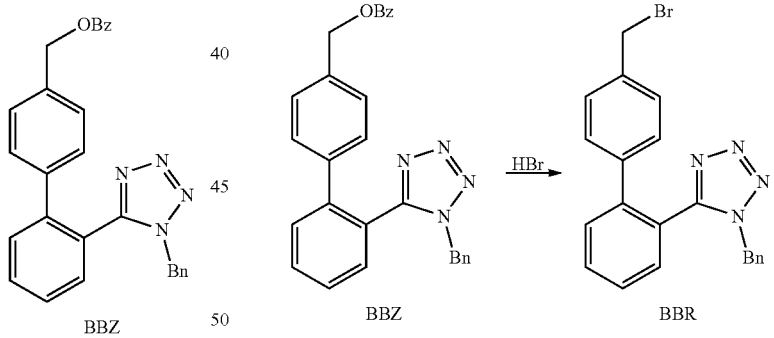

To BBZ (135 g, 1 eq) cooled to 0° C.-5° C. was added 33% hydrogen bromide/acetic acid solution (405 mL, 3 vol) at 0° C.-5° C. over 15 min. The reaction mixture was stirred at 25° C.-30° C. for 18 hr. The degree of progression of the reaction was checked by TLC (TLC eluent: 30% ethyl acetate/hexane, detection method: UV), and complete disappearance of BBZ was confirmed.

The reaction mixture was filtered, precipitated BBR was collected by filtration, and the obtained solid was dried with suction for 1 hr and further blast-dried for 8 hr. To the obtained solid was added 50% ethyl acetate/hexane (270 mL, 2 vol), and the obtained suspension was stirred at 25° C.-30° C. for 1 hr. The suspension was filtered to give BBR as a pale-yellow solid (113 g, yield 92%).

Example 7-3

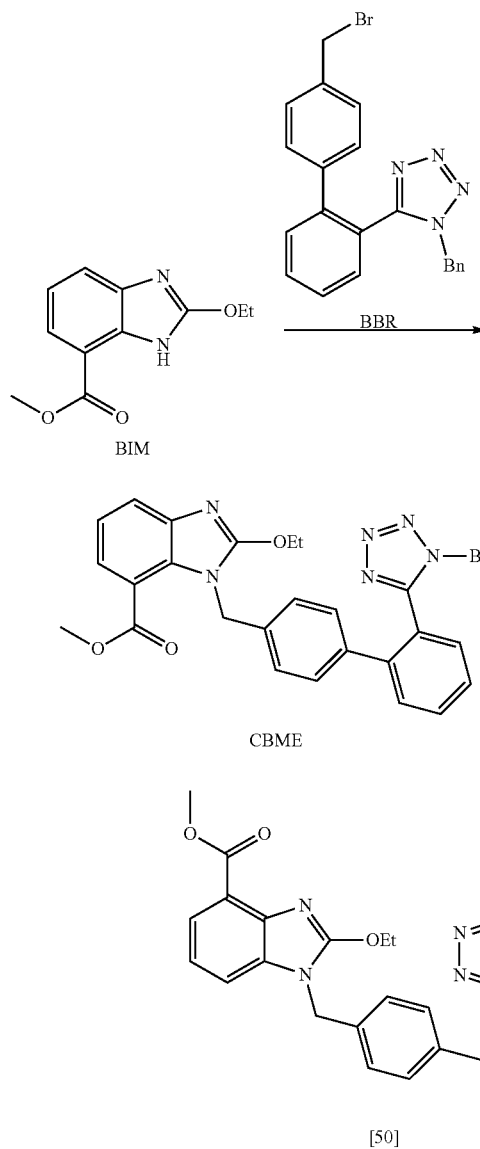

Dimethylacetamide (1 mL, 1 vol), methanol (4 mL, 4 vol), BIM (1 g, 1 equivalent) and potassium carbonate (1.56 g, 2.5 equivalents) were charged in a two-neck flask at 25° C.-30° C. The reaction mixture was stirred at 25° C.-30° C. for 15 min, and BBR (1.93 g, 1.05 equivalents) was gradually added. The reaction mixture was stirred at 25° C.-30° C. for 24 hr. The degree of progression of the reaction was checked by TLC (TLC eluent: 40% ethyl acetate/hexane, detection method: UV). After BBR was completely consumed, water (10 mL, 10 vol) was added to the reaction mixture, and the mixture was stirred for 1 hr. The precipitated solid was filtered, washed with water (3 mL, 3 vol), and dried with suction for 15 min. The obtained solid was blast-dried at 50° C.-55° C. for 4 hr to give crude CBME (2.3 g, yield 93.1%, HPLC purity: 74.80 area %) as a pink solid.

To the above-mentioned pink solid was added MTBE (8.0 mL, 8 vol), and the mixture was stirred at 25° C.-30° C. for 1 hr. The precipitated solid was filtered, washed with t-butyl methyl ether (4.0 mL, 4 vol), and dried with suction for 15 min. The obtained solid was blast-dried at 50° C.-55° C. for 4 hr to give CBME as a pink solid (1.7 g, yield 68.8%, HPLC purity: 88.47 area %).

To this pink solid was added acetone (10 mL, 10 vol), and the obtained solution was heated to 50° C.-55° C. Water (5.0 mL, 5 vol) was added, and the mixture was stirred at 50° C.-55° C. for 30 min and at 0° C.-5° C. for 45 min. The precipitated solid was collected by filtration and washed with water (2.0 mL, 2 vol). The obtained solid was dried with suction and blast-dried at 50° C.-55° C. for 4 hr to give CBME (1.5 g, yield 60.7%, HPLC purity: 95.66 area %).

The steps after acetone addition were performed once again to obtain CBME (1.1 g, yield 44.5%, HPLC purity: 97.64 area %).

Example 7-4

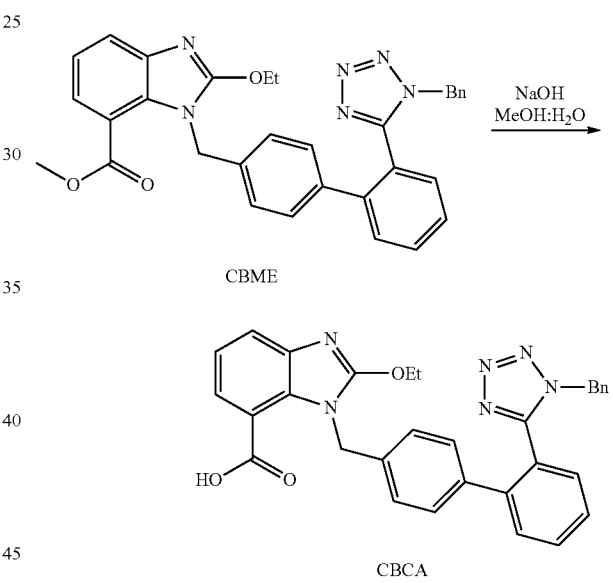

Methanol (14 mL, 4 vol), CBME (3.5 g, 1 equivalent) and aqueous sodium hydroxide solution (0.771 g as sodium hydroxide, 3 equivalents) (14 mL, 4 vol) were charged in a two-neck flask. The reaction mixture was stirred at 75° C.-80° C. for 3 hr. The degree of progression of the reaction was checked by TLC (TLC eluent: 5% methanol/methylene chloride, detection method: UV). The reaction mixture was cooled, and the solvent was evaporated under reduced pressure at 45° C.-50° C. To the concentrated residue was added water (35 mL, 10 vol), and the mixture was cooled to 10° C.-15° C. The mixture was adjusted from pH 10-11 to pH 5-6 with acetic acid (1.0 mL, 0.3 vol), and stirred at 25° C.-30° C. for 1 hr. The precipitated solid was collected by filtration and washed with deionized water (3.5 mL, 1 vol). The obtained solid was dried with suction for 15 min, and blast-dried at 50° C.-55° C. for 4 hr to give CBCA (3.2 g, yield 93.8%, HPLC purity: 98.34 area %).

Example 7-5

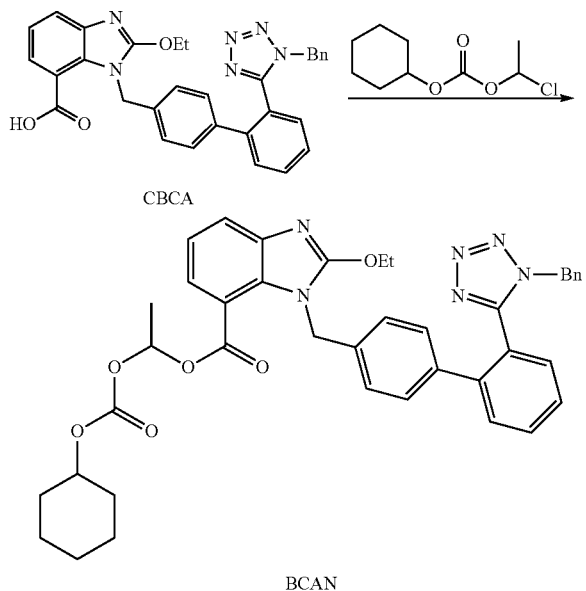

CBCA

BCAN

Acetonitrile (5 mL, 5 vol), CBCA (1 g, 1 equivalent) and potassium carbonate (0.521 g, 2.0 equivalents) were added into a two-neck flask, and 1-chloroethylcyclohexyl carbonate (0.584 g, 1.5 equivalents) was added at 25° C.-30° C. The reaction mixture was heated to 60° C.-65° C. and stirred for 8 hr. The degree of progression of the reaction was confirmed by TLC (TLC eluent: 5% methanol/DCM, detection method: UV). The solvent was evaporated under reduced pressure at 45° C.-50° C., water (5 mL, 5 vol) was added to the concentrated residue, and the resultant product was extracted with ethyl acetate. The organic layer was washed successively with water and saturated brine. The organic layer was concentrated under reduced pressure at 45° C.-50° C. to give a crude resultant product. To this crude resultant product was added cyclohexane (5.0 mL, 5 vol), and the mixture was stirred at 75° C.-85° C. for 1 hr. The mixture was gradually cooled to 5° C.-10° C. and stirred at 5° C.-10° C. for 2 hr. The precipitated solid was filtered, washed with cold cyclohexane (1.0 mL, 1 vol), and dried with suction. The obtained solid was further dried at 50° C.-55° C. for 4 hr to give BCAN (1.1 g, yield 83.3%, HPLC purity: 98.59 area %).

Example 7-6

Deprotection

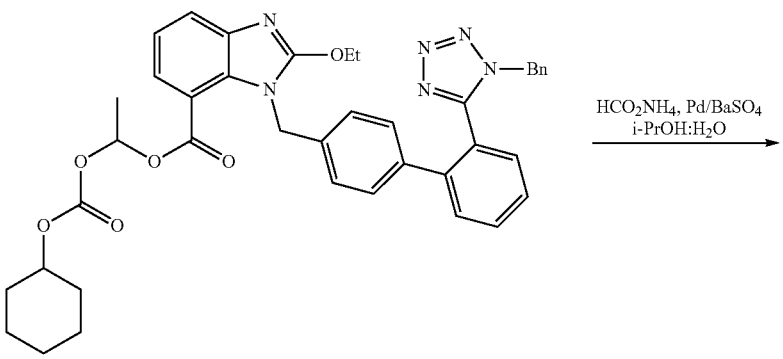

BCAN

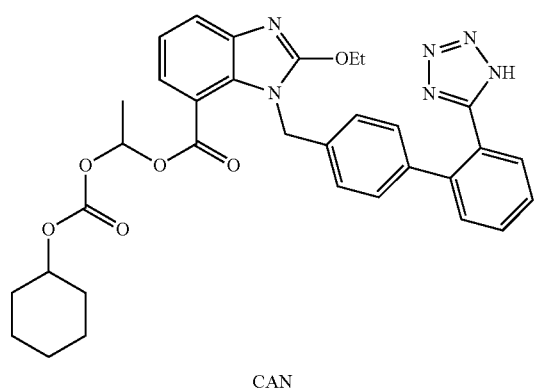

CAN

BCAN (0.1 g, 1 equivalent), ammonium formate (0.045 g, 4.84 equivalents), 5% Pd/BaSO₄-Type29a (0.015 g, 5 mol %), isopropanol (1 mL, 10 vol) and water (0.6 mL, 6 vol) were mixed by stirring in a flask at 25° C.-30° C. The reaction mixture was stirred at 40° C.-45° C. for 16 hr. The degree of progression of the reaction was confirmed by TLC (TLC eluent: 5% methanol/methylene chloride, detection method: UV). The reaction mixture was filtered with a filter lined with celite, and the celite was washed with isopropanol (0.5 mL, 5 vol). The filtrate and washing were combined and concentrated under reduced pressure at 45° C.-50° C. To the concentrated residue was added water (1 mL, 10 vol), whereby precipitation of a solid was observed. The mixture was further stirred for 1 hr, and the precipitated solid was collected by filtration and washed with deionized water (1 mL, 10 vol). The obtained solid was dried with suction, and further dried at 50° C.-55° C. for 5 hr to give CAN (0.07 g, yield 80.45%, HPLC purity 92.20 area %).

Example 7-7

Deprotection

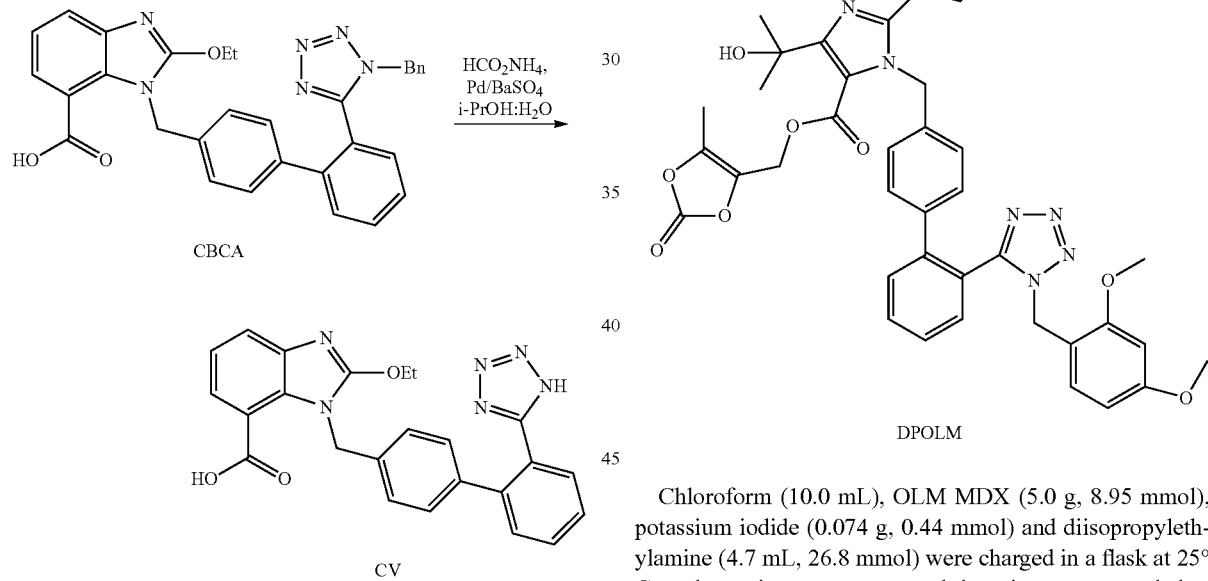

Isopropanol (10 mL, 10 vol), water (6.0 mL, 6 vol), CBCA (1 g, 1 equivalent) and ammonium formate (0.58 g, 4.90 equivalents) were charged in a flask at 25-30° C. 10% Pd/BaSO₄-Type29a (0.1 g, 5 mol %) was added, and the mixture was stirred at 45° C.-50° C. for 6 hr. The degree of progression of the reaction was confirmed by TLC (TLC eluent: 5% methanol/methylene chloride, detection method: UV). The catalyst was filtered off with a filter lined with celite, and the celite was washed with isopropanol (5 mL, 5 vol). The filtrate and washing were combined and concentrated under reduced pressure at 45° C.-50° C. To the concentrated residue were added water (10 mL, 10 vol) and methylene chloride (20 mL, 20 vol), and the mixture was adjusted to pH 5-6 with acetic acid. Precipitation of the solid was observed and the mixture was further stirred for 1 hr.

The obtained solid was collected by filtration, washed with methylene chloride (5 mL, 5 vol), and dried with suction. The solid was further blast-dried at 50° C.-55° C. for 5 hr to give CV (0.6 g, yield 72.28%, HPLC purity: 97.15 area %).

Reference Example 2

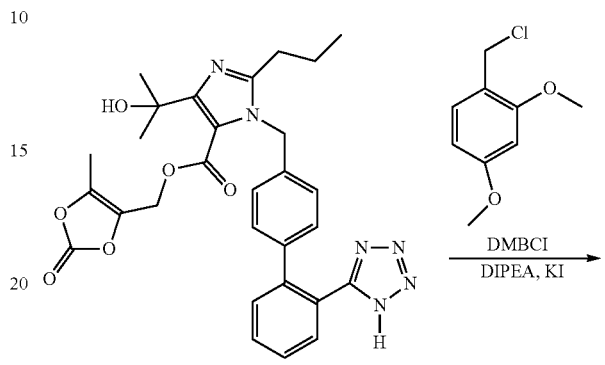

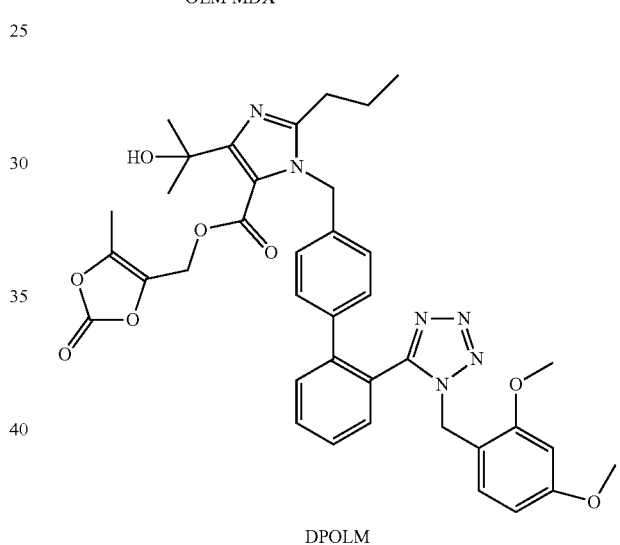

Chloroform (10.0 mL), OLM MDX (5.0 g, 8.95 mmol), potassium iodide (0.074 g, 0.44 mmol) and diisopropylethylamine (4.7 mL, 26.8 mmol) were charged in a flask at 25° C. under a nitrogen stream, and the mixture was cooled to −10° C. to −5° C. Chloroform (5.0 mL), 2,4-dimethoxybenzyl alcohol (2.5 g, 14.86 mmol) and 30% hydrochloric acid (20.0 mL) were added into another flask, and the mixture was stirred for 5 min. The chloroform layer was separated and added to the earlier mixture at −10° C. to −5° C. To the aqueous layer was added chloroform (5.0 mL), and the mixture was partitioned. The chloroform layer was further added to the earlier mixture at −10° C. to −5° C., and the mixture was stirred for 6 hr. After completion of the reaction, water (10.0 mL) was added, and the mixture was stirred for 1 hr and partitioned. The organic layer was washed with water (20.0 mL), and concentrated under reduced pressure. The resultant product was purified by silica gel column chromatography (0.4%-0.5% methanol/methylene chloride) to give the object product.

Example 8

Reaction with Brønsted Acid

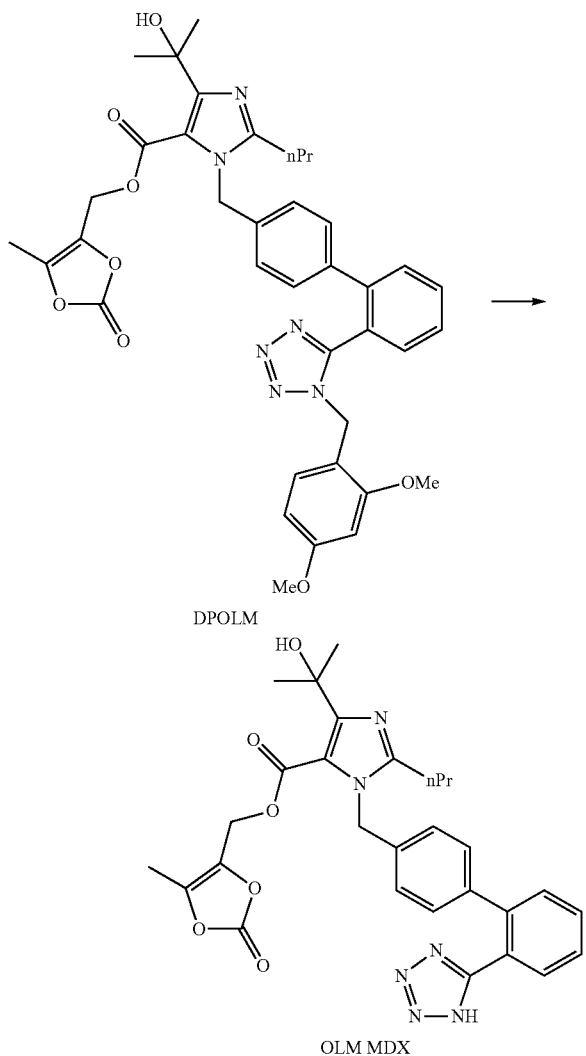

(5-Methyl-2-oxo-1,3-dioxol-4-yl)methyl 4-(1-hydroxy-1-methylethyl)-2-propyl-1-[[2'-[2-(2,4-dimethoxybenzyl)-2H-tetrazol-5-yl]biphenyl-4-yl]methyl]imidazole-5-carboxylate (DPOLM) (0.2 g, 0.28 mmol) was dissolved in methylene chloride (1.0 mL, 5.0 vol), trifluoroacetic acid (0.14 mL) was added at 25° C., and the mixture was stirred for 6 hr. After completion of the reaction, the reaction mixture was concentrated under reduced pressure, to the concentrated residue was added methylene chloride (5 mL), and the mixture was concentrated under reduced pressure. To the concentrated residue was added methylene chloride (5 mL), and the mixture was concentrated under reduced pressure. To the concentrated residue was added methylene chloride (5 mL), and the mixture was filtered through celite. To the filtrate was added 0.5 mol/L aqueous potassium dihydrogen phosphate solution (4 mL), and the mixture was stirred for 30 min. The reaction mixture was adjusted to pH 4-5 with 5% aqueous sodium carbonate solution. The organic layer was partitioned and washed with water (5 mL). The organic layer was dried over sodium sulfate and concentrated under reduced pressure, and the obtained solid was dried under reduced pressure at 45° C. for 1 hr to give olmesartan medoxomil (OLM MDX) (yield 0.154 g, yield 97.5%, HPLC purity: 98.06 area %).

column: Unisol C18 (4.6×150 mm, 3 μm),
buffer: 2.76 g $NaH_2PO_4 \cdot H_2O$ in 1.0 L $H_2O$+1.0 mL $(C_2H_5)_3N$ (adjusted to pH 3.3 with $H_3PO_4$),
mobile phase A (SOLUTION A): buffer/$CH_3CN$ (80/20),
mobile phase B (SOLUTION B): $CH_3CN$,
gradient program: 0 min (SOLUTION A/SOLUTION B=50/50), 2 min (SOLUTION A/SOLUTION B=5/95), 20 min (SOLUTION A/SOLUTION B=5/95), 22 min (SOLUTION A/SOLUTION B=50/50), 25 min (SOLUTION A/SOLUTION B=50/50),
flow: 1.0 mL/min,
injection volume: 10 μL,
column temperature: 30° C.,
dilution solvent: $CH_3CN:H_2O$ (90:10)

INDUSTRIAL APPLICABILITY

According to the present invention, a tetrazole compound, useful as an intermediate for angiotensin II receptor blockers, can be deprotected and an angiotensin II receptor blocker can be produced, under conditions that are economical and suitable for industrial production, by (i) reducing in the presence of a metal catalyst and an alkaline earth metal salt, or (ii) reacting with a specific amount of Brønsted acid.

This application is based on a patent application No. 2012-213212 filed in Japan, the contents of which are incorporated in full herein.

The invention claimed is:

1. A method of producing a compound represented by the formula [3]:

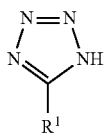

[3]

wherein $R^1$ is an alkyl group, an aralkyl group or an aryl group, each of which is optionally substituted,
or a salt thereof, or
the formula [4]:

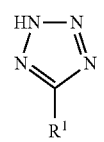

[4]

wherein the symbol is as defined above,
or a salt thereof,
comprising (i) using formic acid or a formic acid salt to reduce
a compound represented by the formula [1]:

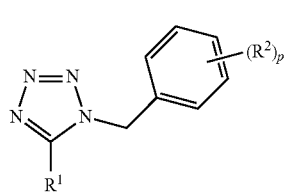

[1]

wherein R¹ is as defined above, R² is methoxy, and p is 0, or a salt thereof, or a compound represented by the formula [2]:

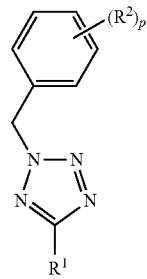

[2]

wherein R¹ is as defined above, R² is methoxy, and p is 0, or a salt thereof, in the presence of palladium barium sulfate, or (ii) reacting a compound represented by the formula [1]

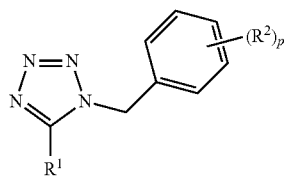

[1]

wherein R¹ is as defined above, each R² is methoxy, and p is 2, or a salt thereof or a compound represented by the formula [2]

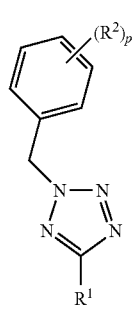

[2]

wherein R¹ is as defined above, each R² is methoxy, and p is 2, or a salt thereof with 0.1 equivalents-50 equivalents of Brønsted acid relative to compound [1] or compound [2].

2. A method of producing a compound represented by the formula [23]:

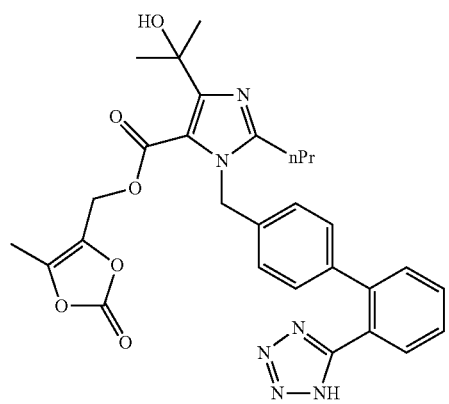

[23]

or a salt thereof, comprising 1) reacting, in the presence of a base, a compound represented by the formula [11]:

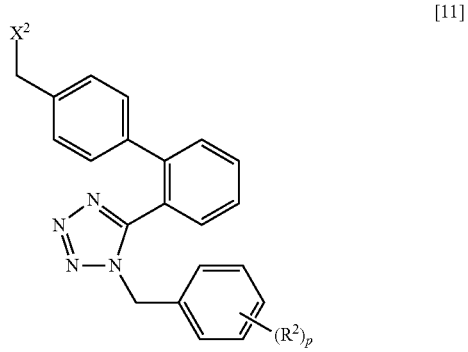

[11]

wherein each R² is methoxy, p is 0 or 2, and X² is a halogen atom, or a salt thereof, with a compound represented by the formula [15]:

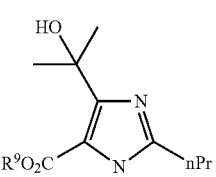

[15]

wherein R⁹ is a carboxy-protecting group, or a salt thereof to give a compound represented by the formula [16]:

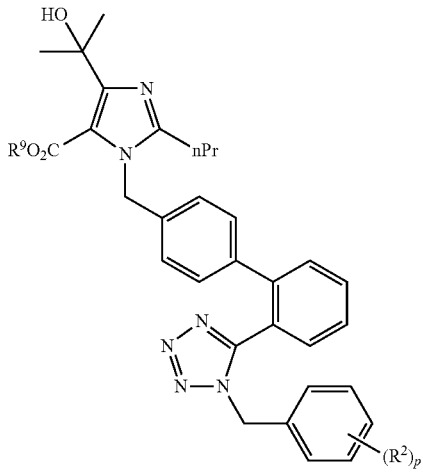

[16]

wherein the symbols are as defined above, or a salt thereof;

2) (i) using formic acid or a formic acid salt to reduce a compound represented by the formula [16] or a salt thereof in the presence of palladium barium sulfate, when p is 0 in the compound of formula [16], or (ii) reacting a compound represented by the formula [16] or a salt thereof with 0.1 equivalents-50 equivalents of Brønsted acid relative to compound [16], when p is 2 in the compound of formula [16], to give a compound represented by the formula [17]:

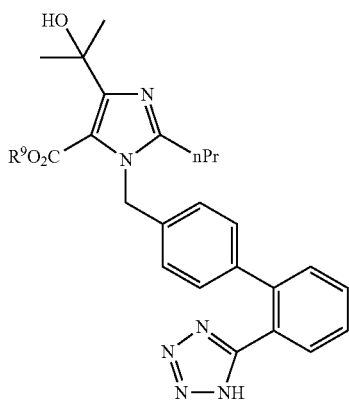

[17]

wherein the symbol is as defined above, or a salt thereof;

3) reacting a compound represented by the formula [17] or a salt thereof with a compound represented by the formula [18]: Tr-X wherein Tr is a trityl group and X is a halogen atom in the presence of a base to give a compound represented by the formula [19]:

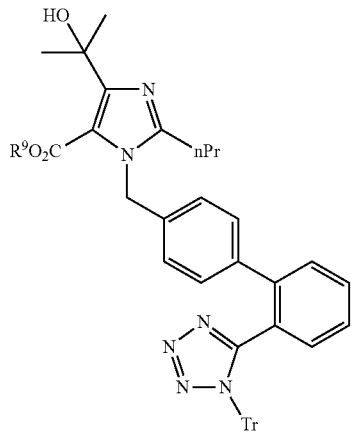

[19]

wherein the symbol is as defined above, or a salt thereof;

4) removing $R^9$ of a compound represented by the formula [19] or a salt thereof to give a compound represented by the formula [20]:

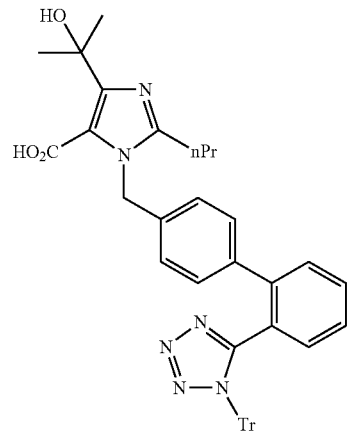

[20]

wherein the symbol is as defined above, or a salt thereof;

5) reacting a compound represented by the formula [20] or a salt thereof with a compound represented by the formula [21]:

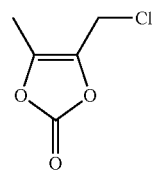

[21]

to give a compound represented by the formula [22]:

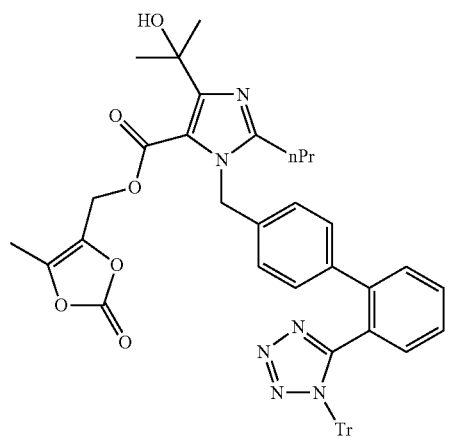

wherein the symbol is as defined above,
or a salt thereof; and
6) removing a trityl group of a compound represented by the formula [22] or a salt thereof.

3. A method of producing a compound represented by the formula [28]:

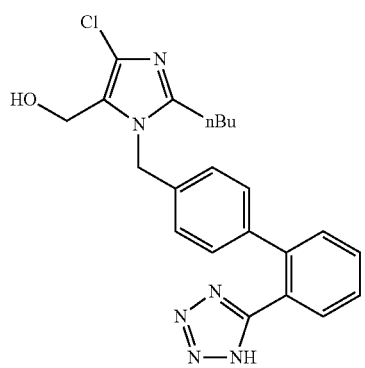

or a salt thereof,
comprising
1) reacting a compound represented by the formula [11]:

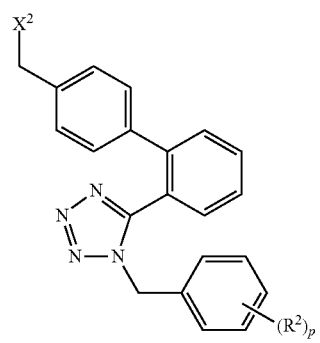

wherein each $R^2$ is methoxy, p is 0 or 2, and $X^2$ is a halogen atom,
or a salt thereof with a compound represented by the formula [24]:

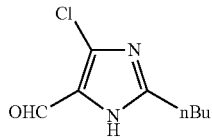

or a salt thereof
to give a compound represented by the formula [25]:

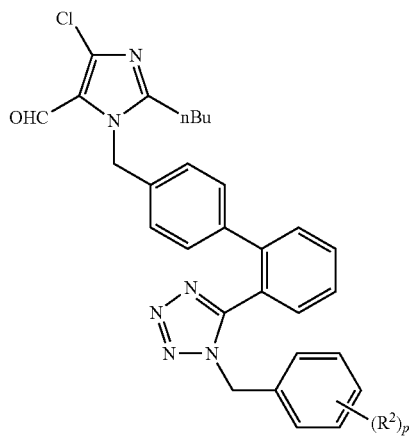

wherein the symbol is as defined above,
or a salt thereof; and
2-A) reducing a compound represented by the formula [25] or a salt thereof with a reducing agent to give a compound represented by the formula [26]:

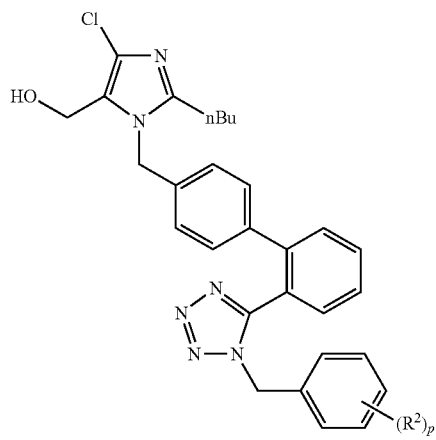

wherein $R^2$ and p are as defined above,
or a salt thereof, and
(i) further using formic acid or a formic acid salt to reduce a compound represented by the formula [26] or a salt thereof in the presence of palladium barium sulfate, when p is 0 in the compound of formula [26], or (ii) reacting a compound represented by the formula [26] or a salt thereof with 0.1 equivalents-50 equivalents of Brønsted acid relative to a compound represented by the formula [26] or a salt thereof, when p is 2 in the compound of formula [26], or 2-B) (i) using formic acid or a formic acid salt to reduce a compound represented by the formula [25] or a salt thereof in the presence of palladium barium sulfate, when p is 0 in the compound of formula [25], or (ii) reacting a compound represented by the formula [25] or a salt thereof with 0.1 equivalents-50 equivalents of Brønsted acid relative to a compound represented by the formula [25] or a salt thereof, when p is 2 in the compound of formula [25], to give a compound represented by the formula [27]:

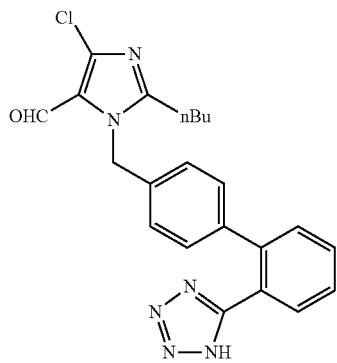

[27]

or a salt thereof, and
further reducing a compound represented by the formula [27] or a salt thereof with a reducing agent.

4. A method of producing a compound represented by the formula [35]:

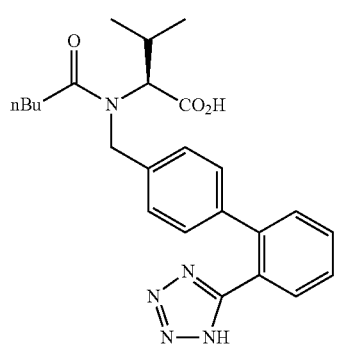

[35]

or a salt thereof,
comprising
1) reacting a compound represented by the formula [11]:

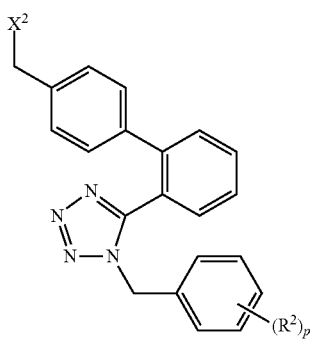

[11]

wherein each $R^2$ is methoxy, p is 0 or 2, and $X^2$ is a halogen atom,
or a salt thereof
with a compound represented by the formula [29]:

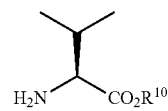

[29]

wherein $R^{10}$ is a carboxy-protecting group,
or a salt thereof
to give a compound represented by the formula [30]:

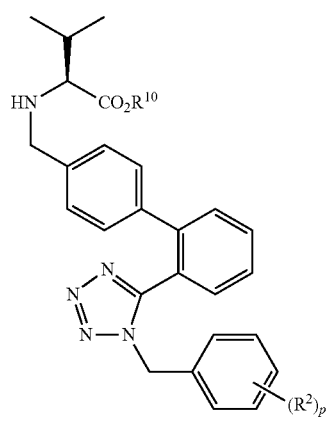

[30]

wherein the symbols are as defined above,
or a salt thereof;

2-A) (i) using formic acid or a formic acid salt to reduce a compound represented by the formula [30] or a salt thereof in the presence of palladium barium sulfate, when p is 0 in the compound of formula [30], or (ii) reacting a compound represented by the formula [30] or a salt thereof with 0.1 equivalents-50 equivalents of Brønsted acid relative to a compound represented by the formula [30] or a salt thereof, when p is 2 in the compound of formula [30], to give a compound represented by the formula [31]:

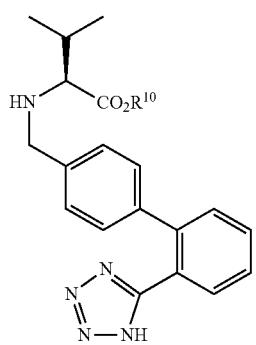

[31]

wherein the symbol is as defined above,
or a salt thereof;

3-A) reacting a compound represented by the formula [31] or a salt thereof with a compound represented by the formula [32]: CH₃CH₂CH₂CH₂CO—X³ wherein X³ is a leaving group to give a compound represented by the formula [33]:

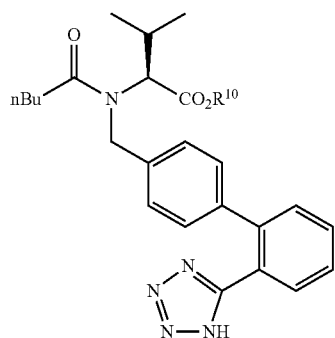

[33]

wherein the symbol is as defined above, or a salt thereof;

4-A) removing $R^{10}$ of a compound represented by the formula [33] or a salt thereof; or 2-B) reacting a compound represented by the formula [30] or a salt thereof with a compound represented by the formula [32] or a salt thereof to give a compound represented by the formula [34]:

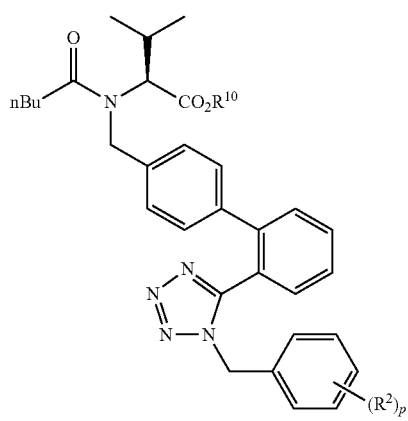

[34]

wherein the symbols are as defined above, or a salt thereof; and

3-B) (i) using formic acid or a formic acid salt to reduce a compound represented by the formula [34] or a salt thereof in the presence of palladium barium sulfate, when p is 0 in the compound of formula [34], to remove $R^{10}$, or (ii) reacting a compound represented by the formula [34] or a salt thereof with 0.1 equivalents-50 equivalents of Brønsted acid relative to a compound represented by the formula [34] or a salt thereof, when p is 2 in the compound of formula [34], to remove $R^{10}$.

5. A method of producing a compound represented by the formula [38]:

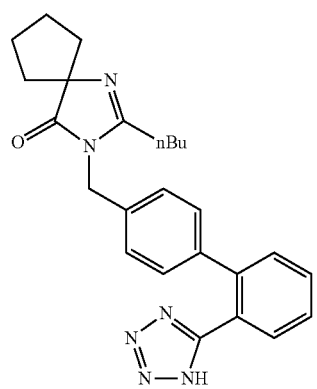

[38]

or a salt thereof,
comprising
1) reacting a compound represented by the formula [11]:

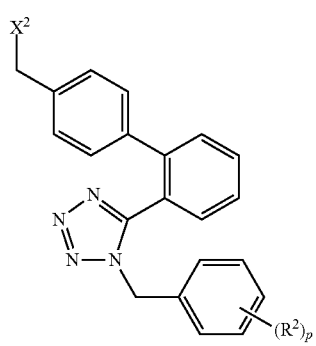

[11]

wherein each $R^2$ is methoxy, p is 0 or 2, and $X^2$ is a halogen atom,
or a salt thereof
with a compound represented by the formula [36]:

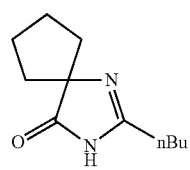

[36]

or a salt thereof to give a compound represented by the formula [37]:

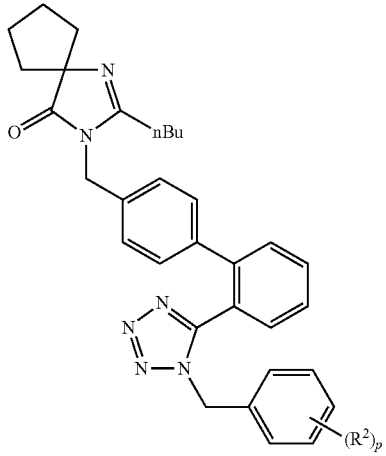

[37]

wherein the symbol is as defined above,
or a salt thereof, and
2) (i) further using formic acid or a formic acid salt to reduce a compound represented by the formula [37] or a salt thereof in the presence of palladium barium sulfate, when p is 0 in the compound of formula [37], or (ii) reacting a compound represented by the formula [37] or a salt thereof with 0.1 equivalents-50 equivalents of Brønsted acid relative to a compound represented by the formula [37] or a salt thereof, when p is 2 in the compound of formula [37].

6. A method of producing a compound represented by the formula [47]:

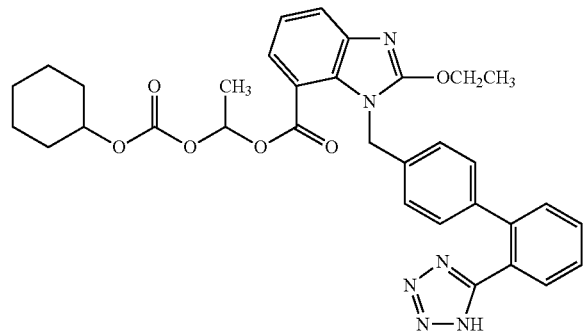

[47]

or a salt thereof,
comprising
1-A-i) reacting a compound represented by the formula [11]:

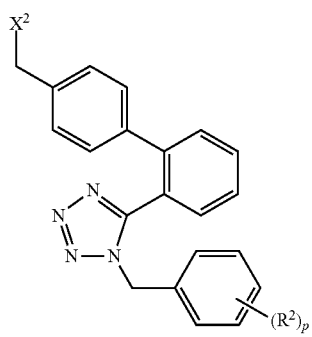

[11]

wherein each $R^2$ is methoxy, p is 0 or 2, and $X^2$ is a halogen atom, or a salt thereof, with a compound represented by the formula [39]:

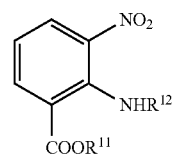

[39]

wherein $R^{11}$ is a carboxy-protecting group, and $R^{12}$ is an amino-protecting group,
or a salt thereof
to give a compound represented by the formula [40]:

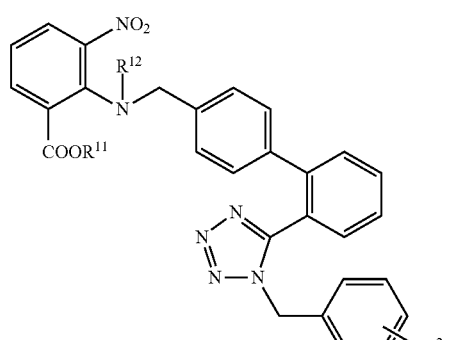

[40]

wherein the symbols are as defined above,
or a salt thereof;

1-A-ii) removing $R^{12}$ of a compound represented by the formula [40] or a salt thereof to give a compound represented by the formula [41]:

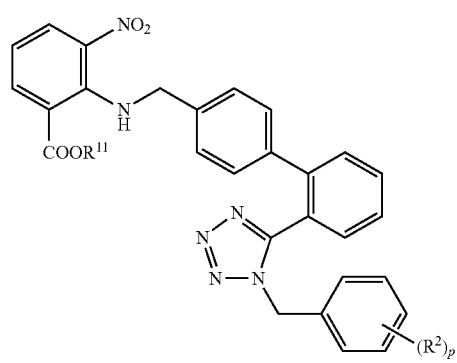

[41]

wherein the symbols are as defined above,
or a salt thereof;

1-A-iii) reducing a compound represented by the formula [41] or a salt thereof to give a compound represented by the formula [42]:

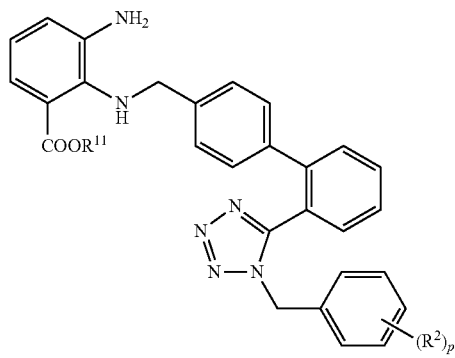

wherein the symbols are as defined above, or a salt thereof;

1-A-iv) reacting a compound represented by the formula [42] or a salt thereof with tetraethoxymethane; or 1-B) reacting a compound represented by the formula [11]:

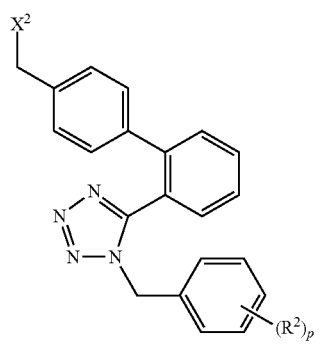

wherein each $R^2$ is methoxy, p is 0 or 2, and $X^2$ is a halogen atom, or a salt thereof, with a compound represented by the formula [49]:

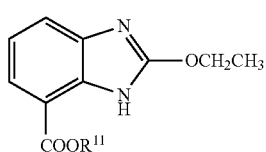

wherein the symbol is as defined above, to give a compound represented by the formula [43]:

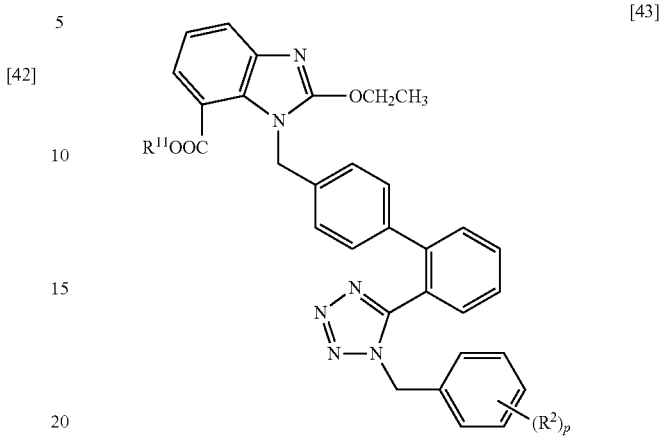

wherein the symbols are as defined above, or a salt thereof;

2) removing $R^{11}$ of a compound represented by the formula [43] or a salt thereof to give a compound represented by the formula [44]:

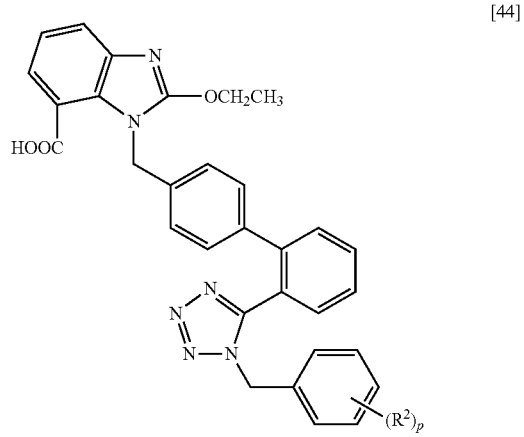

wherein the symbol is as defined above, or a salt thereof;

3) reacting a compound represented by the formula [44] or a salt thereof with a compound represented by the formula [45]:

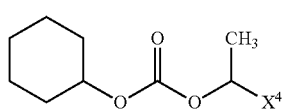

wherein $X^4$ is a leaving group or a hydroxyl group, or a salt thereof to give a compound represented by the formula [46]:

[46]

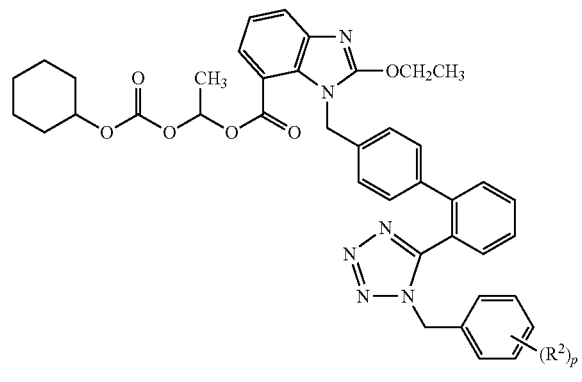

wherein the symbol is as defined above, or a salt thereof; and 4) (i) using formic acid or a formic acid salt to reduce a compound represented by the formula [46] or a salt thereof in the presence of palladium barium sulfate, when p is 0 in the compound of formula [46], or (ii) reacting a compound represented by the formula [46] or a salt thereof with 0.1 equivalents-50 equivalents of Brønsted acid relative to a compound represented by the formula [46] or a salt thereof, when p is 2 in the compound of formula [46].

7. A compound represented by the formula [48]:

[48]

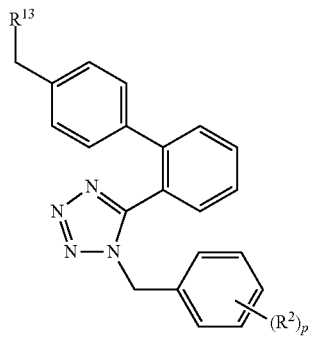

wherein $R^2$ is methoxy, p is 0, and $R^{13}$ is

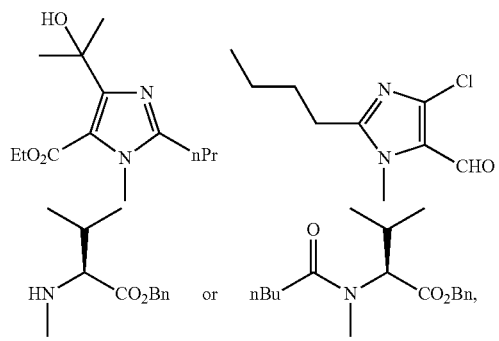

or a salt thereof.

* * * * *